(12) United States Patent
Beard et al.

(10) Patent No.: US 11,964,994 B2
(45) Date of Patent: Apr. 23, 2024

(54) TWO-DIMENSIONAL PEROVSKITE COMPOSITIONS AND DEVICES THEREFROM

(71) Applicants: Alliance for Sustainable Energy, LLC, Golden, CO (US); University of Utah Research Foundation, Salt Lake City, UT (US); Duke University, Durham, NC (US)

(72) Inventors: Matthew C. Beard, Arvada, CO (US); Haipeng Lu, Lakewood, CO (US); Annalise Elizabeth Maughan, Arvada, CO (US); Joseph Jonathan Berry, Boulder, CO (US); Zeev Valentine Vardeny, Salt Lake City, UT (US); Chuanxiao Xiao, Lakewood, CO (US); Volker Wolfgang Blum, Durham, NC (US); David Brian Mitzi, Hillsborough, NC (US)

(73) Assignees: Alliance for Sustainable Energy, LLC, Golden, CO (US); Duke University, Durham, NC (US)

( * ) Notice: Subject to any disclaimer, the term of this patent is extended or adjusted under 35 U.S.C. 154(b) by 661 days.

(21) Appl. No.: 17/109,668

(22) Filed: Dec. 2, 2020

(65) Prior Publication Data

US 2021/0175439 A1 Jun. 10, 2021

Related U.S. Application Data

(60) Provisional application No. 62/942,375, filed on Dec. 2, 2019, provisional application No. 63/024,707, filed on May 14, 2020.

(51) Int. Cl.
*C07F 7/24* (2006.01)
*C07C 211/65* (2006.01)
(Continued)

(52) U.S. Cl.
CPC .............. *C07F 7/24* (2013.01); *C07C 211/65* (2013.01); *C07F 7/2208* (2013.01); *H10K 85/50* (2023.02); *H10K 10/50* (2023.02)

(58) Field of Classification Search
CPC ........ C07C 211/65; C07F 7/2208; C07F 7/24; H10K 10/50; H10K 85/50
See application file for complete search history.

(56) References Cited

FOREIGN PATENT DOCUMENTS

KR        20190004942 A  *  1/2019

OTHER PUBLICATIONS

Huang et al. "Magneto-Optical Detection of Photoinduced Magnetism via Chirality-Induced Spin Selectiveity in 2D Chiral Hybrid Organic-Inorganic Perovskites", ACS Nano, 2020, vol. 14, p. 10370-10375. (Year: 2020).*

(Continued)

*Primary Examiner* — Gerard Higgins
(74) *Attorney, Agent, or Firm* — Michael A. McIntyre

(57) ABSTRACT

The present disclosure relates to a composition that includes a perovskite of $A_2BX_4$, where A includes an R-form of a chiral molecule of at least one of (Continued)

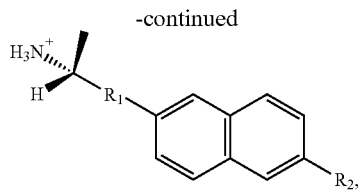

-continued and/or an S-form of the chiral molecule, B includes a cation, X includes an anion, $R_1$ includes a first carbon chain having between 2 and 5 carbon atoms, $R_2$ includes at least one of a hydrogen atom, a halogen atom, a carboxylic acid group, an alkoxy group, and/or a second carbon chain, and $R_3$ includes a third carbon chain.

20 Claims, 52 Drawing Sheets

(51) Int. Cl.
  *C07F 7/22* (2006.01)
  *H10K 10/50* (2023.01)
  *H10K 85/50* (2023.01)

(56) References Cited

OTHER PUBLICATIONS

Ahn, J. et al., "A new class of chiral semiconductors: chiral-organic-molecule-incorporating organic-inorganic hybrid perovskites," Materials Horizons, vol. 4, 2017, 5 pages.
Ahn, J. et al., "Chiral 2D Organic Inorganic Hybrid Perovskite with Circular Dichroism Tunable Over Wide Wavelength Range, " Journal of the American Chemical Society, vol. 142, 2020, 7 pages.
Ben-Moshe, A. et al., "Probing the Interaction of Quantum Dots with Chiral Capping Molecules Using Circular Dichroism Spectroscopy," Nano Letters, vol. 16, 2016, 7 pages.
Billing, D. et al., "Synthesis and crystal structures of inorganic-organic hybrids incorporating an aromatic amine with a chiral functional group," CrystEngComm, vol. 8, 2006, 10 pages.
Chen, X. et al., "Impact of Layer Thickness on the Charge Carrier and Spin Coherence Lifetime in Two-Dimensional Layered Perovskite Single Crystals," ACS Energy Letters, vol. 3, 2018, 7 pages.
Elliott, S., "Chiral Shells and Achiral Cores in CdS Quantum Dots," Nano Letters, vol. 8, No. 8, 2008, 6 pages.
Goto, T. et al., "Localization of triplet excitons and biexcitons in the two-dimensional semiconductor (CH3C6H4CH2NH3)2PbBr4," Physical Review B, vol. 73, 2006, 5 pages.
Huang, P-J. et al., "Bulk Photovoltaic Effect in a Pair of Chiral-Polar Layered Perovskite-Type Lead Iodides Altered by Chirality of Organic Cations," Journal of the American Chemical Society, vol. 141, 2019, 4 pages.
Katan, C. et al., "Quantum and Dielectric Confinement Effects in Lower-Dimensional Hybrid Perovskite Semiconductors," Chemical Reviews, vol. 119, 2019, 53 pages.
Kepenekian, M. et al., "Rashba and Dresselhaus Effects in Hybrid Organic-Inorganic Perovskites: From Basics to Devices," ACS Nano, vol. 9, No. 12, 2015, 11 pages.
Kepenekian, M. et al., "Rashba and Dresselhaus Couplings in Halide Perovskites: Accomplishments and Opportunities for Spintronics and Spin-Orbitronics," J. Phys. Chem. Letters, vol. 8, 2017, 9 pages.
Kiran, V. et al., "Structure dependent spin selectivity in electron transport through oligopeptides," Journal of Chemical Physics, vol. 146, 2016, 5 pages.
Li, J. et al., "Optical spintronics in organic-inorganic perovskite photovoltaics," Physical Review B, vol. 93, 2016, 9 pages.
Long, G. et al., "Spin control in reduced-dimensional chiral perovskites," Nature Photonics, Letters, vol. 12, 2018, 7 pages.
Lu, H. et al., "Spin-dependent charge transport through 2D chiral hybrid lead-iodide perovskites," Science Advances, vol. 5, 2019, 8 pages.
Ma, J. et al., "Chiral 2D Perovskites with a High Degree of Circularly Polarized Photoluminescence," ACS Nano, vol. 13, 2019, 7 pages.
McGuire, T.R. et al., "Anisotropic Magnetoresistance in Ferromagnetic 3d Alloys," IEEE Transactions on Magnetics, vol. Mag-11, No. 4, 1975, 21 pages.
Naaman, R., "Chiral-Induced Spin Selectivity Effect," Journal of Physical Chemistry Letters, vol. 3, 2012, 10 pages.
Naaman, R. et al., "Spintronics and Chirality: Spin Selectivity in Electron Transport Through Chiral Molecules," Annual Rev. Phys. Chem., 2015, 22 pages.
Niesner, D. et al., "Giant Rashba Splitting in CH3NH3PbBr3 Organic-Inorganic Perovskite," Physical Review Letters, vol. 117, 2016, 6 pages.
Odenthal, P. et al., "Spin-polarized exciton quantum beating in hybrid organic-inorganic perovskites," Nature Physics, vol. 13, 2017, 7 pages.
Park, In-H. et al., "Ferroelectricity and Rashba Effect in a Two-Dimensional Dion-Jacobson Hybrid Organic-Inorganic Perovskite," Journal of the American Chemical Society, vol. 141, 2019, 5 pages.
Saparov, B. et al., "Organic-Inorganic Perovskites: Structural Versatility for Functional Materials Design," Chemical Reviews, vol. 116, 2016, 39 pages.
Wang, J. et al., "Spin-optoelectronic devices based on hybrid organic-inorganic trihalide perovskites," Nature Communications, vol. 10, No. 129, 2019, 6 pages.
Xie, Z. et al., "Spin Specific Electron Conduction through DNA Oligomers," Nano Letters, vol. 11, 2011, 4 pages.
Xiong, Z.H. et al., "Giant magnetoresistance in organic spin-valves," Nature, vol. 427, 2004, 4 pages.
Yin, J. et al., "Layer-Dependent Rashba Band Splitting in 2D Hybrid Perovskites," Chemistry of Materials, vol. 30, 2018, 8 pages.
Zhai, Y. "Giant Rashba splitting in 2D organic-inorganic halide perovskites measured by transient spectroscopies," Science Advances, vol. 3, 2017, 7 pages.
Zhang, T. et al., "Stable and Efficient 3D-2D Perovskite-Perovskite Planar Heterojunction Solar Cell Without Organic Hole Transport Layer," Joule 2, 2018, 17 pages.
Zhou, C. et al., "Photoluminescence spectral broadening, chirality transfer and amplification of chiral perovskite materials (R-X-p-mBZA)2PbBr4 (X=H, F, Ci, Br) regulated by van der Waals and halogen atoms interactions," Phys. Chem. Chem. Phys.I, vol. 22, 2020, 7 pages.
Zhou, Y. et al., "Similar Topological Origin of Chiral Centers in Organic and Nanoscale Inorganic Structures: Effect of Stabilizer Chirality on Optical Isomerism and Growth of CdTe Nanocrystals," Journal of American Chemical Society, vol. 132, 2010, 8 pages.

\* cited by examiner

TWO-DIMENSIONAL PEROVSKITE COMPOSITIONS AND DEVICES THEREFROM

CROSS-REFERENCE TO RELATED APPLICATIONS

This application claims priority from U.S. Provisional Patent Application Nos. 62/942,375 and 63/024,707 filed on Dec. 2, 2019 and May 14, 2020, respectively, the contents of which are incorporated herein by reference in their entirety.

CONTRACTUAL ORIGIN

This invention was made with government support under Contract No. DE-AC36-08GO28308 awarded by the Department of Energy. The government has certain rights in the invention.

BACKGROUND

Spintronics, which takes advantage of not only the carrier (electron or hole) charge but also the spin degrees of freedom, provides a promising direction for the next generation of information technologies, and is of special interest to quantum computing constructs. The key challenge in a spintronic device is to control the spin-polarized electron density, that is, to manipulate the number of electrons with well-defined spin-states. Hybrid organic-inorganic perovskite (HOIP) semiconductors offer an opportunity to directly incorporate chiral organic molecules in the production of a 2D-layered hybrid perovskite thin film and/or crystal that induces chirality into the inorganic sub-lattice band-edge states. However, there remains a need for efficient and reliable HOIP materials that can meet the stringent physical property and performance requirements needed for the production of HOIP spintronic materials on a large scale.

SUMMARY

An aspect of the present disclosure is a composition that includes a perovskite of $A_2BX_4$, where A includes an R-form of a chiral molecule of at least one of

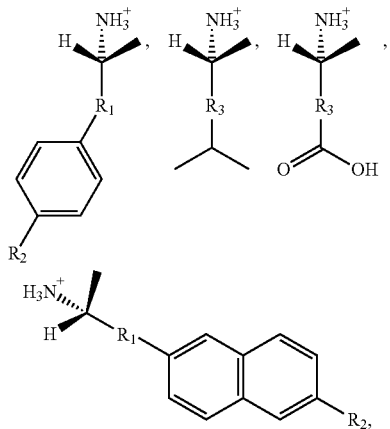

and/or an S-form of the chiral molecule, B includes a cation, X includes an anion, $R_1$ includes a first carbon chain having between 2 and 5 carbon atoms, $R_2$ includes at least one of a hydrogen atom, a halogen atom, a carboxylic acid group, an alkoxy group, and/or a second carbon chain, and $R_3$ includes a third carbon chain.

In some embodiments of the present disclosure, the chiral molecule may include at least one of

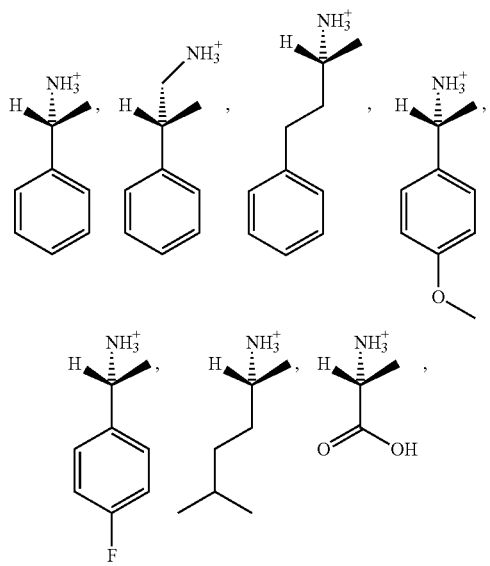

and/or the S-form equivalent of the chiral molecule.

In some embodiments of the present disclosure, the chiral molecule may include at least one of methylbenzylammonium (MBA), β-methylphenethylammonium, 1-methyl-3-phenylpropylammonium, 2-amino-5-methylhexane, 4-methoxy-α-methylbenzylammonium, 4-fluoro-α-methylbenzylammonium, 4-bromo-α-methylbenzylammonium, and/or alanine. In some embodiments of the present disclosure, the composition may demonstrate spin-polarization of charge transport when a current is injected into the composition.

In some embodiments of the present disclosure, B may include at least one of lead, tin, and/or germanium. In some embodiments of the present disclosure, X may include a halogen. In some embodiments of the present disclosure, the perovskite may include at least one of $R\text{-MBA}_2PbI_4$, $S\text{-MBA}_2PbI_4$, $R\text{-MBA}_2SnI_4$, $S\text{-MBA}_2SnI_4$, $R\text{-MBA}_2Pb_{1-x}Sn_xI_4$, and/or $S\text{-MBA}_2Pb_{1-x}Sn_xI_4$, where $0<x<1$. In some embodiments of the present disclosure, the perovskite may be in a form that includes a first two-dimensional (2D) network and a second 2D network, where the first 2D network includes $BX_4$, the second 2D network includes $BX_4$, and a plurality of the chiral molecule forms a layer positioned between the first 2D network and the second 2D network. In some embodiments of the present disclosure, the perovskite may be in a shape of a film having a thickness between about 10 nm and about 100 nm. In some embodiments of the present disclosure, the film may have a roughness between about 1 nm and about 5 nm. In some embodiments of the present disclosure, the perovskite may have a bandgap between about 2.2 eV and about 3.0 eV.

An aspect of the present disclosure is a device that includes a perovskite that includes $A_2BX_4$, where A includes an R-form of a chiral molecule of at least one of

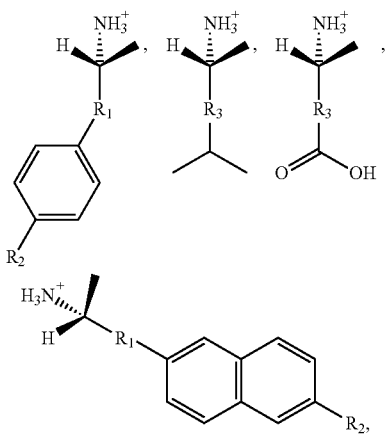

and/or an S-form of the chiral molecule, B includes a cation, X includes an anion, $R_1$ includes a first carbon chain having between 2 and 5 carbon atoms, $R_2$ includes at least one of a hydrogen atom, a halogen atom, a carboxylic acid group, an alkoxy group, and/or a second carbon chain, and $R_3$ includes a third carbon chain.

In some embodiments of the present disclosure, the device may be configured to operate as at least one of an FM electrode, a spin filter, a spin polarized LED, a spin polarized laser, an op spin-valve, a spin-diode, a spin-transistor, a chiral-light detector, a switchable optical memory, a polarization selective optical multiplexor, and/or an ultrafast modulator. In some embodiments of the present disclosure, the perovskite may be in a shape of a film. In some embodiments of the present disclosure, the device may further include a first electrode and a second electrode, where the film is positioned between the first film and the second film. In some embodiments of the present disclosure, the first electrode may include a transparent conducting oxide (TCO). In some embodiments of the present disclosure, the TCO may include indium tin oxide. In some embodiments of the present disclosure, the second electrode may include at least one of nickel and/or iron. In some embodiments of the present disclosure, the second electrode may have a thickness between about 1 nm and about 10 nm. In some embodiments of the present disclosure, the device may further include a metal layer, where the second electrode is positioned between the metal layer and the perovskite.

BRIEF DESCRIPTION OF THE DRAWINGS

Some embodiments are illustrated in referenced figures of the drawings. It is intended that the embodiments and figures disclosed herein are to be considered illustrative rather than limiting.

FIG. 4A illustrates the crystalline structure of chiral perovskite (R/S-) methylbenzylammonium lead iodide (R/S-MBA)$_2$PbI$_4$ (where MBA is methylbenzylammonium).

FIGS. 4B-4D illustrate the crystallographic orientation characterization of perovskite thin films: 1D where the dark data set corresponds to (R-MBA)$_2$PbI$_4$ and the light data set corresponds to (S-MBA)$_2$PbI$_4$ (FIG. 4B), and 2D XRD patterns (FIGS. 4C and 4D). Note that layers are highly oriented as only (0 0 2h) peaks are present. Intense Bragg spots further indicate the layers orient parallel to the substrates.

(FIG. 5A): (R-MBA)$_2$PbI$_4$, (FIG. 5B): (rac-MBA)$_2$PbI$_4$, (FIG. 5C): (S-MBA)$_2$PbI$_4$, (FIG. 5D): (PEA)$_2$PbI$_4$. It can be clearly seen that 2D perovskite films are highly oriented.

(FIG. 7A): (R-MBA)$_2$PbI$_4$, (FIG. 7B): (rac-MBA)$_2$PbI$_4$, (FIG. 7C): (S-MBA)$_2$PbI$_4$, (FIG. 7D): (PEA)$_2$PbI$_4$. The inset shows the AFM step profile for the corresponding films. The step profile AFM samples were prepared by employing a blade and vertically scratching the sample surface followed by nitrogen blowing away the dust.

(FIGS. 8A and 8C) CD spectrum with fit for S- and R-(MBA)$_2$PbI$_4$ perovskite thin films (~50 nm). The fitting procedure is provided in detail below. From the fitting, the total energy splitting can be determined as ΔE=51.3 meV. (FIG. 8B) Linear absorption spectrum for (R-/S-MBA)$_2$PbI$_4$. (FIG. 8D) A scheme depicted the energy shift and the resulting bi-polar feature in CD spectrum.

FIG. 9A illustrates a schematic illustration of mCP-AFM measurements and FIGS. 9B-9D illustrate the chirality dependence in out-of-plane charge transport. Room temperature current-voltage (I-V) curves obtained using the mCP-AFM technique of chiral 2D hybrid perovskite thin films (~50 nm thick) for (R-MBA)$_2$PbI$_4$ (FIG. 9B), (S-MBA)$_2$PbI$_4$ (FIG. 9D) and non-chiral perovskite film, phenethylammonium lead iodide, PEA$_2$PbI$_4$ (FIG. 9C). The tip is magnetized in the north (N,^), south (S, +), and non-magnetized (*). The I-V response for each 2D film was averaged over 100 scans, and the shaded region around the lines mark the 95% confidence limits for the average results.

(R-MBA)$_2$PbI$_4$, (Panels D-F): PEA$_2$PbI$_4$, (Panels G-I): (S-MBA)$_2$PbI$_4$. The statistic 95% confident limit is defined as $$\left(\bar{x} - z^* \times \frac{\sigma}{\sqrt{n}}, \bar{x} + z^* \times \frac{\sigma}{\sqrt{n}}\right),$$

where $\bar{x}$, $z^*$, $\sigma$ and n are the mean value, 1.96 (for 95% confidence), standard deviation, and the total scan number, respectively.

Figure 11A:
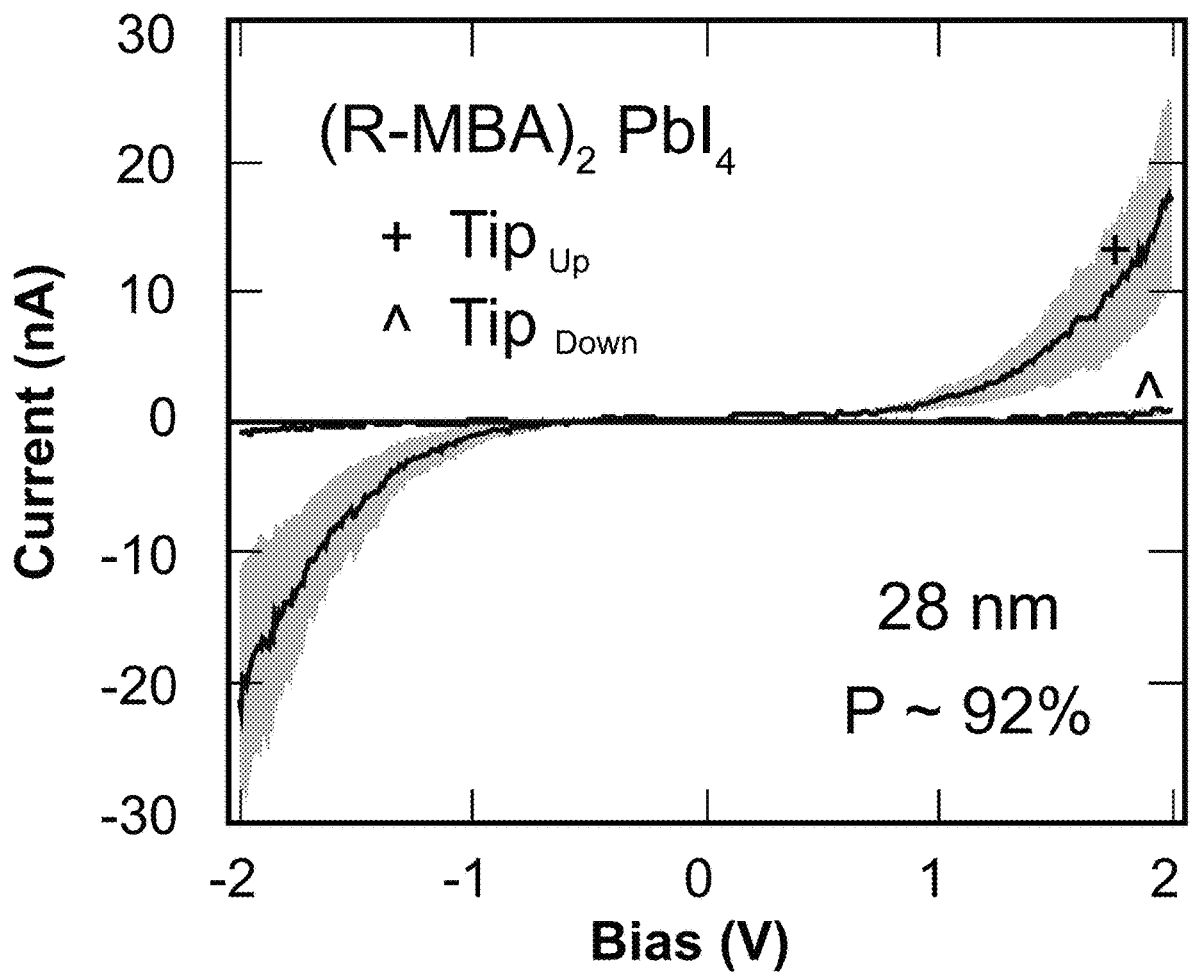
Figure 11B:
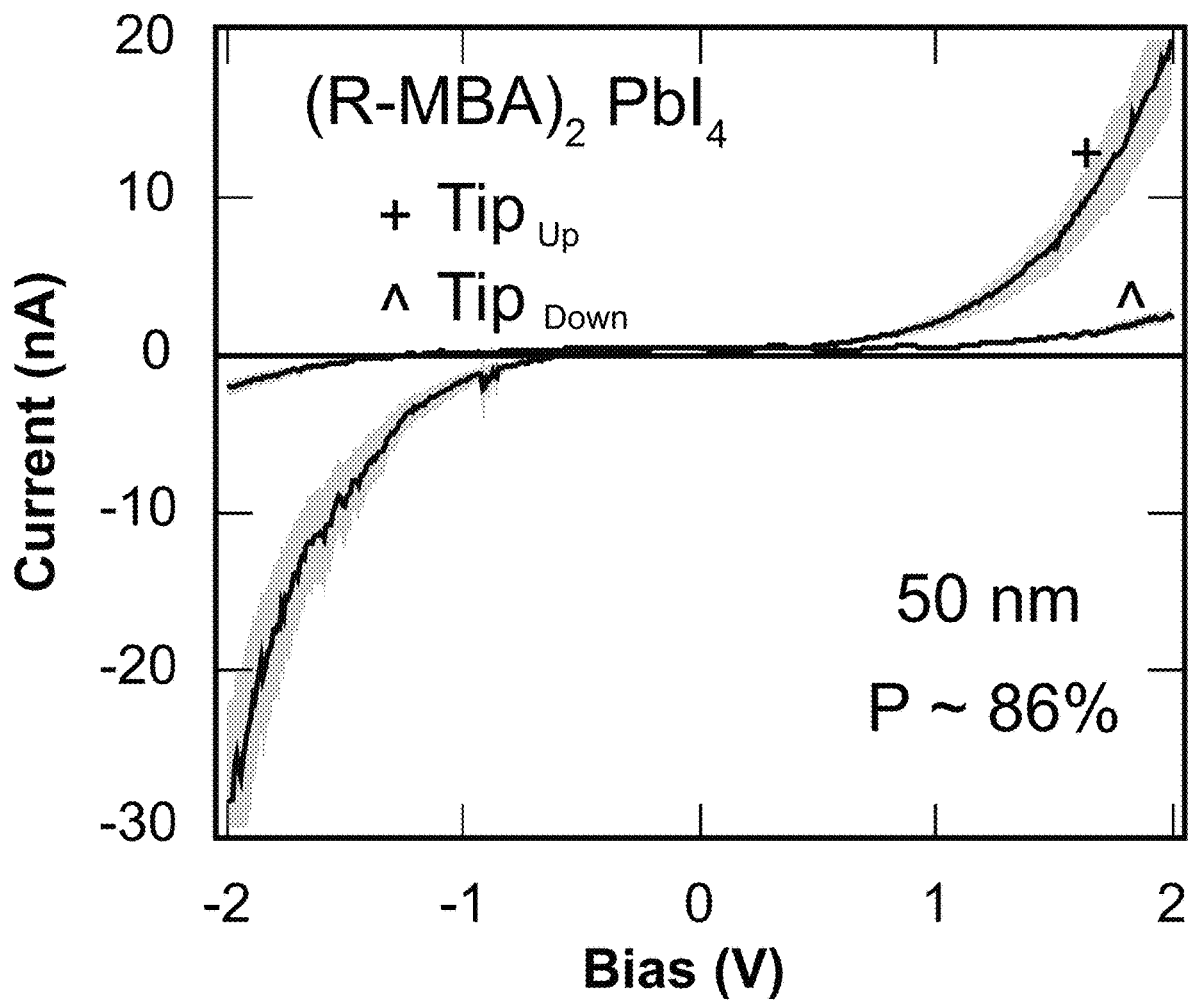
Figure 11C:
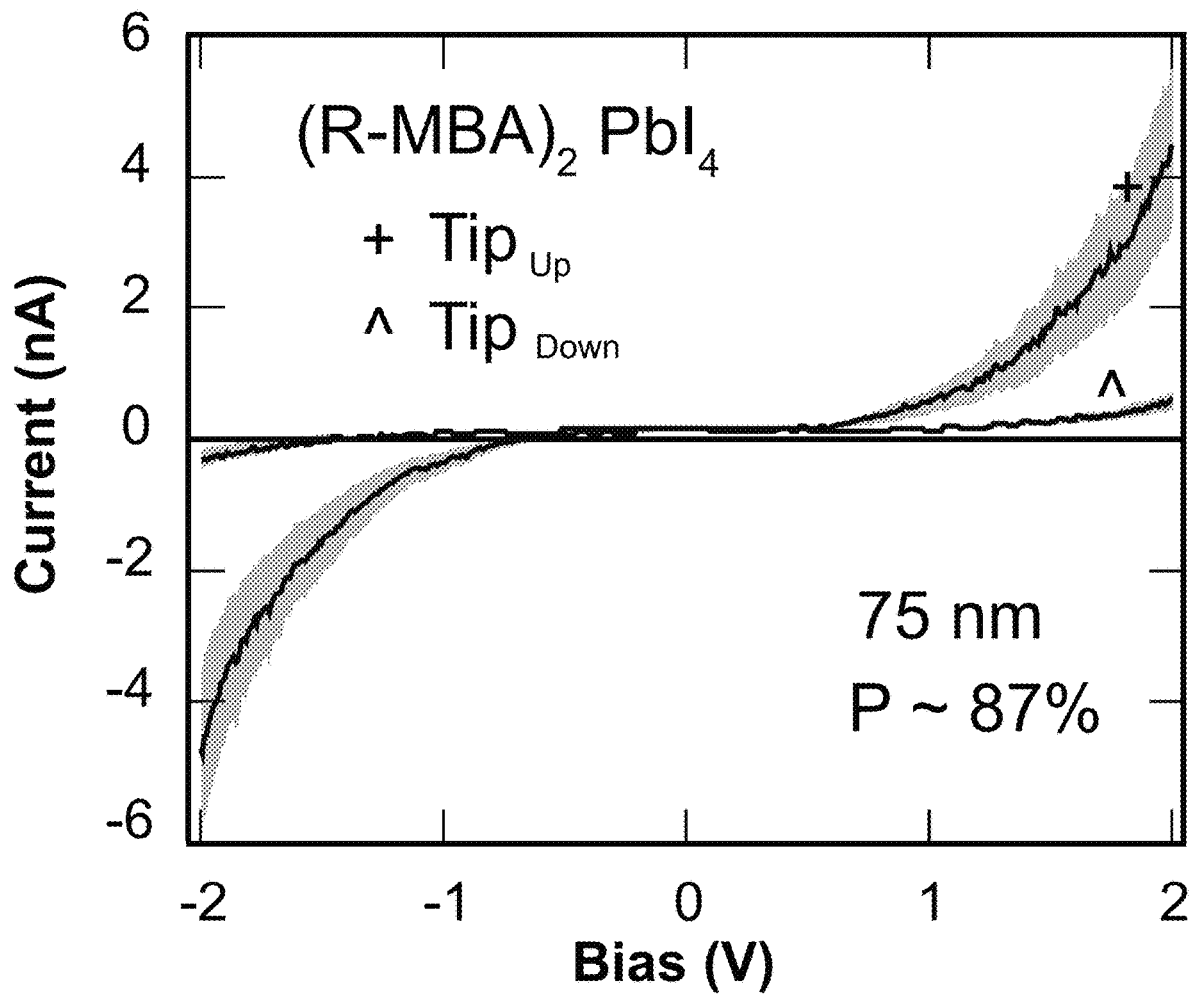

FIGS. 11A-11C illustrate thickness dependence mCP-AFM studies, according to some embodiments of the present disclosure. It can be clearly seen that P is consistently high (86-92%) for (R-MBA)$_2$PbI$_4$ films with 28-75 nm thickness, and it does not show strong thickness dependence in this thickness regime.

Figure 12A:
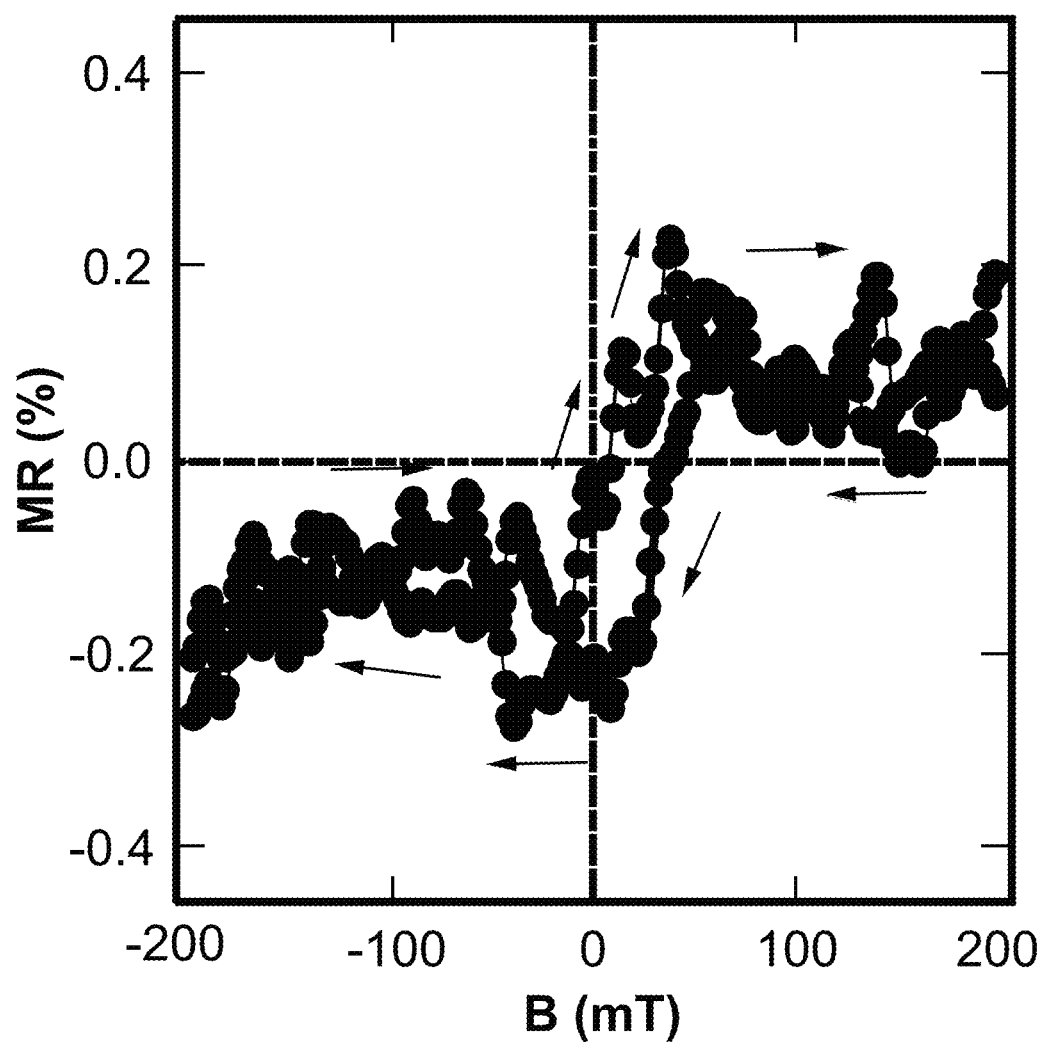
Figure 12B:
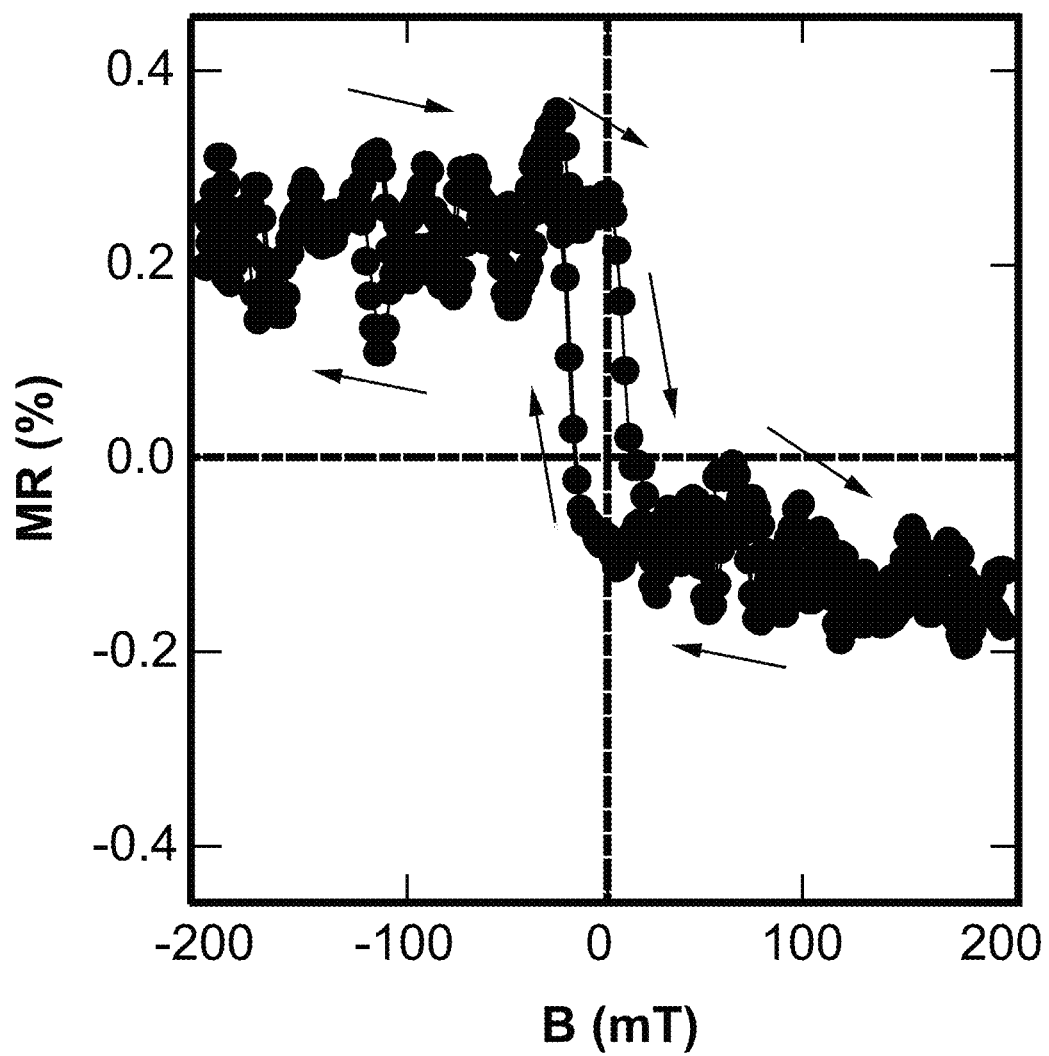
Figure 12C:
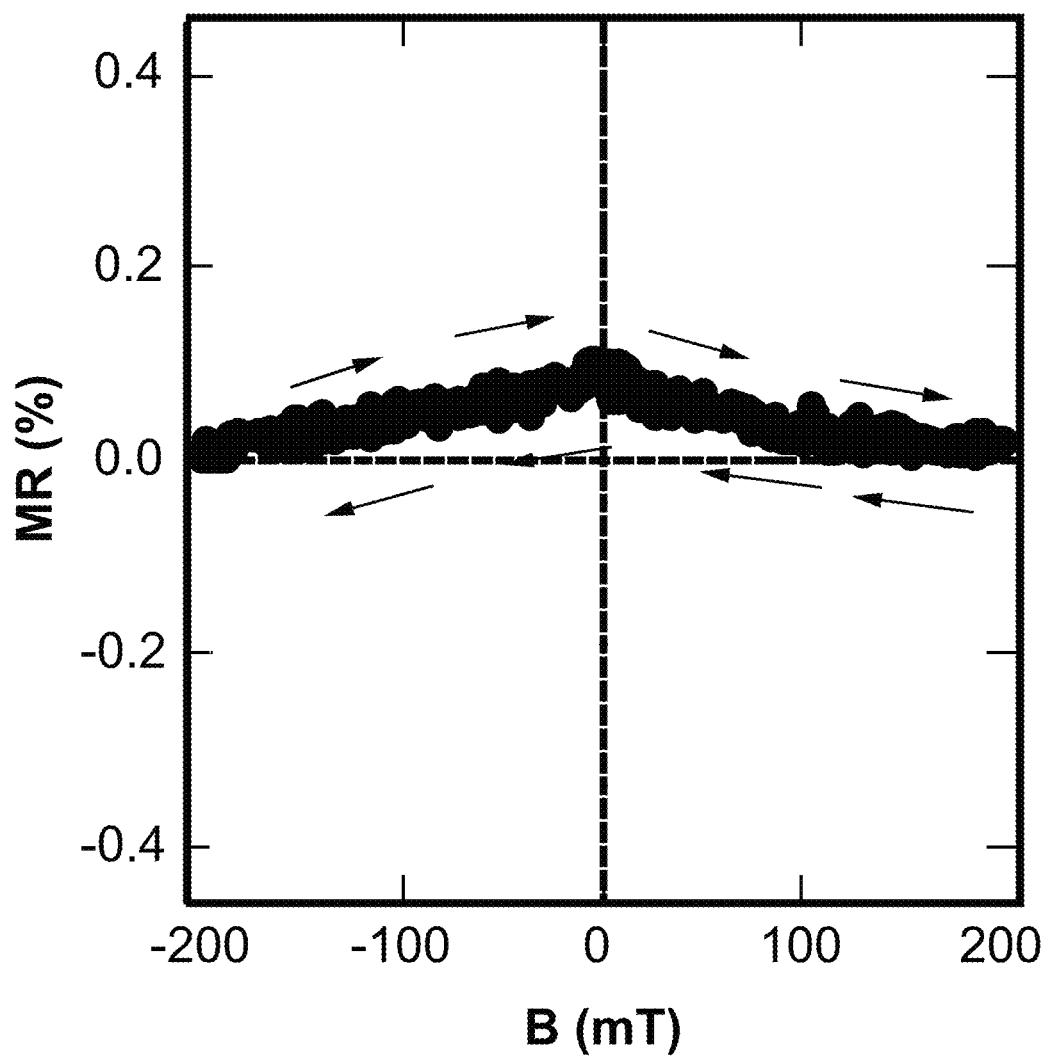

FIGS. 12A-12C illustrate the magnetoresistance (MR) response of spintronics devices based on chiral perovskites and a schematic illustration of the device structure, according to some embodiments of the present disclosure. MR(B) response of spintronic devices based on (R-MBA)$_2$PbI$_4$ (see FIG. 12A), (S-MBA)$_2$PbI$_4$ (see FIG. 12B) and (PEA)$_2$PbI$_4$ (see FIG. 12C). The out-of-plane magnetic field was swept from −200 mT and 200 mT and back. The resistance was measured at applied forward voltage of 0.5 V and temperature of 10K. The interlayer perovskite film thickness was ~60 nm for all devices.

Figure 13:
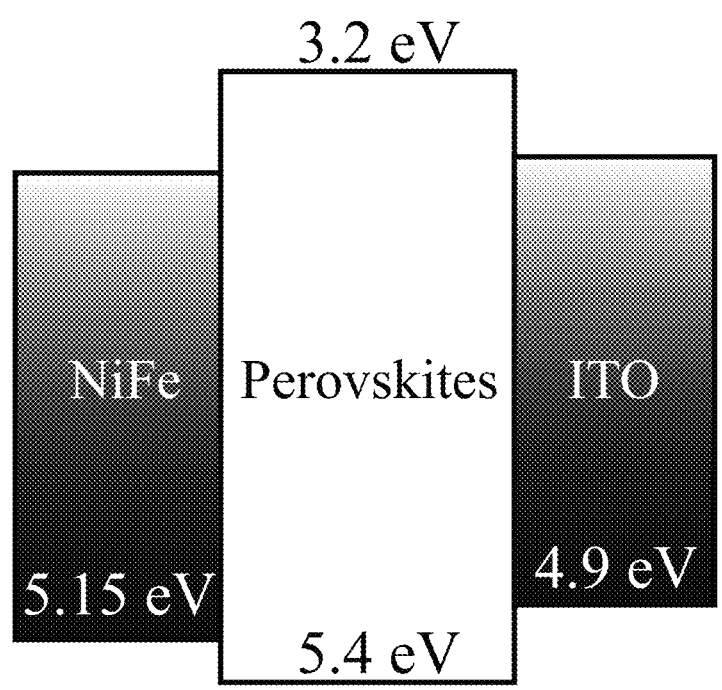

FIG. 13 illustrates a schematic energy diagram of the 'half spin valve' device based on the chiral 2D perovskite thin films, according to some embodiments of the present disclosure. Band edge positions of chiral 2D perovskites are estimated based on literature reports.

Figure 14A:
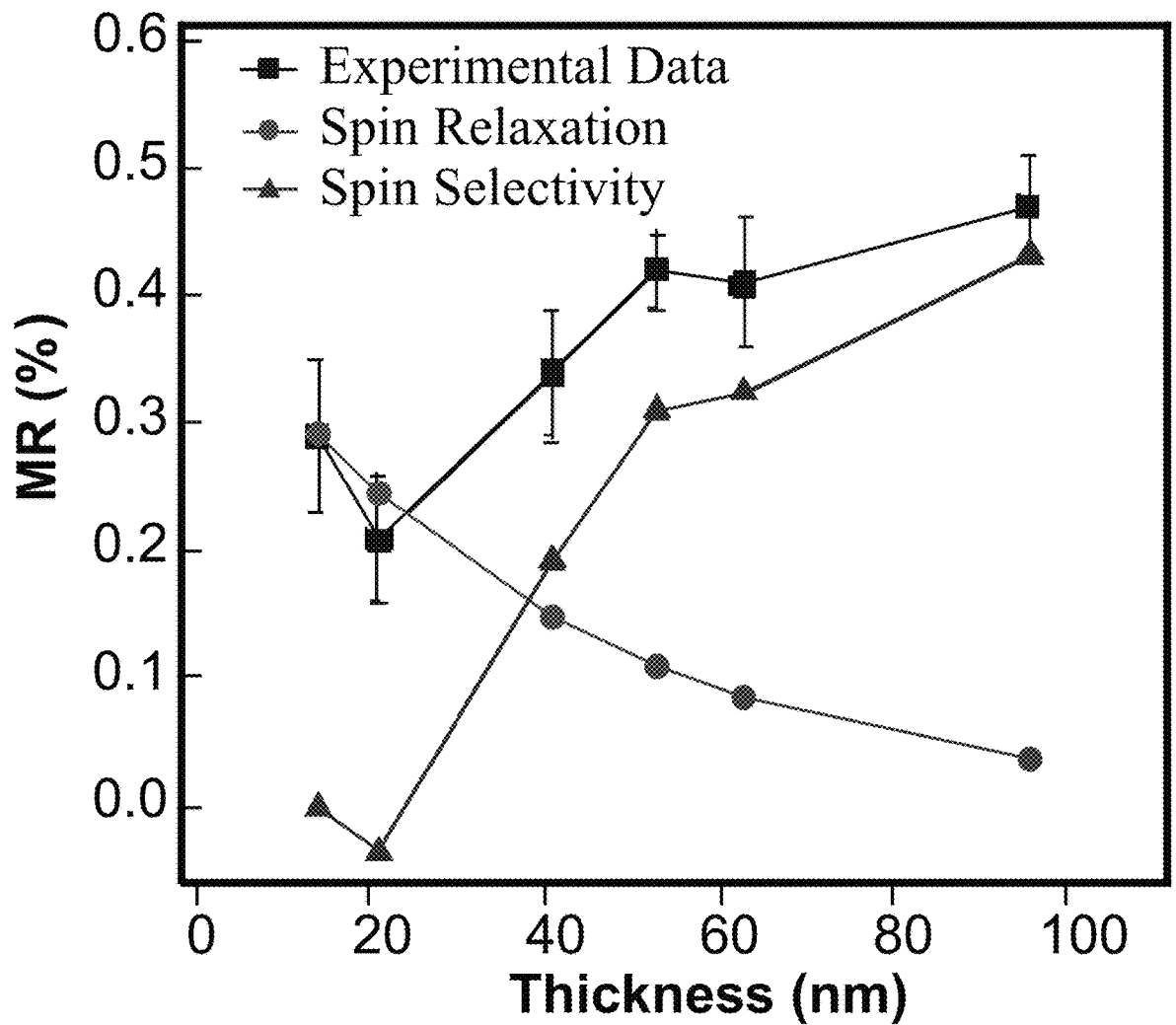
Figure 14B:
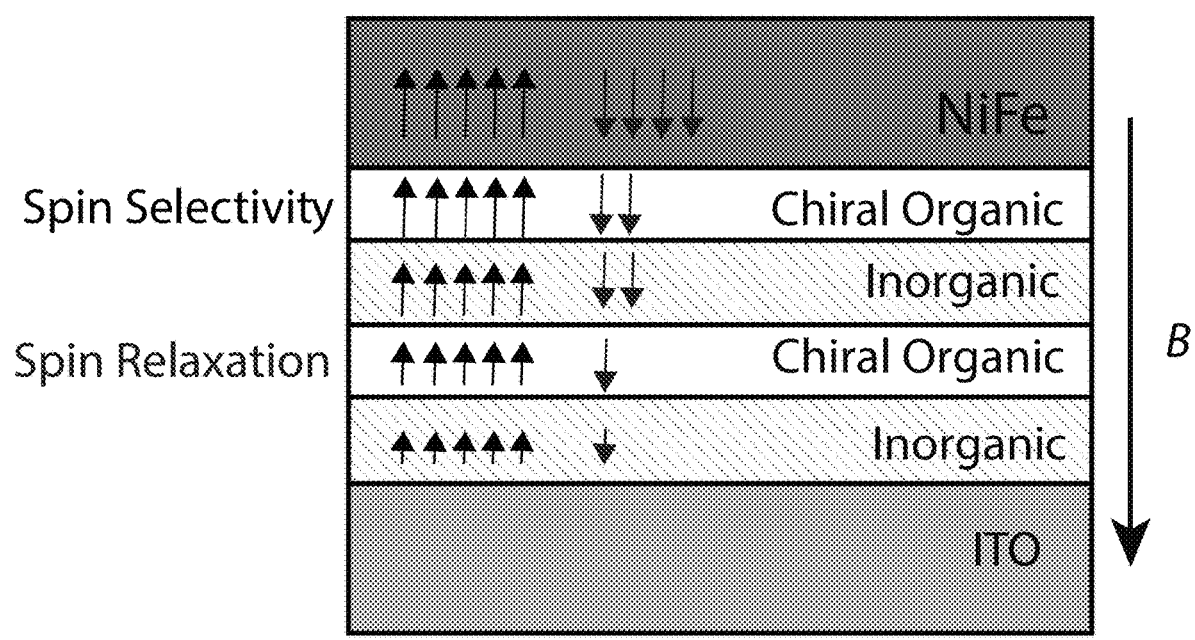

FIGS. 14A and 14B illustrate thickness dependent magnetoresistance (MR) study and schematic diagram of the spin transport through the 2D chiral perovskite layers, according to some embodiments of the present disclosure. The MR$_{max}$(d) response was decomposed into two components in spintronic devices based on (S-MBA)$_2$PbI$_4$ with difference thicknesses (FIG. 14A). The squares are experimental MR$_{max}$(d); whereas the circles are simulation of spin relaxation process (exponential decay with thickness, assuming a spin diffusion length of ~40 nm). The difference between the squares and circles are represented by the triangles, which is a rough estimation of the spin selectivity dependence with the thickness. These two competing effects are illustrated in (FIG. 14B). Spin selectivity occurred through each chiral layer, whereas spin relaxation happened mainly through each inorganic layer which possesses strong spin-orbit coupling (SOC).

Figure 15:
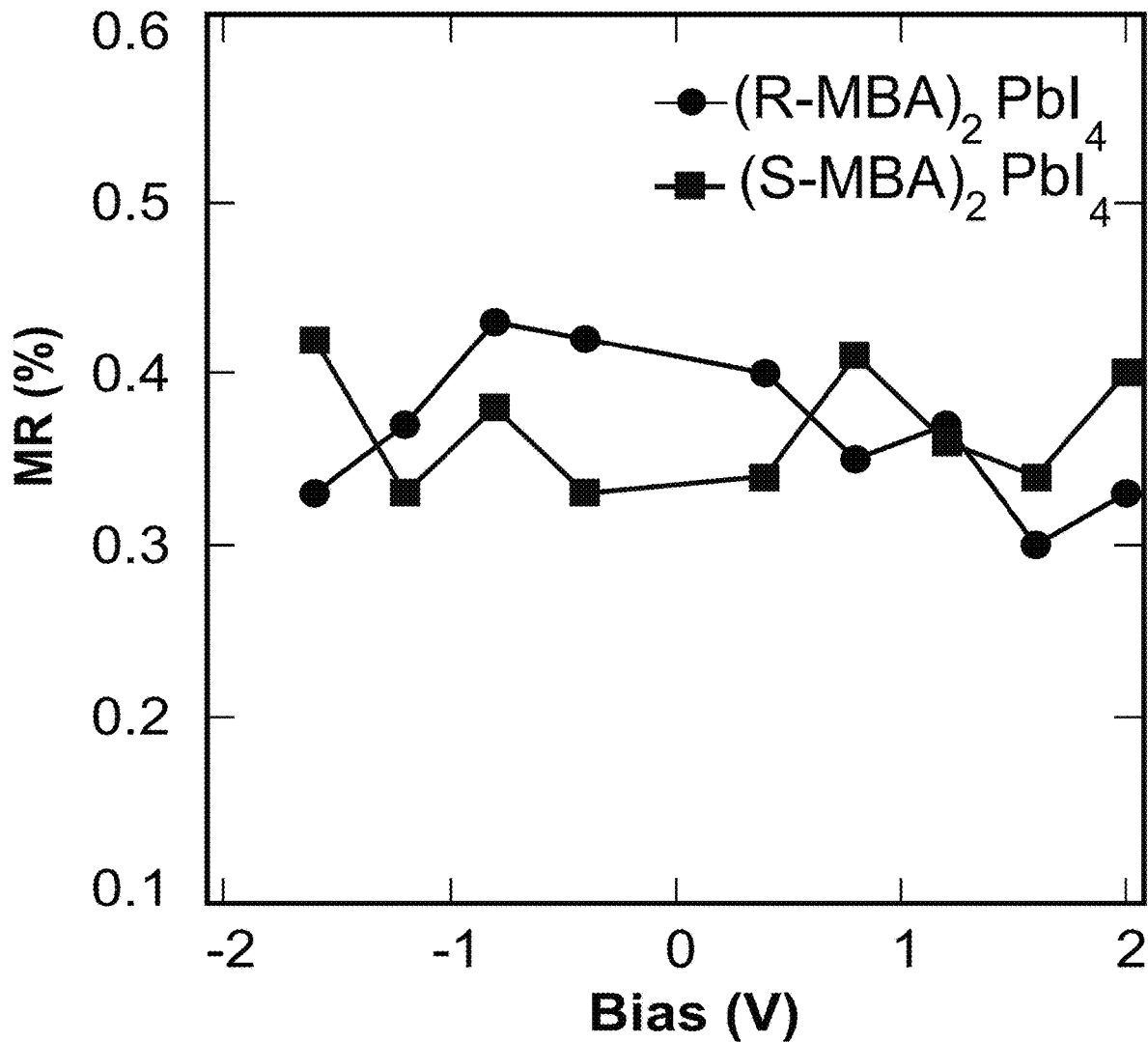

FIG. 15 illustrates voltage dependent MR studies based on chiral (R-MBA)$_2$PbI$_4$ and (S-MBA)$_2$PbI$_4$ thin films, according to some embodiments of the present disclosure.

Figure 16:
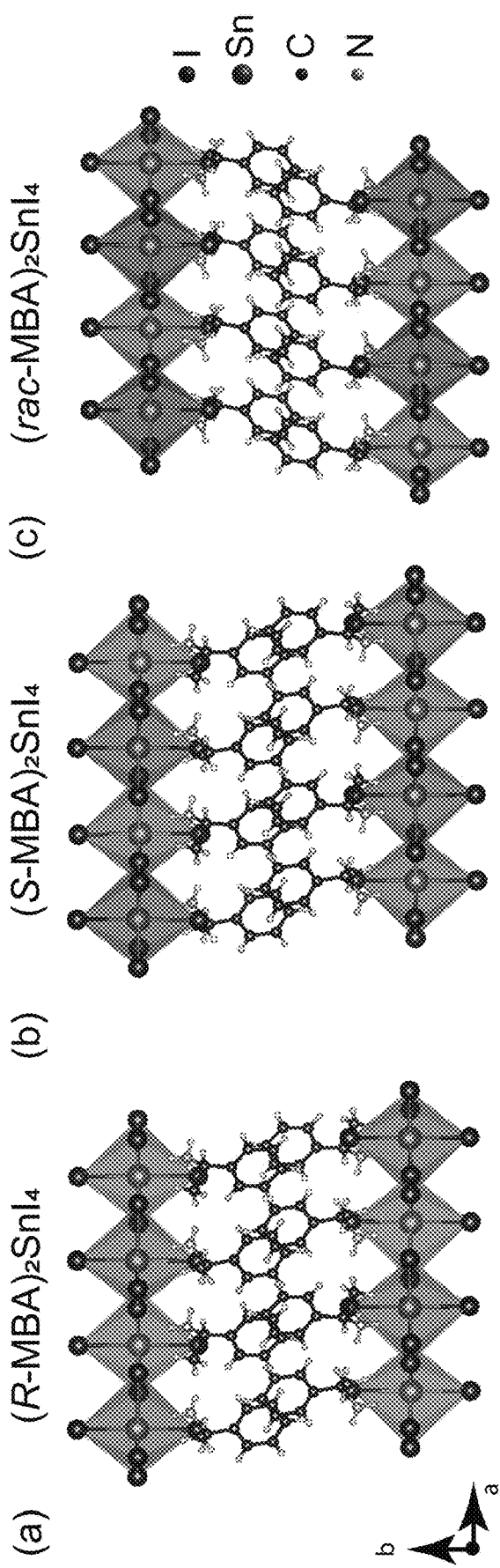

FIG. 16 illustrates the crystal structures of (a) (R-MBA)$_2$SnI$_4$, (b) (S-MBA)$_2$SnI$_4$, and (c) (rac-MBA)$_2$SnI$_4$ from the side-view along the c direction, according to some embodiments of the present disclosure. The axes shown correspond to all structures in a-c.

Figure 17:
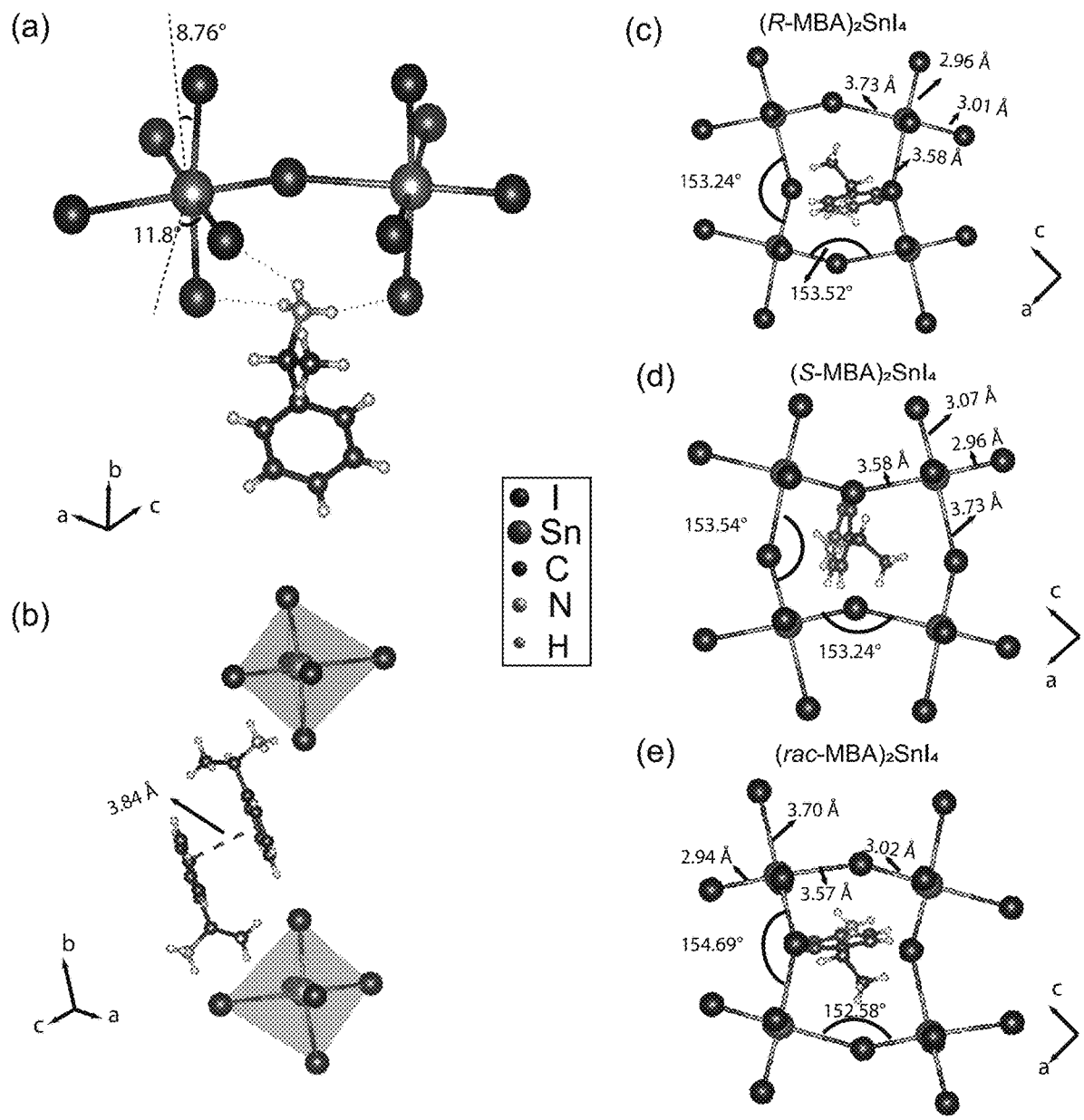

FIG. 17 illustrates, according to some embodiments of the present disclosure: (a) Hydrogen bonds between the organic R-MBA cation and inorganic octahedra in (R-MBA)$_2$SnI$_4$. (b) π-π stacking of R-MBA cations along b direction. (c-e) Top-down view of crystal structures of (R-MBA)$_2$SnI$_4$, (S-MBA)$_2$SnI$_4$, and (rac-MBA)$_2$SnI$_4$, respectively. An in-plane distortion of the octahedra can be clearly observed.

Figure 18:
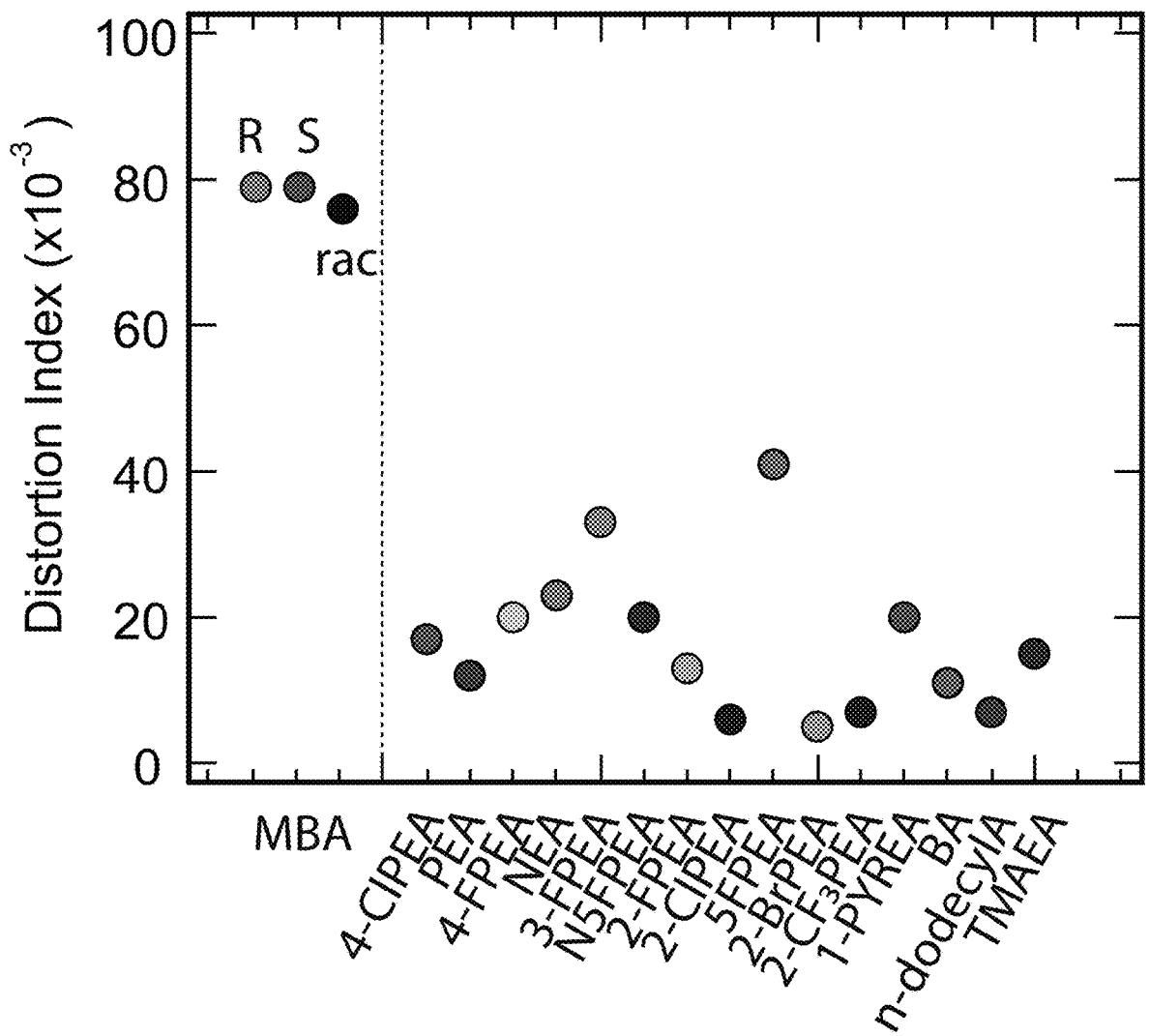

FIG. 18 illustrates bond length distortion indices (D) of (R-MBA)$_2$SnI$_4$, (S-MBA)$_2$SnI$_4$, and (rac-MBA)$_2$SnI$_4$ compounds, calculated based on the new crystal structures described herein, with comparison to other Sn-I perovskites, according to some embodiments of the present disclosure.

Figure 19A:
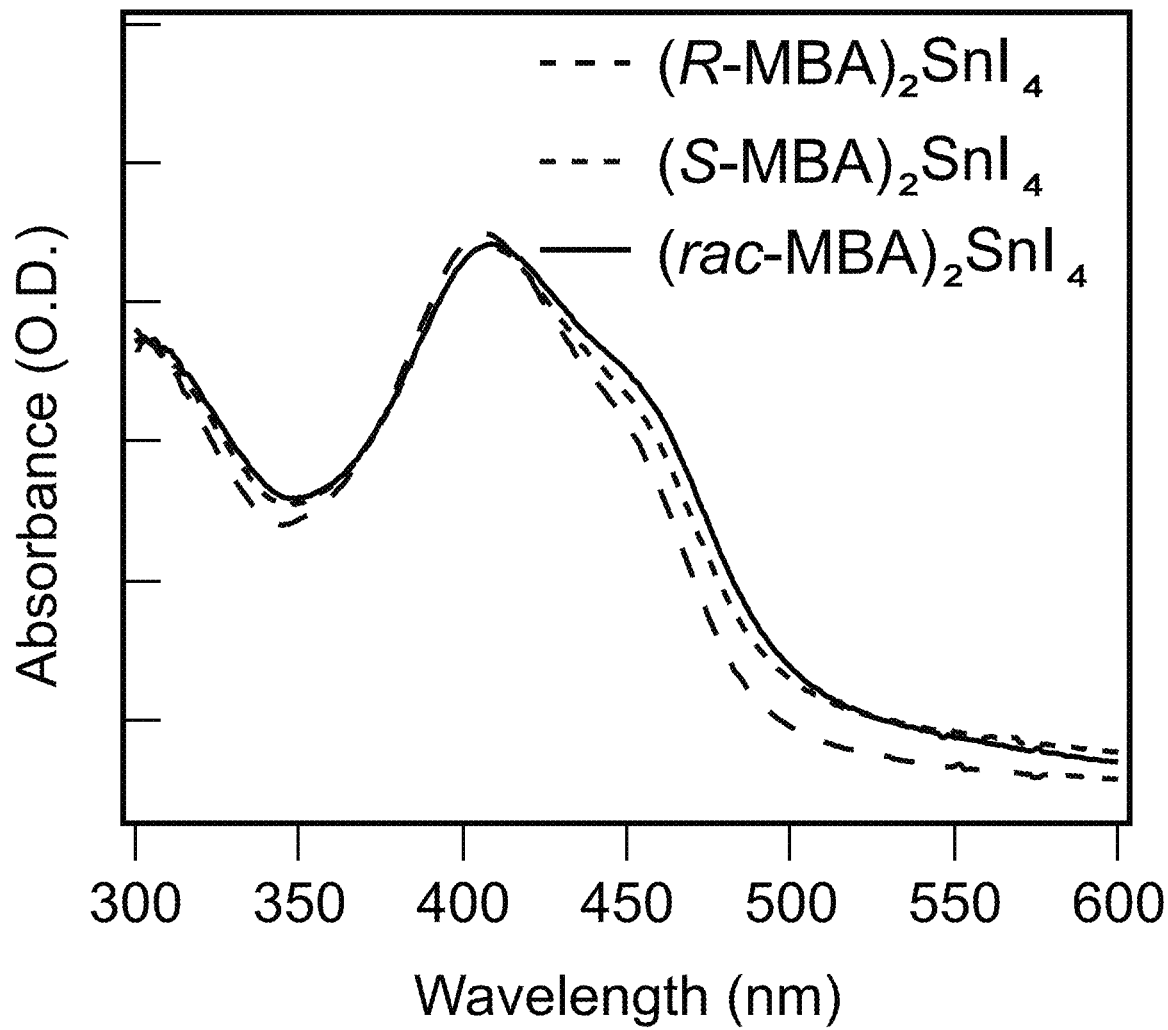

FIG. 19A illustrates linear absorption of (R-MBA)$_2$SnI$_4$, (S-MBA)$_2$SnI$_4$, and (rac-MBA)$_2$SnI$_4$ thin films, according to some embodiments of the present disclosure.

Figure 19B:
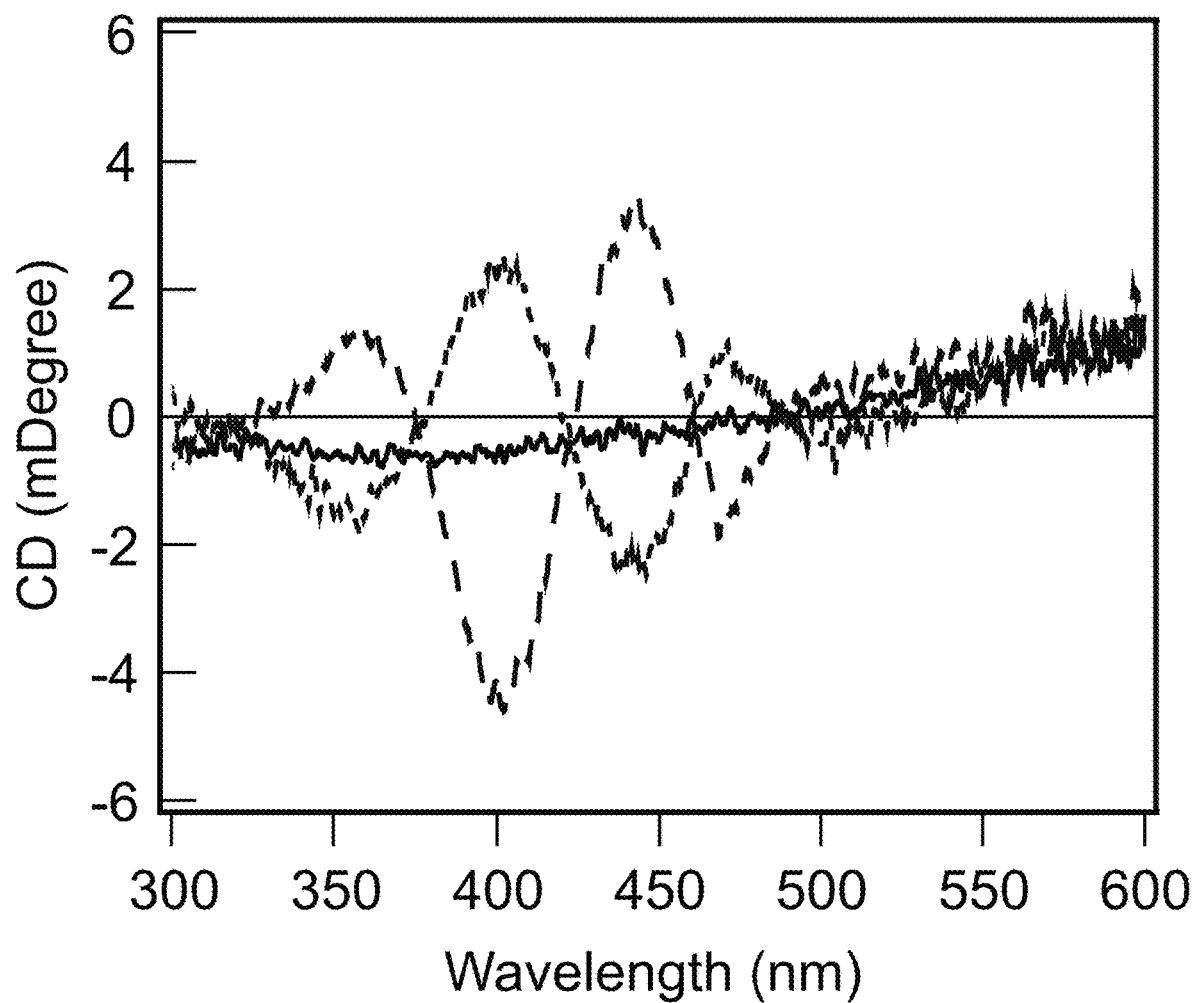

FIG. 19B illustrates circular dichroism (CD) spectra of (R-MBA)$_2$SnI$_4$, (S-MBA)$_2$SnI$_4$, and (rac-MBA)$_2$SnI$_4$ thin films, according to some embodiments of the present disclosure. CD spectra display derivative features at 300 to 500 nm, with R- and S-showing the opposite signs.

Figure 20A:
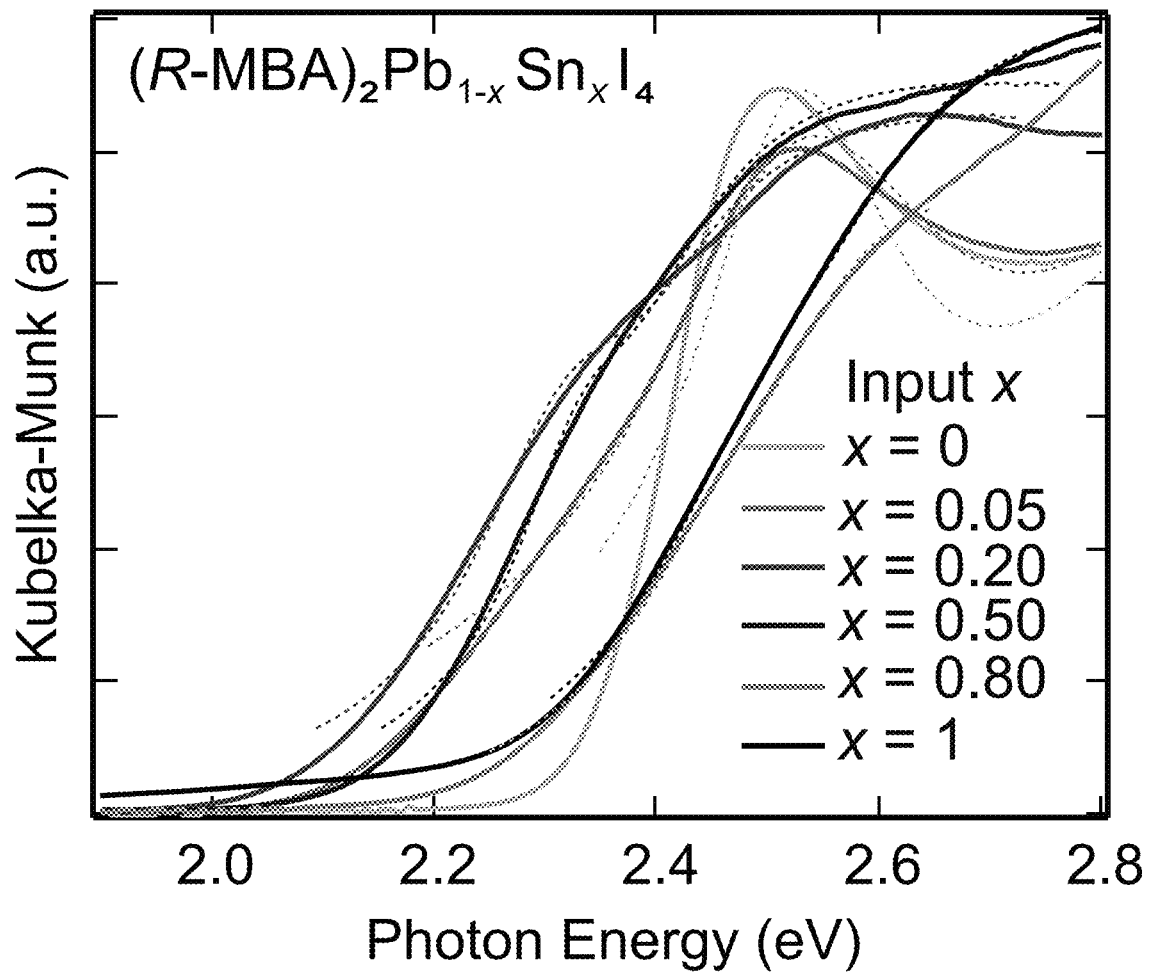

FIG. 20A illustrates, optical absorption of freshly-prepared crystalline samples of (R-MBA)$_2$Pb$_{1-x}$Sn$_x$I$_4$ (input x=0, 0.05, 0.20, 0.50, 0.80, 1), obtained from diffuse reflectance spectroscopy, according to some embodiments of the present disclosure.

Figure 20B:
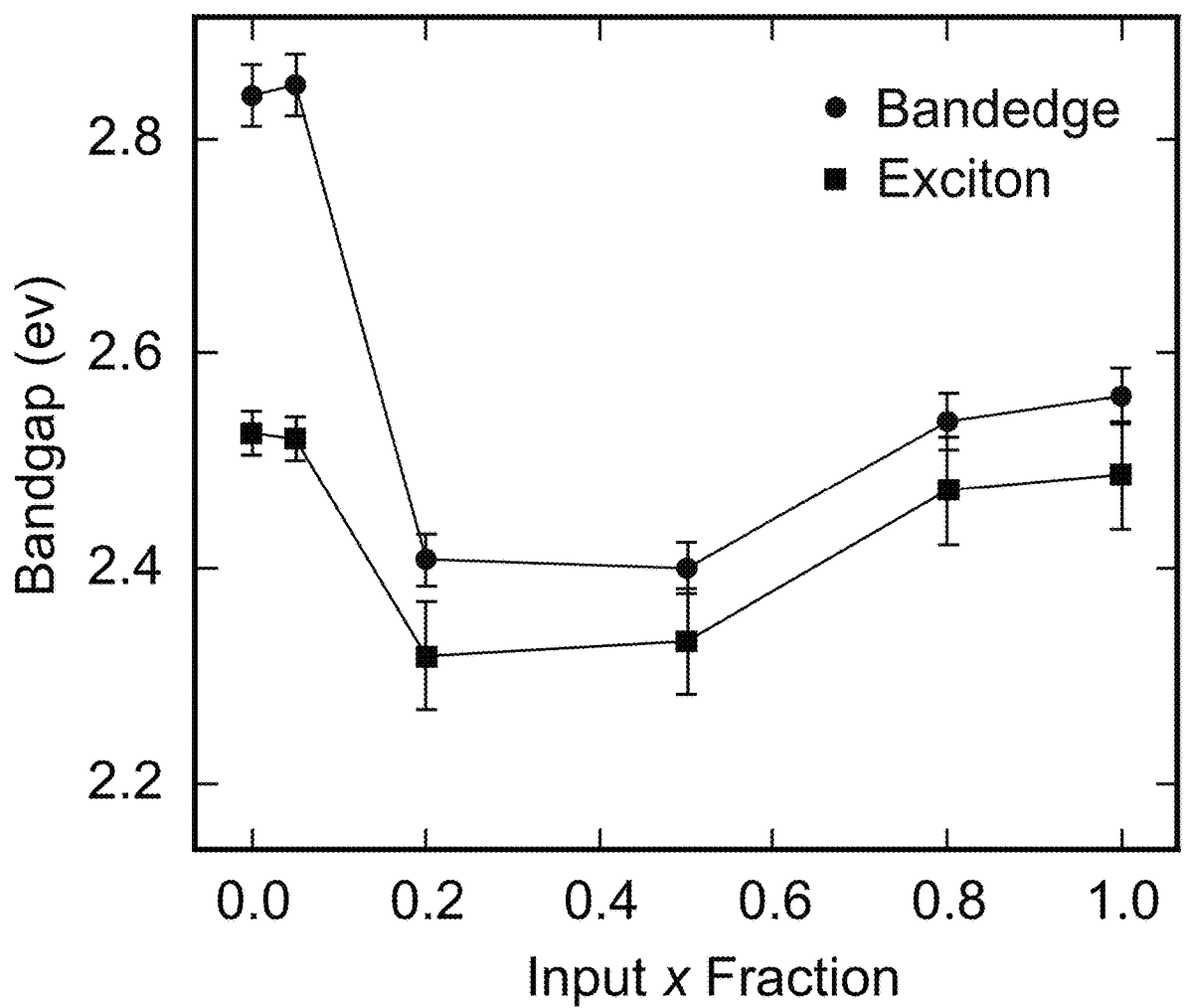

FIG. 20B illustrates optical bandgap of solid solution powders as a function of input Sn fraction, according to some embodiments of the present disclosure. The errors associated with optical bandgaps are extracted from the fitting of the absorption onset in (a).

Figure 21A:
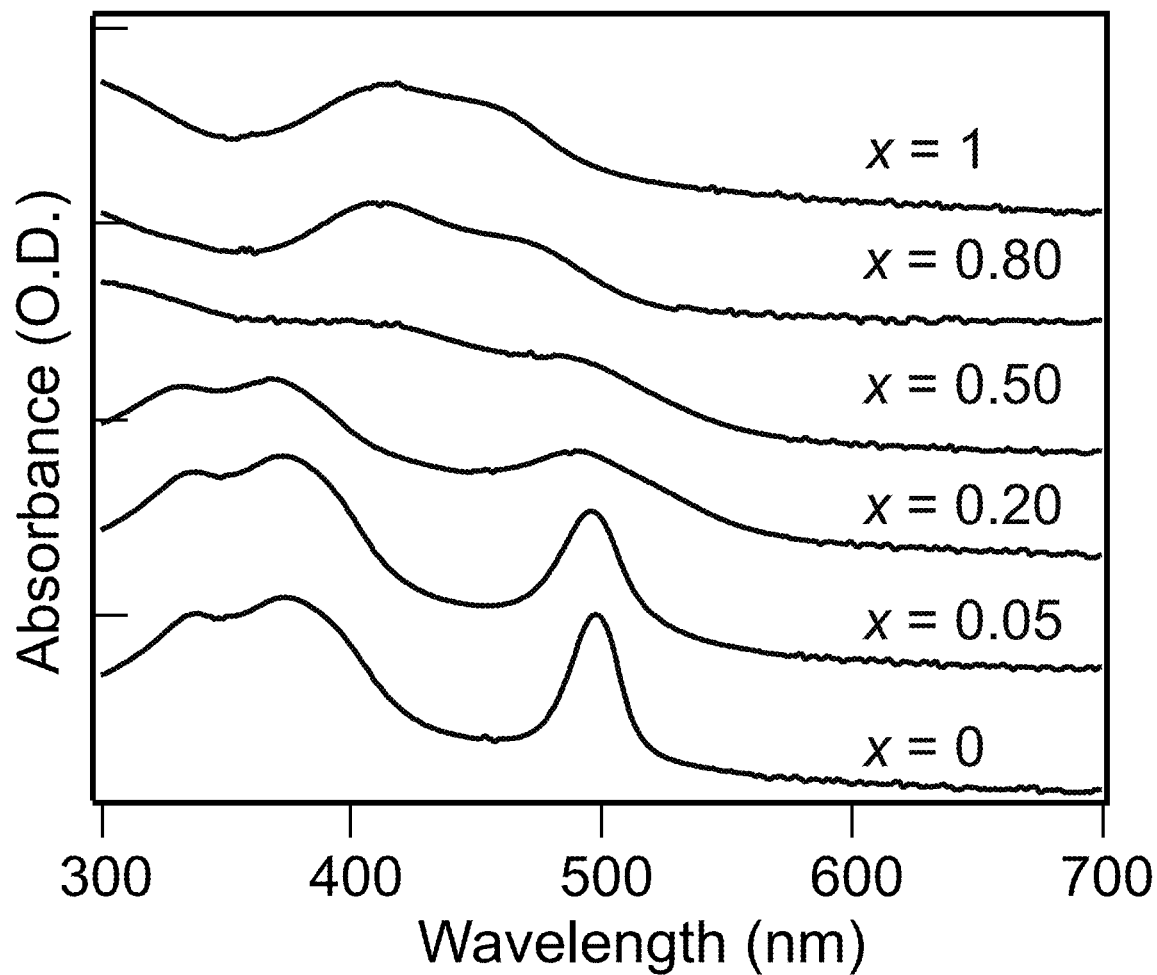

FIG. 21A illustrates linear absorption of (R-MBA)$_2$Pb$_{1-x}$Sn$_x$I$_4$ (x=0, 0.05, 0.20, 0.50, 0.80, 1) solid solution thin films, according to some embodiments of the present disclosure.

Figure 21B:
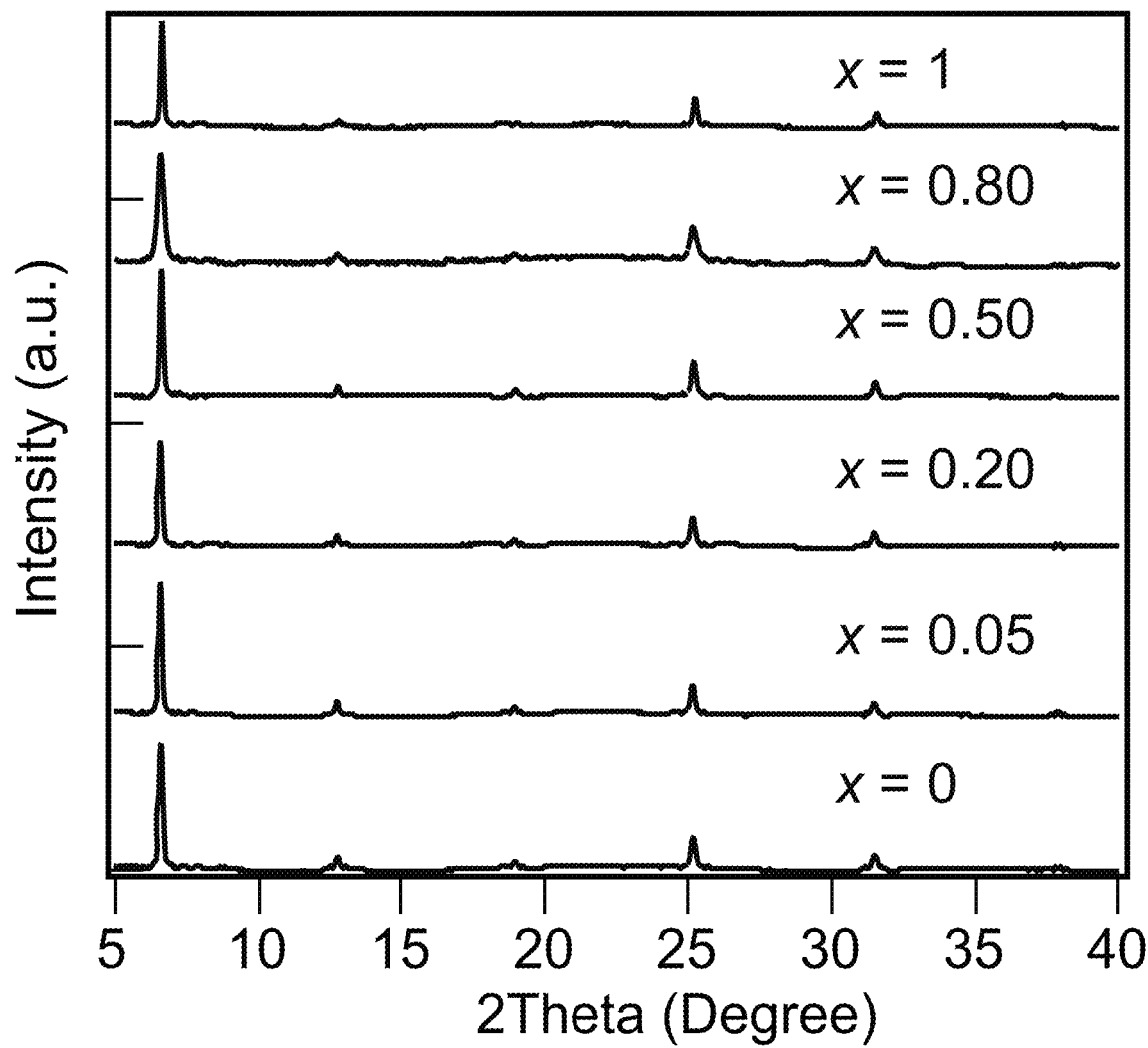

FIG. 21B illustrates and XRD of (R-MBA)$_2$Pb$_{1-x}$Sn$_x$I$_4$ (x=0, 0.05, 0.20, 0.50, 0.80, 1) solid solution thin films, according to some embodiments of the present disclosure.

Figure 22:
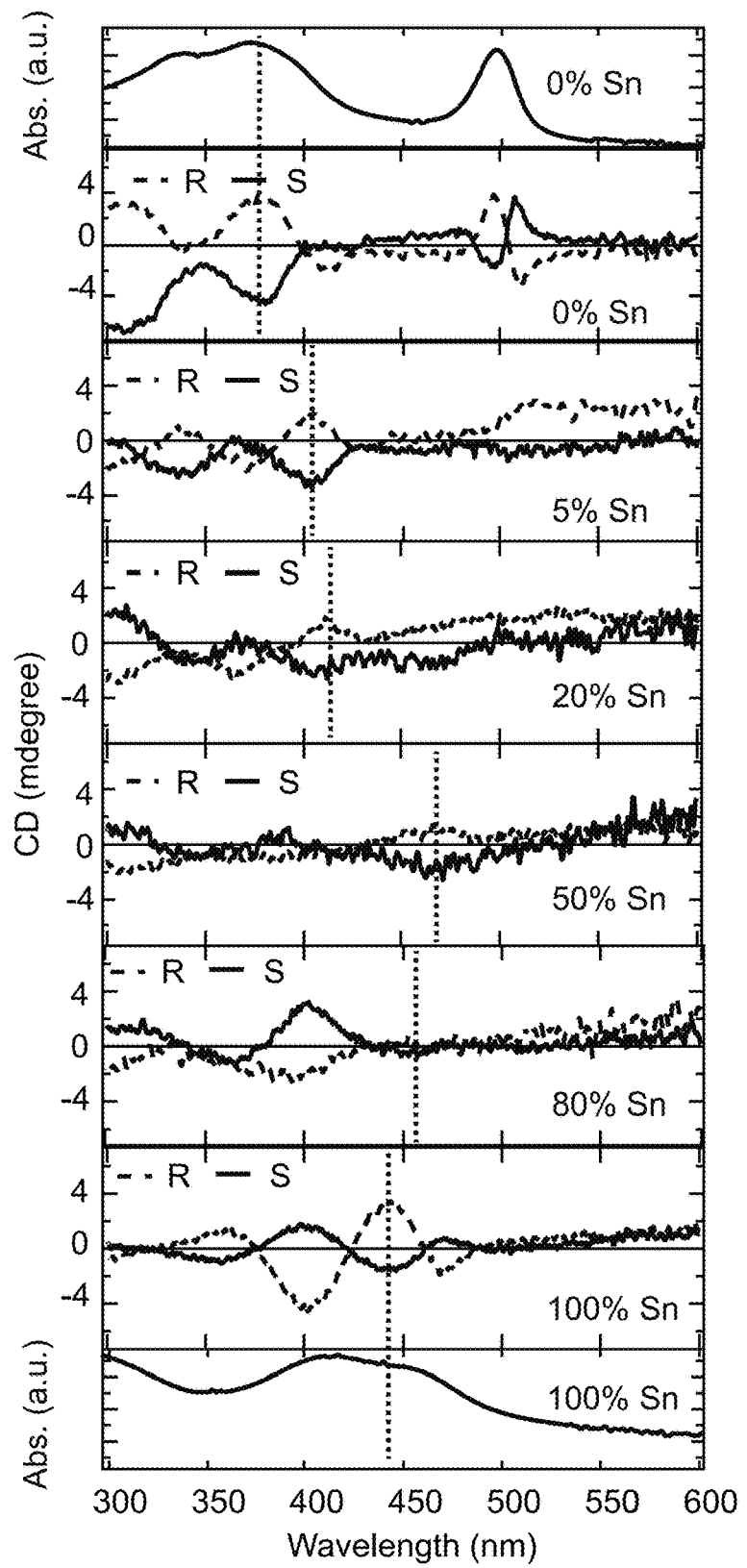

FIG. 22 illustrates CD spectra of (R-MBA)$_2$Pb$_{1-x}$Sn$_x$I$_4$ (x=0, 0.05, 0.20, 0.50, 0.80, 1) solid solution thin films (Blue: R-perovskite; Red: S-perovskite), overlapped with the linear absorption spectra of two ends, i.e. (MBA)$_2$PbI$_4$ and (MBA)$_2$SnI$_4$, on the top and bottom, respectively, according to some embodiments of the present disclosure. Orange dash lines indicate the shift of peaks.

Figure 23A:
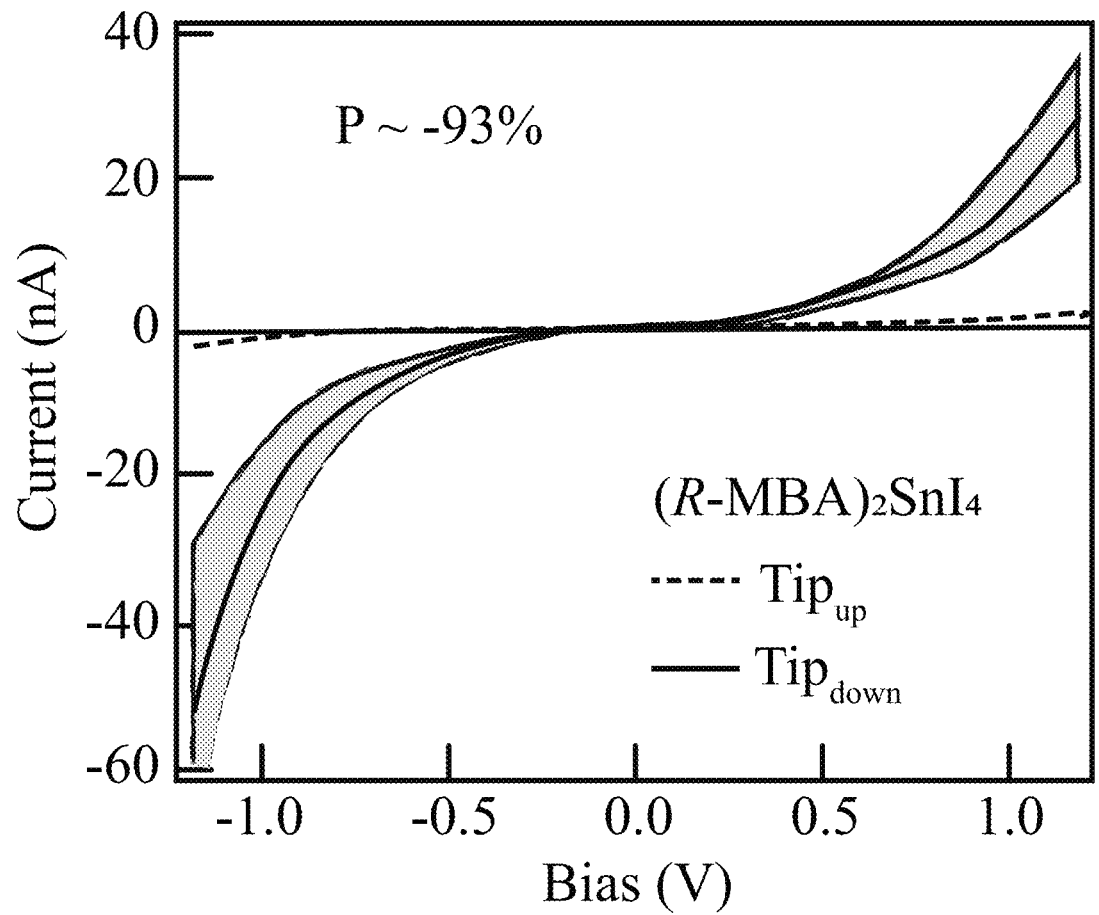

FIG. 23A illustrates room-temperature I-V curves obtained using the magnetic conductive-probe AFM technique of chiral 2D hybrid (R-MBA)$_2$SnI$_4$, according to some embodiments of the present disclosure. The J-V response for each 2D film was averaged over 100 scans at different points and the shaded region around the lines marks the 95% confidence limits for the average results.

Figure 23B:
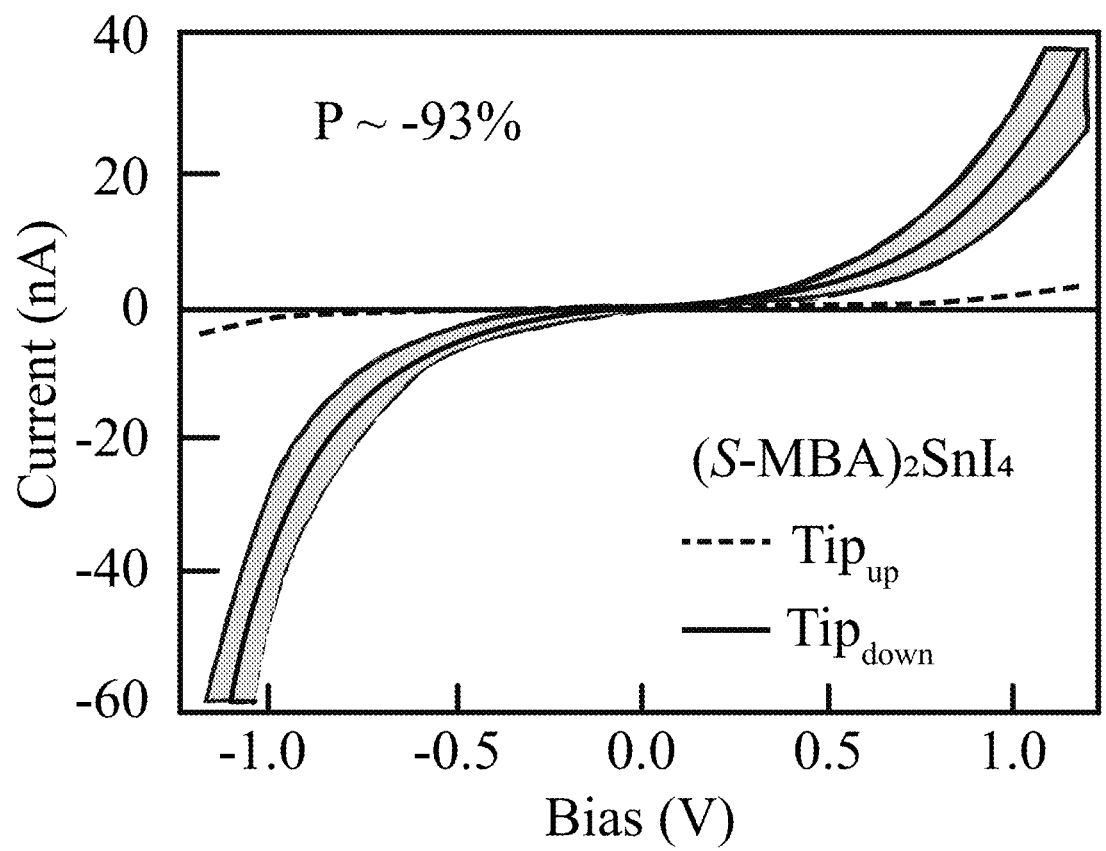

FIG. 23B illustrates room-temperature I-V curves obtained using the magnetic conductive-probe AFM technique of chiral (S-MBA)$_2$SnI$_4$ thin films (b, ~50-60 nm thick), according to some embodiments of the present disclosure.

| REFERENCE NUMBERS | |
|---|---|
| 100 | perovskite |
| 110 | A-cation |
| 120 | B-cation |
| 130 | X-anion |
| 300 | hybrid organic-inorganic perovskite |
| 310 | two-dimensional network |
| 320 | chiral molecule |
| 330 | chiral molecule layer |

DETAILED DESCRIPTION

The present disclosure may address one or more of the problems and deficiencies of the prior art discussed above. However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult to define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to ±20%, ±15%, ±10%, ±5%, or ±1% of a specific numeric value or target. In some embodiments of the present invention, the term "about" is used to indicate an uncertainty limit of less than or equal to ±1%, ±0.9%, ±0.8%, ±0.7%, ±0.6%, ±0.5%, ±0.4%, ±0.3%, ±0.2%, or ±0.1% of a specific numeric value or target.

Among other things, the present disclosure relates to ferromagnetic hybrid materials. For example, organic chiral ligands may be used to break the spin degeneracy of the metal halide lattice in metal halide perovskites and/or similar hybrid materials. This can then create a ground state of a single spin type that upon electronic doping via substitution into the metal lattice (e.g. tin to create holes) or by charge transfer doping (e.g. partial substitution of the chiral organic ligands with charge transfer ligands or pre oxidation of chiral ligands), which, as shown herein, can result in a material with a ferromagnetic ground state (i.e. a ferromagnet). The total magnetization of such a systems can also be manipulated via B site (see below) substitution with metals with net spin moments (e.g. Mn with 5/2 spin) in combination with the metal-based and/or ligand-based doping. In some embodiments of the present disclosure, the resultant low-dimensional, layered perovskite structure, having chiral organic molecule interlayers may have the physical properties and performance metrics of a spin filter. When the chiral organic molecule is R, this allows spin ½ electrons to transmit through the film. When the chiral organic is S, this allows spin −½ electrons to transmit through the film.

Figure 1A:
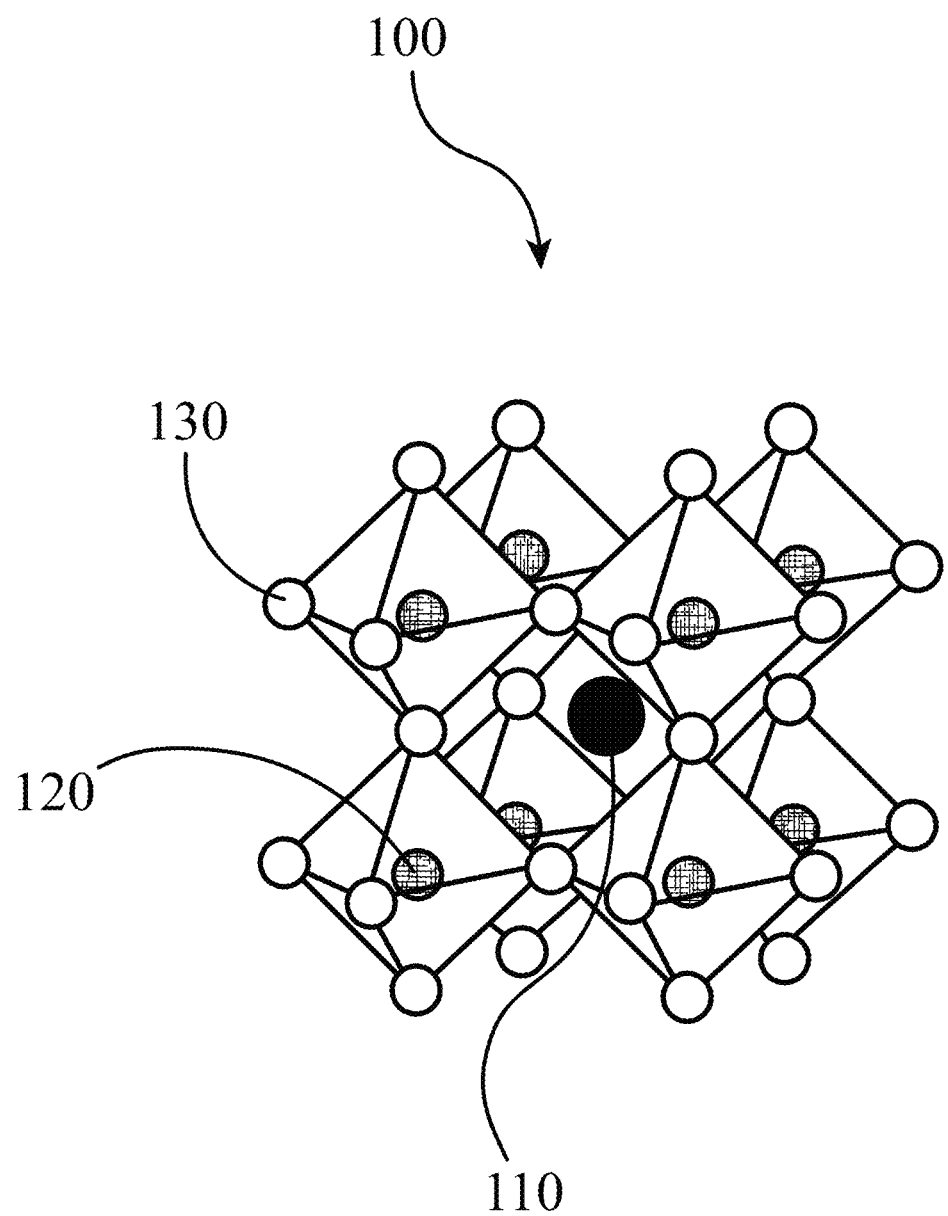
FIGS. 1A, 1B, and 1C illustrate a three-dimensional (3D) perovskite, according to some embodiments of the present disclosure.
Figure 1B:
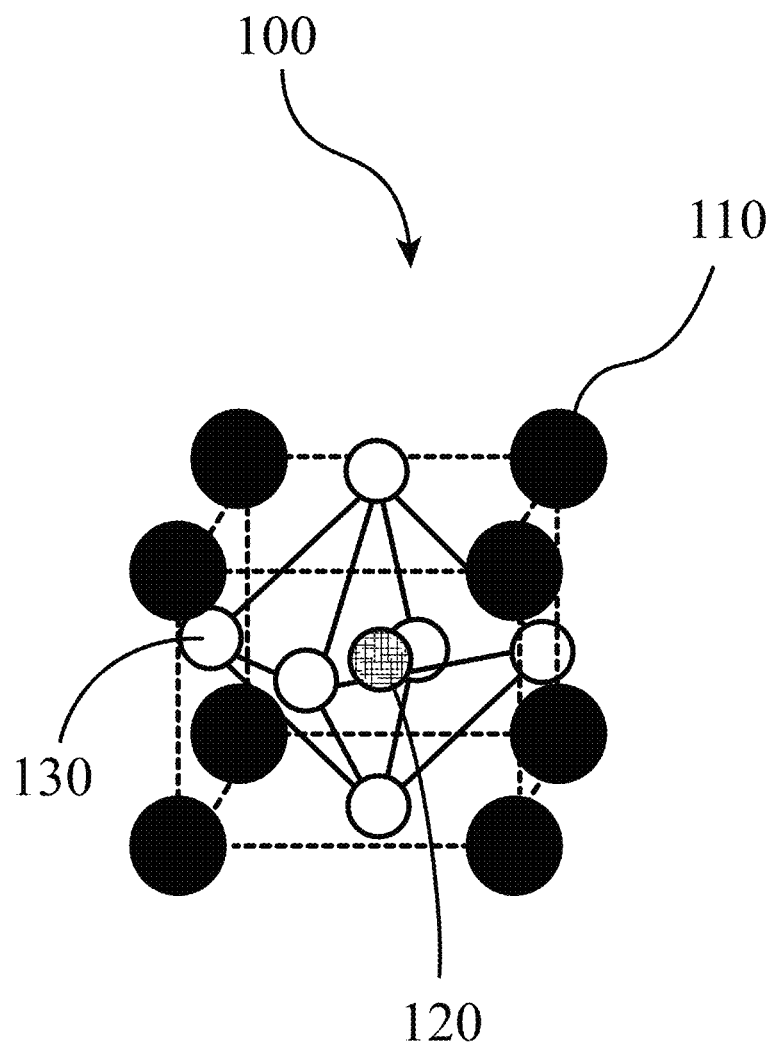
Figure 1C:
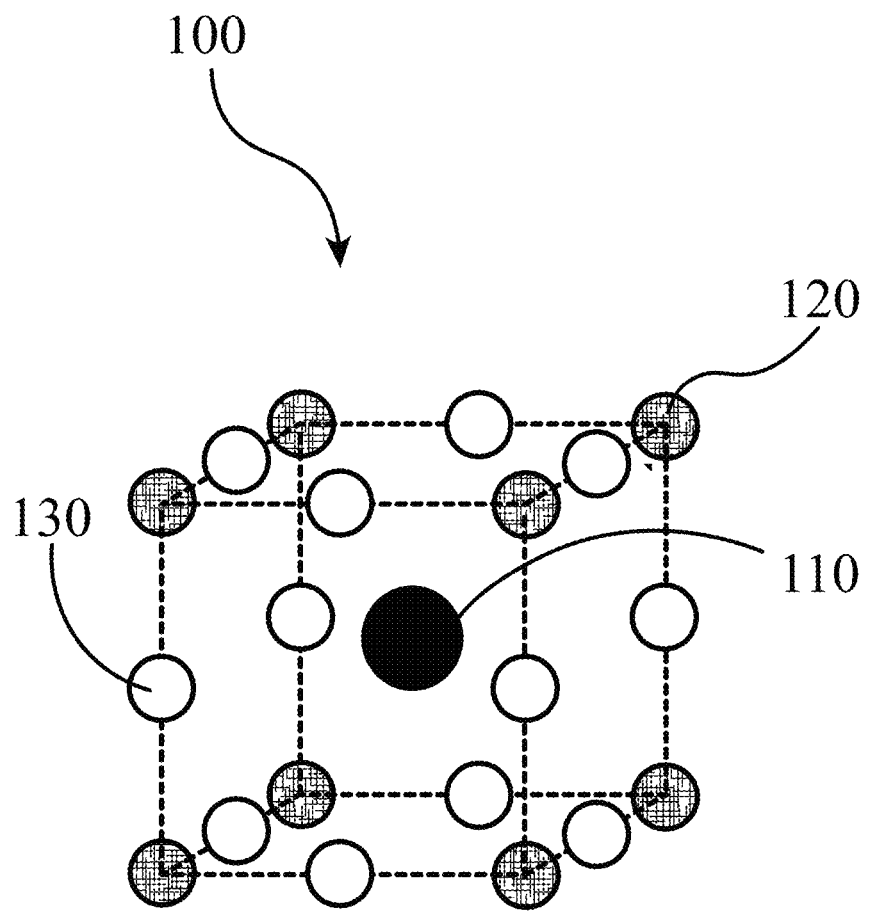

FIGS. 1A, 1B, and 1C illustrate that perovskites 100, for example halide perovskites, may organize into cubic crystalline structures with corner-sharing octahedra, as well as other crystalline structures such as tetragonal, hexagonal, and orthorhombic with either edge- or face-sharing octahedra, and may be described by the general formula $ABX_3$, where X (130) is an anion and A (110) and B (120) are cations, typically of different sizes (A typically larger than B). FIG. 1A illustrates that a perovskite 100 may be organized into eight octahedra surrounding a central A-cation 110, where each octahedra is formed by six X-anions 130 surrounding a central B-cation 120. FIG. 1B illustrates that a perovskite 100 may be visualized as a cubic unit cell, where the B-cation 120 is positioned at the center of the cube, an A-cation 110 is positioned at each corner of the cube, and an X-anion 130 is face-centered on each face of the cube. FIG. 1C illustrates that a perovskite 100 may also be visualized as a cubic unit cell, where the B-cation 120 resides at the eight corners of a cube, while the A-cation 110 is located at the center of the cube and with 12 X-anions 130 centrally located between B-cations 120 along each edge of the unit cell. For both unit cells illustrated in FIGS. 1B and 1C, the A-cations 110, the B-cations 120, and the X-anions 130 balance to the general formula $ABX_3$, after accounting for the fractions of each atom shared with neighboring unit cells. For example, referring to FIG. 1B, the single B-cation 120 atom is not shared with any of the neighboring unit cells. However, each of the six X-anions 130 is shared between two unit cells, and each of the eight A-cations 110 is shared between eight unit cells. So for the unit cell shown in FIG. 1B, the stoichiometry simplifies to B=1, A=8*0.124=1, and X=6*0.5=3, or $ABX_3$. Similarly, referring again to FIG. 1C, since the A-cation is centrally positioned, it is not shared with any of the unit cells neighbors. However, each of the 12 X-anions 130 is shared between four neighboring unit cells, and each of the eight B-cations 120 is shared between eight neighboring unit cells, resulting in A=1, B=8*0.125=1, and X=12*0.25=3, or $ABX_3$. Referring again to FIG. 1C, the X-anions 130 and the B-cations 120 are shown as aligned along an axis; e.g. where the angle at the X-anion 130 between two neighboring B-cations 120 is exactly 180 degrees, referred to herein as the tilt angle. However, a perovskite 100 may have a tilt angle not equal to 180 degrees. For example, some embodiments of the present disclosure may have a tilt angle between 153 and 180 degrees.

Typical inorganic perovskites include calcium titanium oxide (calcium titanate) minerals such as, for example, $CaTiO_3$ and $SrTiO_3$. In some embodiments of the present invention, the A-cation 110 may include a nitrogen-containing organic compound such as an alkyl ammonium compound. The B-cation 120 may include a metal and the X-anion 130 may include a halogen. Additional examples for the A-cation 110 include organic cations and/or inorganic cations, for example Cs, Rb, K, Na, Li, and/or Fr. Organic A-cations 110 may be an alkyl ammonium cation, for example a $C_{1-20}$ alkyl ammonium cation, a $C_{1-6}$ alkyl ammonium cation, a $C_{2-6}$ alkyl ammonium cation, a $C_{1-5}$ alkyl ammonium cation, a $C_{1-4}$ alkyl ammonium cation, a $C_{1-3}$ alkyl ammonium cation, a $C_{1-2}$ alkyl ammonium cation, and/or a $C_1$ alkyl ammonium cation. Further examples of organic A-cations 110 include methylammonium ($CH_3NH_3^+$), ethylammonium ($CH_3CH_2NH_3^+$), propylammonium ($CH_3CH_2CH_2NH_3^+$), butylammonium ($CH_3CH_2CH_2CH_2NH_3^+$), formamidinium ($NH_2CH=NH_2^+$), hydrazinium, acetylammonium, dimethylammonium, imidazolium, guanidinium and/or any other suitable nitrogen-containing or organic compound. In other examples, an A-cation 110 may include an alkylamine. Thus, an A-cation 110 may include an organic component with one or more amine groups. For example, an A-cation 110 may be an alkyl diamine halide such as formamidinium ($CH(NH_2)_2$). Thus, the A-cation 110 may include an organic constituent in combination with a nitrogen constituent. In some cases, the organic constituent may be an alkyl group such as straight-chain or branched saturated hydrocarbon group having from 1 to 20 carbon atoms. In some embodiments, an alkyl group may have from 1 to 6 carbon atoms. Examples of alkyl groups include methyl ($C_1$) ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like.

Examples of metal B-cations 120 include, for example, lead, tin, germanium, and or any other 2+ valence state metal that can charge-balance the perovskite 100. Further examples include transition metals in the 2+ state such as Mn, Mg, Zn, Cd, and/or lanthanides such as Eu. B-cations may also include elements in the 3+ valence state, as described below, including for example, Bi, La, and/or Y. Examples for X-anions 130 include halogens: e.g. fluorine, chlorine, bromine, iodine and/or astatine. In some cases, the perovskite halide may include more than one X-anion 130, for example pairs of halogens; chlorine and iodine, bromine and iodine, and/or any other suitable pairing of halogens. In other cases, the perovskite 100 may include two or more halogens of fluorine, chlorine, bromine, iodine, and/or astatine.

Thus, the A-cation 110, the B-cations 120, and X-anion 130 may be selected within the general formula of $ABX_3$ to produce a wide variety of perovskites 100, including, for example, methylammonium lead triiodide ($CH_3NH_3PbI_3$), and mixed halide perovskites such as $CH_3NH_3PbI_{3-x}Cl_x$ and $CH_3NH_3PbI_{3-x}Br_x$. Thus, a perovskite 100 may have more than one halogen element, where the various halogen elements are present in non-integer quantities; e.g. x is not equal to 1, 2, or 3. As described herein, the A-cation 110 of a perovskite 100, may include one or more A-cations, for example, one or more of cesium, FA, MA, etc. Similarly, the B-cation 120 of a perovskite 100, may include one or more B-cations, for example, one or more of lead, tin, germanium, etc. Similarly, the X-anion 130 of a perovskite 100 may include one or more anions, for example, one or more halogens. Any combination is possible provided that the charges balance.

For example, a perovskite having the basic crystal structure illustrated in FIG. 1A, in at least one of a cubic, orthorhombic, and/or tetragonal structure, may have other compositions resulting from the combination of the cations having various valence states in addition to the 2+ state and/or 1+ state described above for lead and alkyl ammonium cations; e.g. compositions other than $AB^{2+}X_3$ (where A is one or more cations, or for a mixed perovskite where A is two or more cations). Thus, the methods described herein may be utilized to create novel mixed cation materials having the composition of a double perovskite (elpasolites), $A_2B^{1+}B^{3+}X_6$, with an example of such a composition being $Cs_2BiAgCl_6$ and $Cs_2CuBiI_6$. Another example of a composition covered within the scope of the present disclosure is described by $A_2B^{4+}X_6$, for example $Cs_2PbI_6$ and $Cs_2SnI_6$. Yet another example is described by $A_3B_2^{3+}X_9$, for example $Cs_3Sb_2I_9$. For each of these examples, A is one or more cations, or for a mixed perovskite, A is two or more cations.

Figure 2:
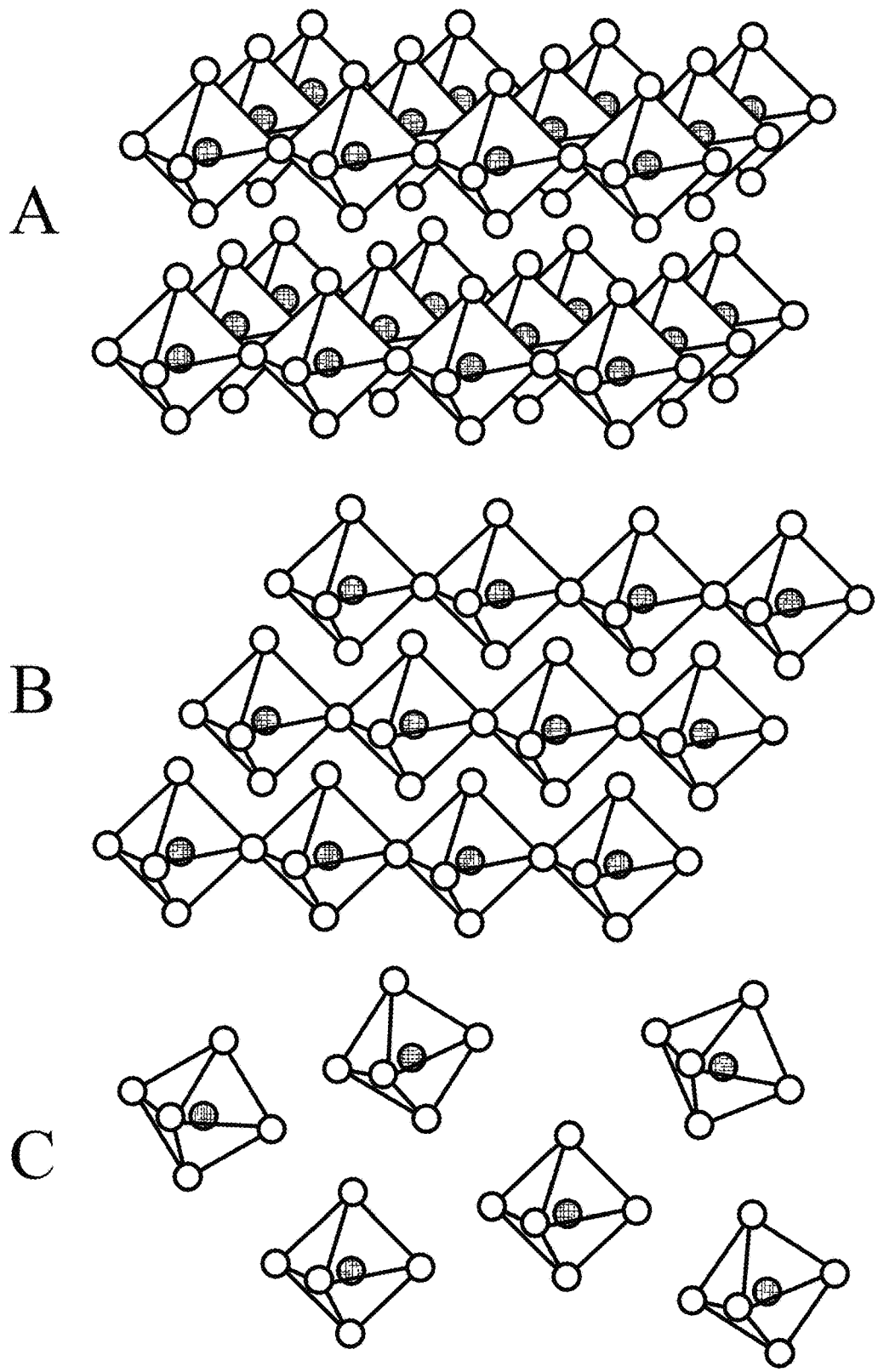
FIG. 2, Panels A, B, and C illustrate a two-dimensional (2D) perovskite, a one-dimensional (1D) perovskite, and a zero-dimensional (0D) perovskite, respectively, according to some embodiments of the present disclosure.

In addition, perovskite halides, like other organic-inorganic perovskites, can form a three-dimensional (3D) network, a two-dimensional (2D) network, a one-dimensional (1D) network and/or a zero-dimensional (0D) network, possessing the same unit structure. A perovskite's 3D network is illustrated in FIGS. 1A, 1B, and 1C. FIG. 2 illustrates a 2D perovskite network, a 1D perovskite network, and a 0D perovskite network, in Panels A, B, and C, respectively. As described above, a 3D perovskite may adopt a general chemical formula of $ABX_3$, in which the A-cation may be a monovalent cation (e.g. methylammonium and/or formamidinium $CH(NH_2)_2^+$), the B-cation may be a divalent cation (e.g. $Pb^{2+}$ and/or $Sn^{2+}$), and the X-anion may be a halide anion ($I^-$, $Br^-$, and/or $C_1^-$). In this formula, the 3D network of perovskites may be constructed by linking all corner sharing $BX_6$ octahedra, with the A-cation filling the space between eight octahedral unit cells to balance the crystal charge.

Referring to Panel A of FIG. 2, through the chemically accomplished dimensional reduction of the 3D crystal lattice, 2D perovskites, $(A')_m(A)_{n-1}B_nX_{3n+1}$, may adopt a new structural and compositional dimension, A' (not shown), where monovalent (m=2) or divalent (m=1) cations can intercalate between the X-anions of the 2D perovskite sheets. Referring to Panel B of FIG. 2, 1D perovskites are constructed by $BX_6$ octahedral chained segments spatially isolated from each other by surrounding bulky organic cations (not shown), leading to bulk assemblies of paralleled octahedral chains. Referring to Panel C of FIG. 2, typically, the 0D perovskites are consisted of isolated inorganic octahedral clusters and surrounded by small cations (not shown) which are connected via hydrogen bonding.

Figure 3:
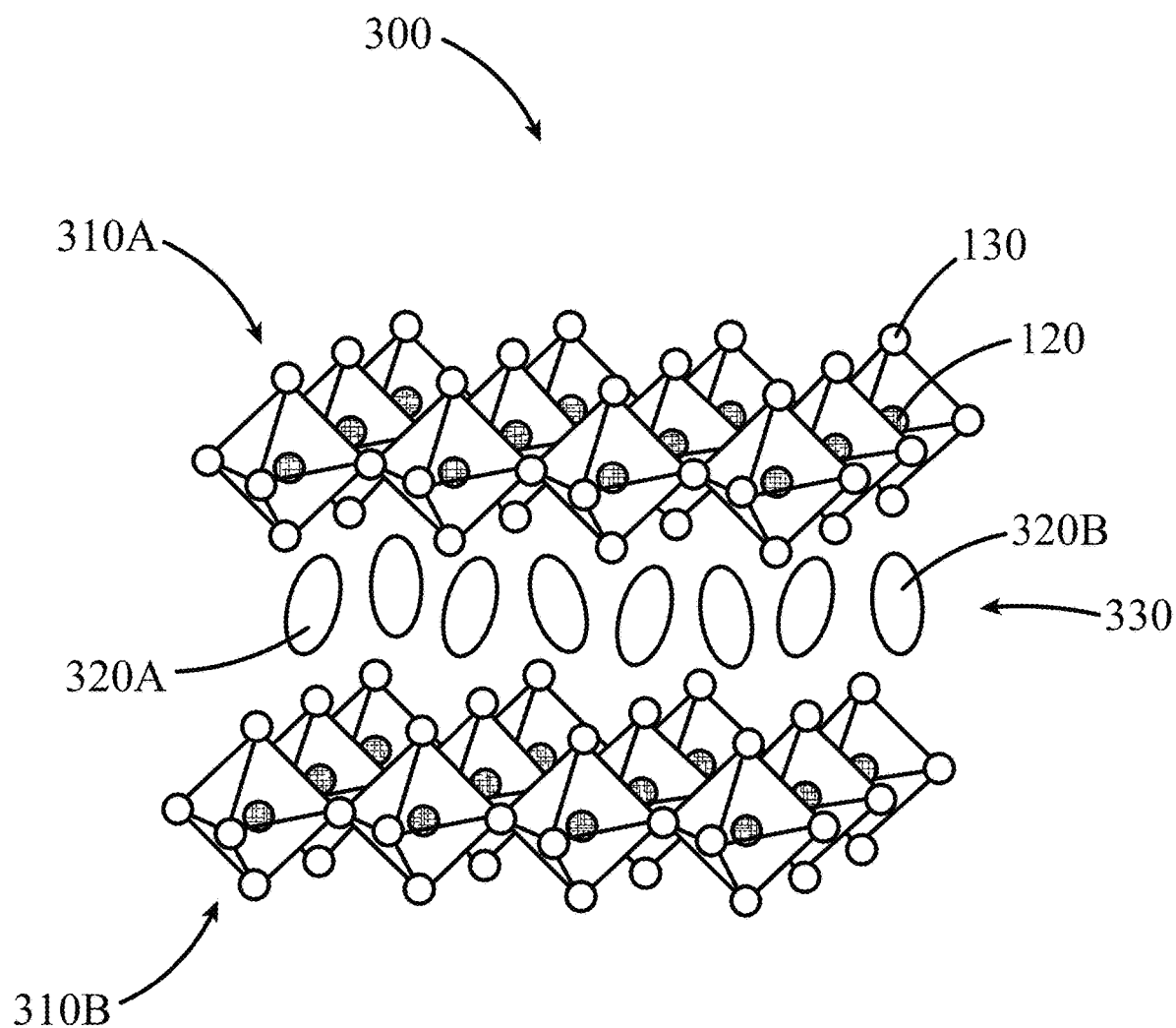
FIG. 3 illustrates an example of a hybrid organic-inorganic perovskite (HOIP), according to some embodiments of the present disclosure.

FIG. 3 illustrates an example of a hybrid organic-inorganic perovskite (HOIP) 300, according to some embodiments of the present disclosure. The HOIP 300 includes a first two-dimensional network 310A and a second two-dimensional network 310B, both constructed of two-dimensional sheets made of X-anions 130 and B-cations 120. Positioned between the first two-dimensional network 310A and the second two-dimensional network 310B is a chiral molecule layer 330 constructed of a plurality of chiral molecules 320, equivalent to A' in the formula, $(A')_m(A)_{n-1}B_nX_{3n+1}$, described above for Panel A of FIG. 2. When n=1 and m=2, the equation reduces to $A'_2BX_4$. When A' is a chiral molecule, either R or S, the HOIP 300 can possess a ferromagnetic ground state, as shown below.

In some embodiments of the present disclosure, the X-anion 130 of a HOIP 300 may include at least one halogen, including fluorine, chlorine, bromine, and/or iodine. In some embodiments of the present disclosure, the B-cation 120 of a HOIP 300 may include at least one Group 14 element, including at least one of lead and/or tin. In some embodiments of the present disclosure, the A'-cation, i.e. the chiral molecule 130, may include at least one of methylbenzylammonium (MBA), β-methylphenethylammonium, 1-methyl-3-phenylpropylammonium, 4-methoxy-α-methylbenzylammonium, 4-fluoro-α-methylbenzylammonium, 4-bromo-α-methylbenzylammonium, 2-amino-5-methylhexane, and/or alanine. These examples of chiral molecules 130 are shown in order as listed above in Scheme 1 below. The R- and S-MBA are both illustrated, whereas the R forms are only illustrated for the other molecules.

Scheme 1

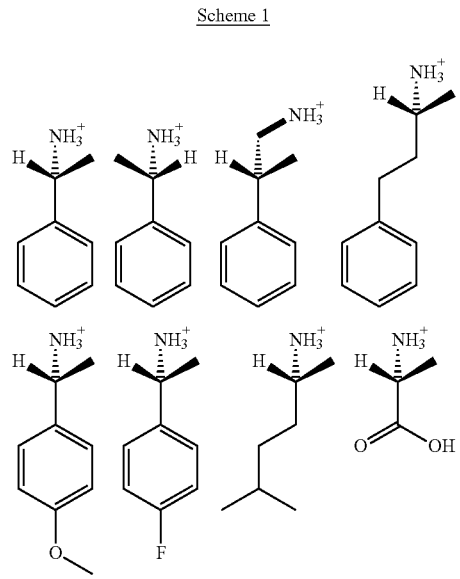

The examples of chiral molecules 130 shown in Scheme 1 can be generalized to the following three structures,

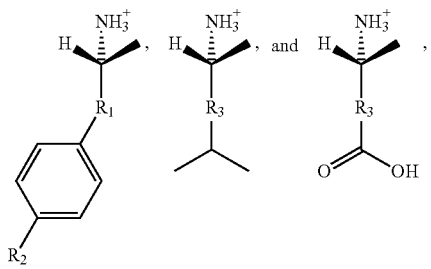

where $R_1$ includes a bond, a carbon atom, and/or a carbon chain. In some embodiments of the present disclosure, $R_1$ may include a carbon chain having between 2 and 5 carbon atoms, where the carbon chain may be saturated or unsaturated. In some embodiments of the present disclosure, $R_2$ may include a hydrogen atom, a halogen atom, a carboxylic acid group, an alkoxy group (e.g. methoxy), and/or a hydrocarbon chain having between 2 and 5 carbon atoms, where the carbon chain may be saturated or unsaturated. In some embodiments of the present disclosure, $R_3$ may include a carbon chain having between 2 and 5 carbon atoms, where the carbon chain may be saturated or unsaturated. In some embodiments of the present disclosure, a chiral molecule may include a naphthalene group instead of a single benzene ring, as shown below

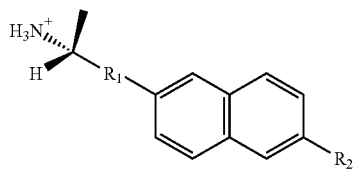

where $R_1$ and $R_2$ may be as defined above for examples of chiral molecules that include a single benzene ring.

In some embodiments of the present disclosure, a HOIP 300 as described herein may be configured to operate as a component of a spin filter, a spin polarized LED, a spin polarized laser, an op spin-valve, a spin-diode, a spin-transistor, a chiral-light detector, a switchable optical memory device (e.g. a chiral organic which would be UV or field addressable to change the molecular conformation and handedness and thus the spintronic optical and electronic [i.e. magnetic properties] and associated type of device one might be able to make with that functionality), a polarization selective optical multiplexor, an ultrafast modulator, and/or similar device based on ferromagnet or multiferroic material functionality based on these types of HOIP materials.

Among other things, the present disclosure relates to controlling spin-transport within 2D-layered chiral Pb-I perovskite HOIP systems. Spin-polarization of charge-transport through the chiral perovskites is demonstrated by showing that the injected current is preferential to one of the spin-states and depends upon the handedness of the incorporated chiral organic molecules; thus, the hybrid chiral system acts as a spin-filter. It is demonstrated herein that by tuning the organic component in the HOIP system to produce a highly-oriented 2D chiral perovskite thin film, vertical charge transport is strongly spin-dependent. Since the exemplary system described herein is composed of multilayer chiral organic ligands embedded in an inorganic sub-lattice, it is conceptionally different from previous reports of the chiral induced spin selectivity (CISS) effect. These materials were then used to produce spin-valves having a single ferromagnetic (FM) spin injector, rather than two FM electrodes as in more traditional spin-valve devices. The successful demonstration of the high spin-selectivity in such multilayer hybrid systems significantly expands the application of the CISS effect.

Figure 4A:
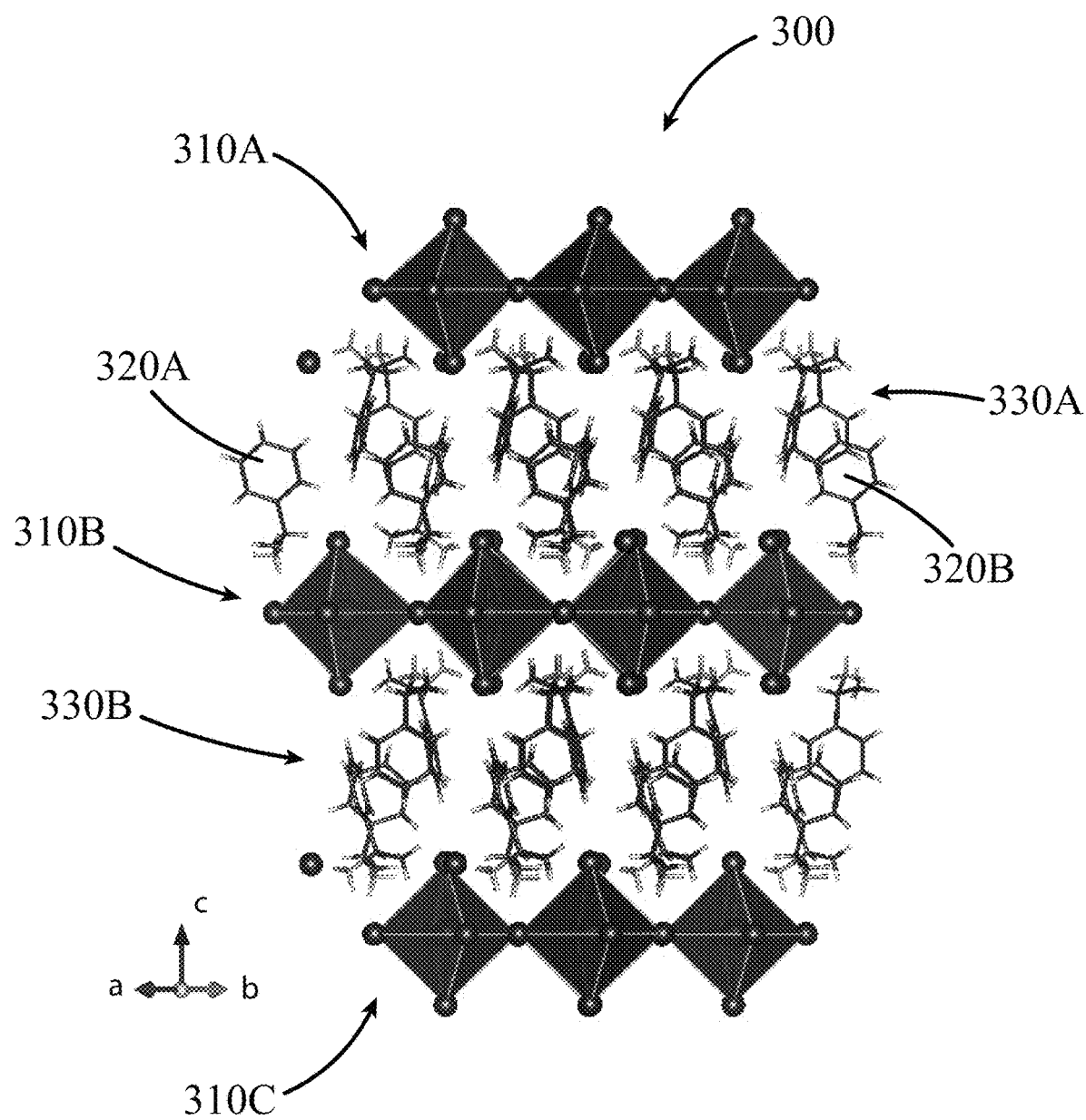
FIGS. 4A-4D illustrate structure and crystallographic orientation characterization of hybrid organic-inorganic perovskite (HOIP) crystals, according to some embodiments of the present disclosure.

Regarding the synthesis and photophysics of chiral 2D perovskites, FIG. 4A illustrates a chiral aromatic amine induced chirality in 2D-layered lead halide perovskites. In this example, two chiral molecule layers (330A and 330B) of chiral molecules (only two called out; 320A and 320B) of methylbenzylammonium (MBA) molecules are positioned between three layers of two-dimensional networks (310A, 310B, and 310C) of $PbI_4$. So, in this example, a hybrid organic-inorganic perovskite 300 is formed, $A_2BX_4$, of $MBA_2PbX_4$.

Figure 4B:
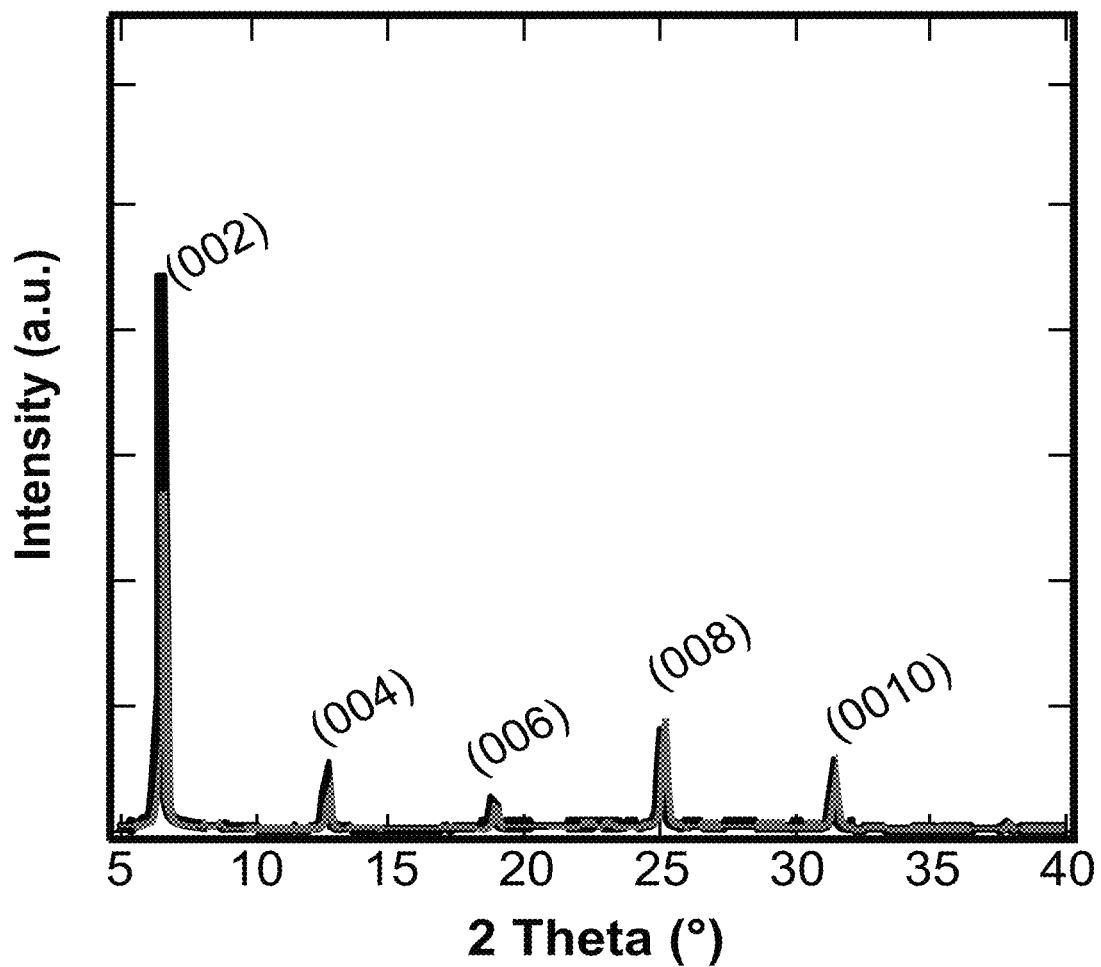
Figure 4C:
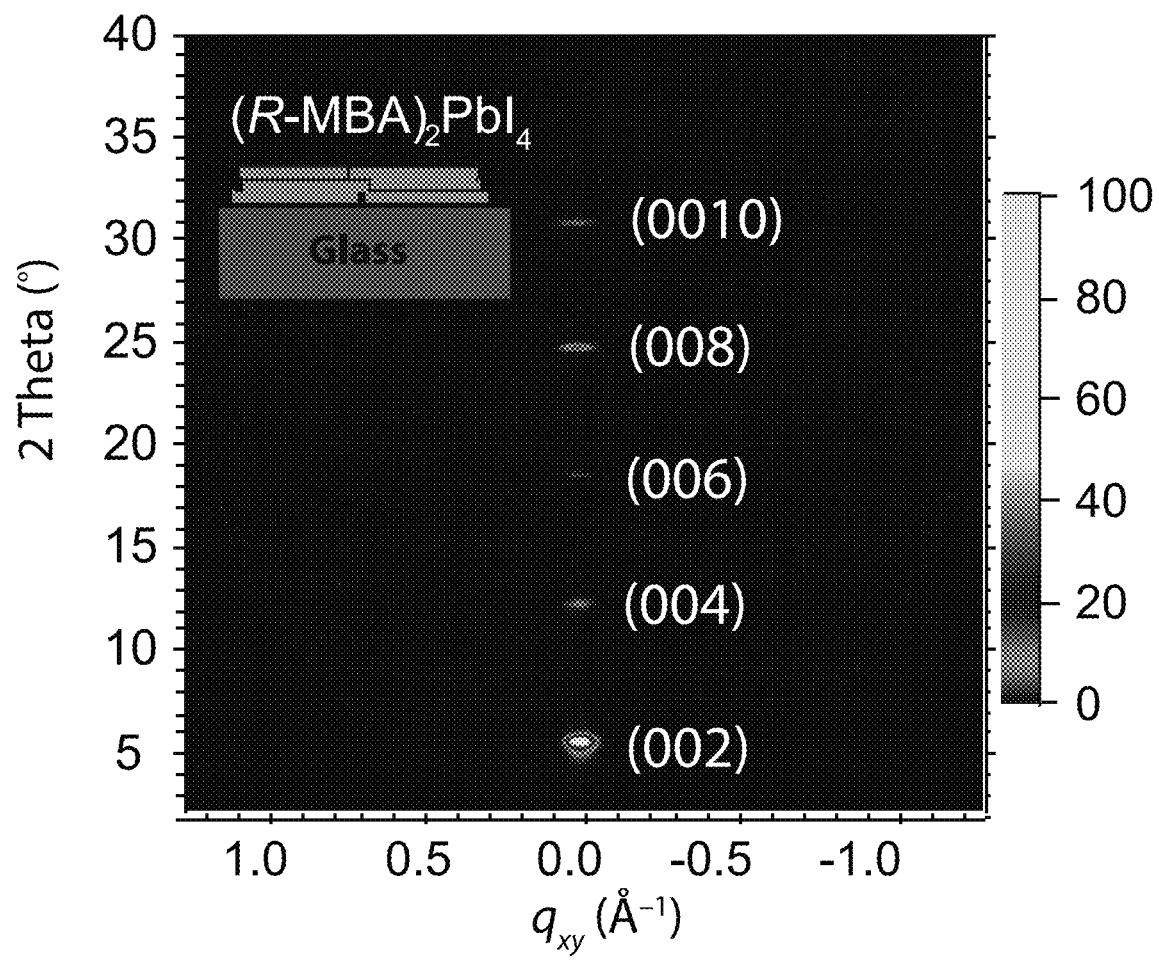
Figure 4D:
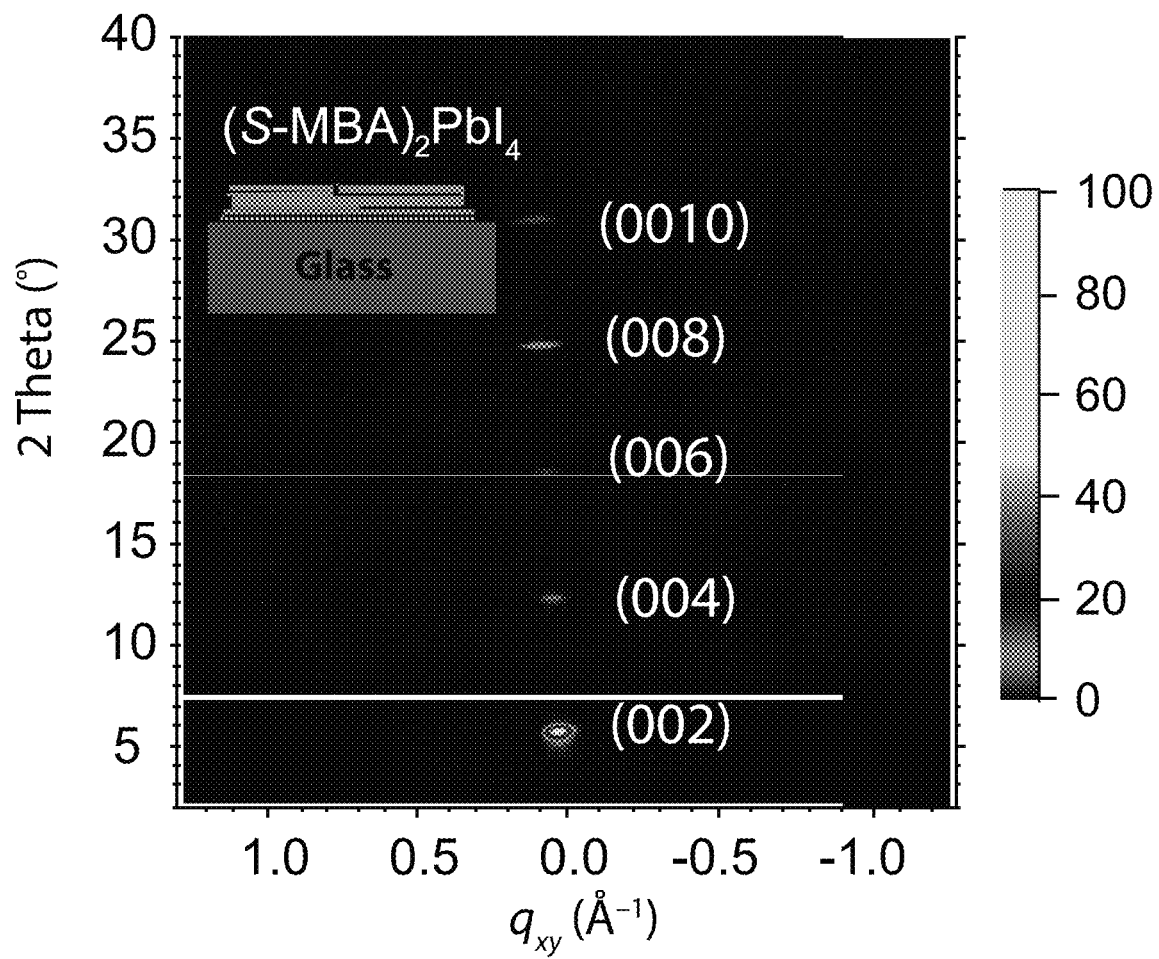
Figure 5A:
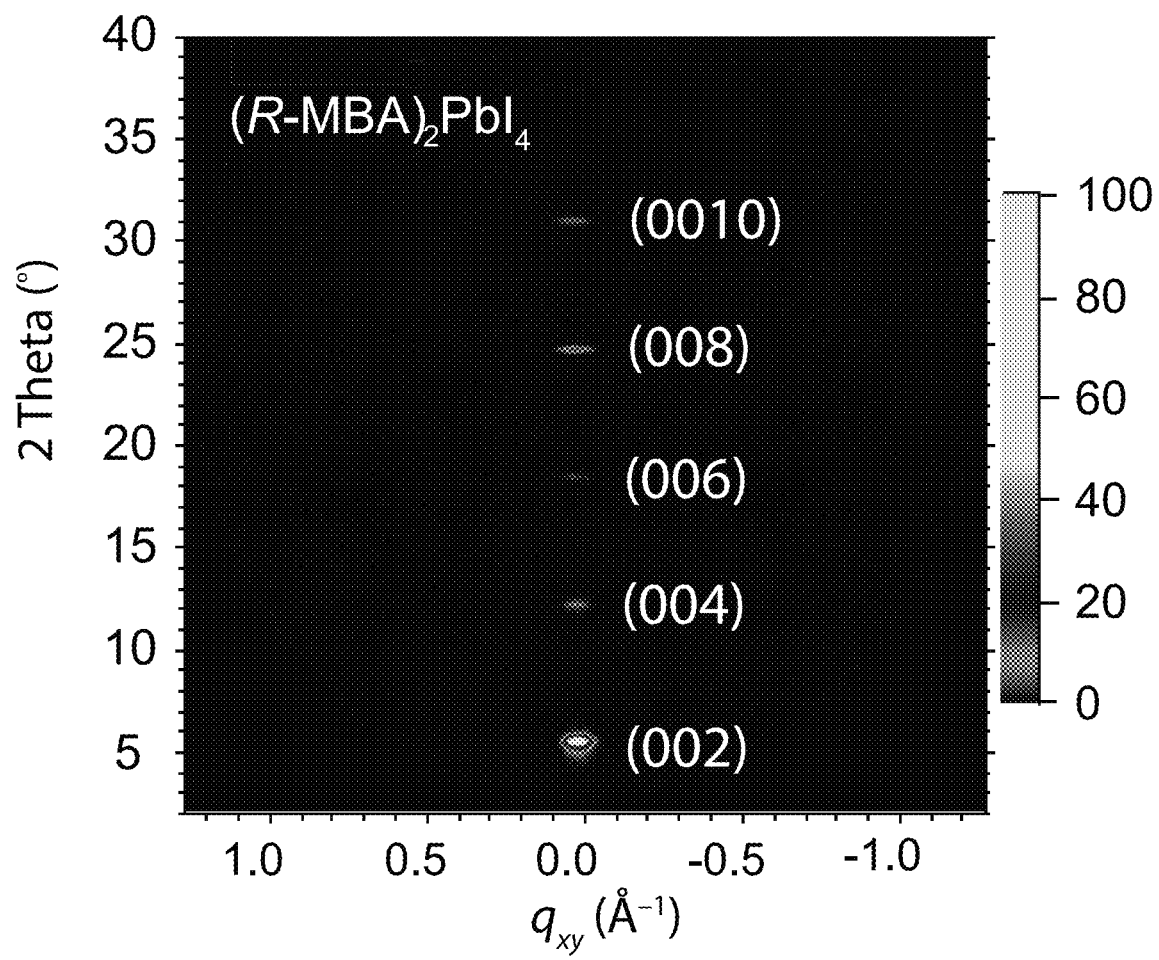
FIGS. 5A-5D illustrate XRD patterns for different 2D perovskite thin films, according to some embodiments of the present disclosure.
Figure 5B:
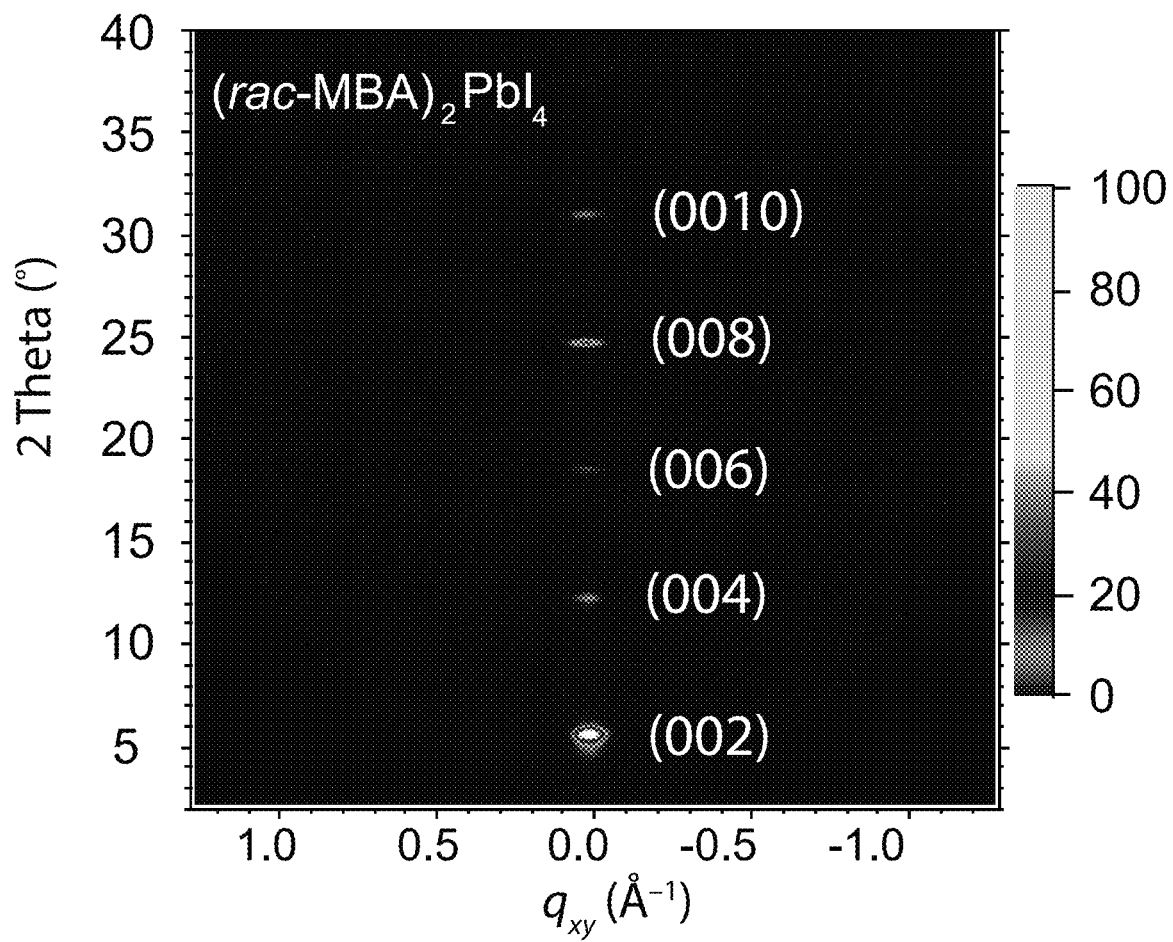
Figure 5C:
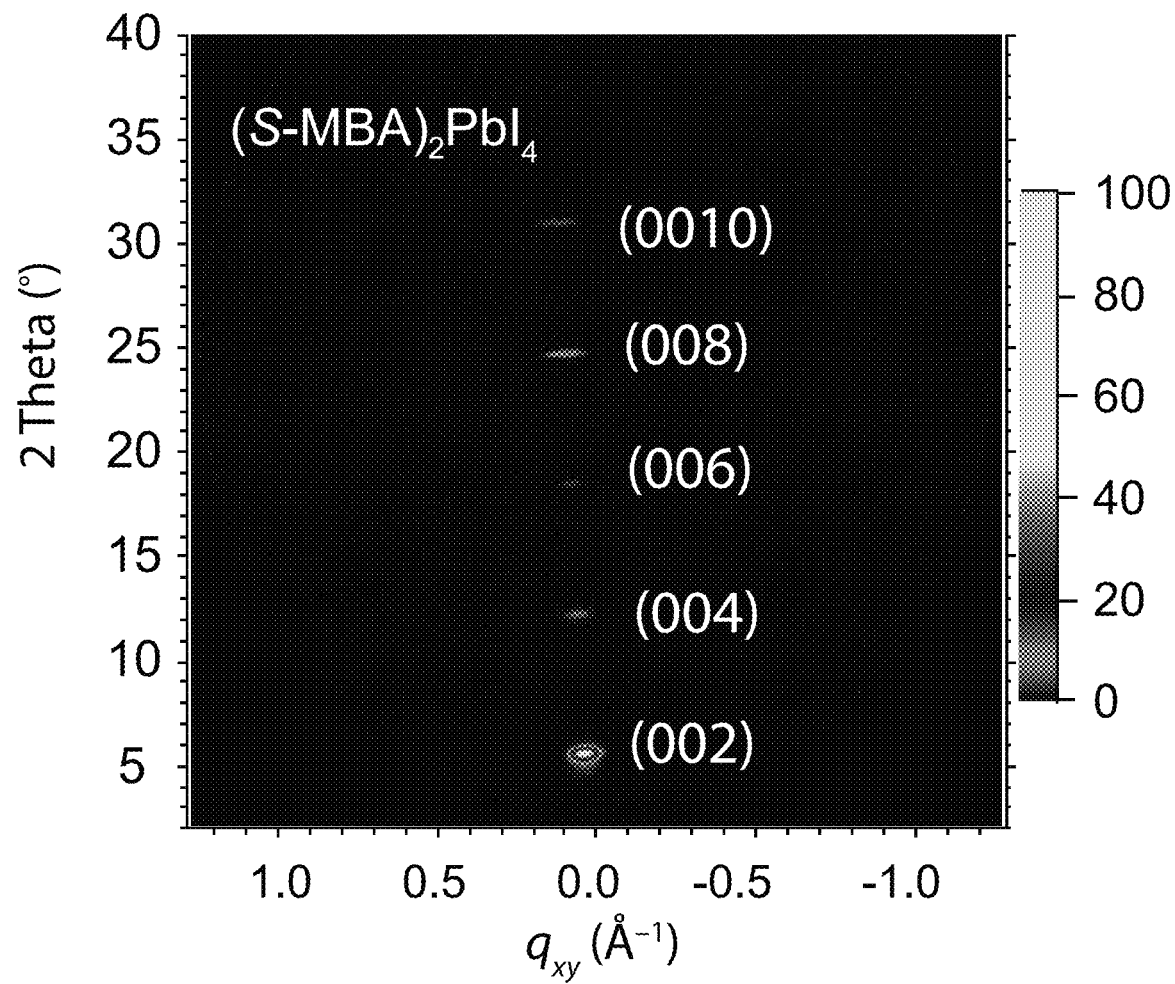
Figure 5D:
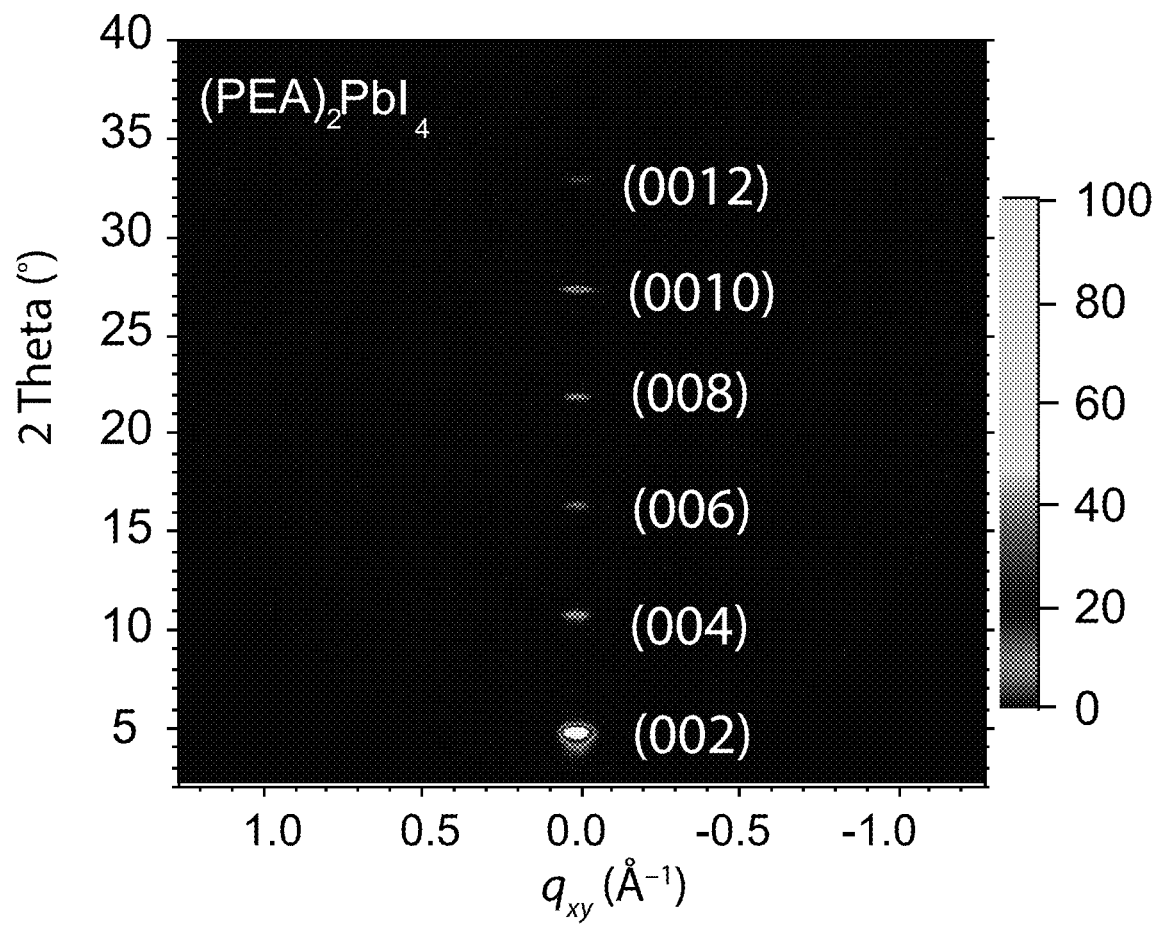

Single crystals of 2D chiral perovskite, (R/S/rac-) methylbenzylammonium lead iodide $(R/S/rac-MBA)_2PbI_4$ were synthesized as described herein. Polycrystalline thin films of the chiral perovskite were subsequently prepared by spin casting a DMF solution of the corresponding single crystals. X-ray diffraction data (XRD) show that in these thin films the 2D perovskite layers are highly oriented parallel to the substrate, with only (0 0 2l) peaks observed (see FIG. 4B). Note that the crystallinity of both systems, $(R-$ or $S-MBA)_2$ $PbI_4$, appears to be comparable, with no additional impurity peaks being detected. The degree of crystallographic orientation was further confirmed by 2D XRD measurements (see FIGS. 4C and 4D). Intense and sharp Bragg spots are observed in the $(R-$ or $S-MBA)_2PbI_4$ films that indicates highly oriented crystal grains. The Bragg spots can be assigned to the diffraction from (0 0 2l) peaks, consistent with 1D XRD results. The $(rac-MBA)_2PbI_4$ and $PEA_2PbI_4$ films also display similar 2D XRD patterns (see FIGS. 5A-5D), suggesting a highly oriented crystal structure in all of the resulting thin films studied here.

Figure 6A:
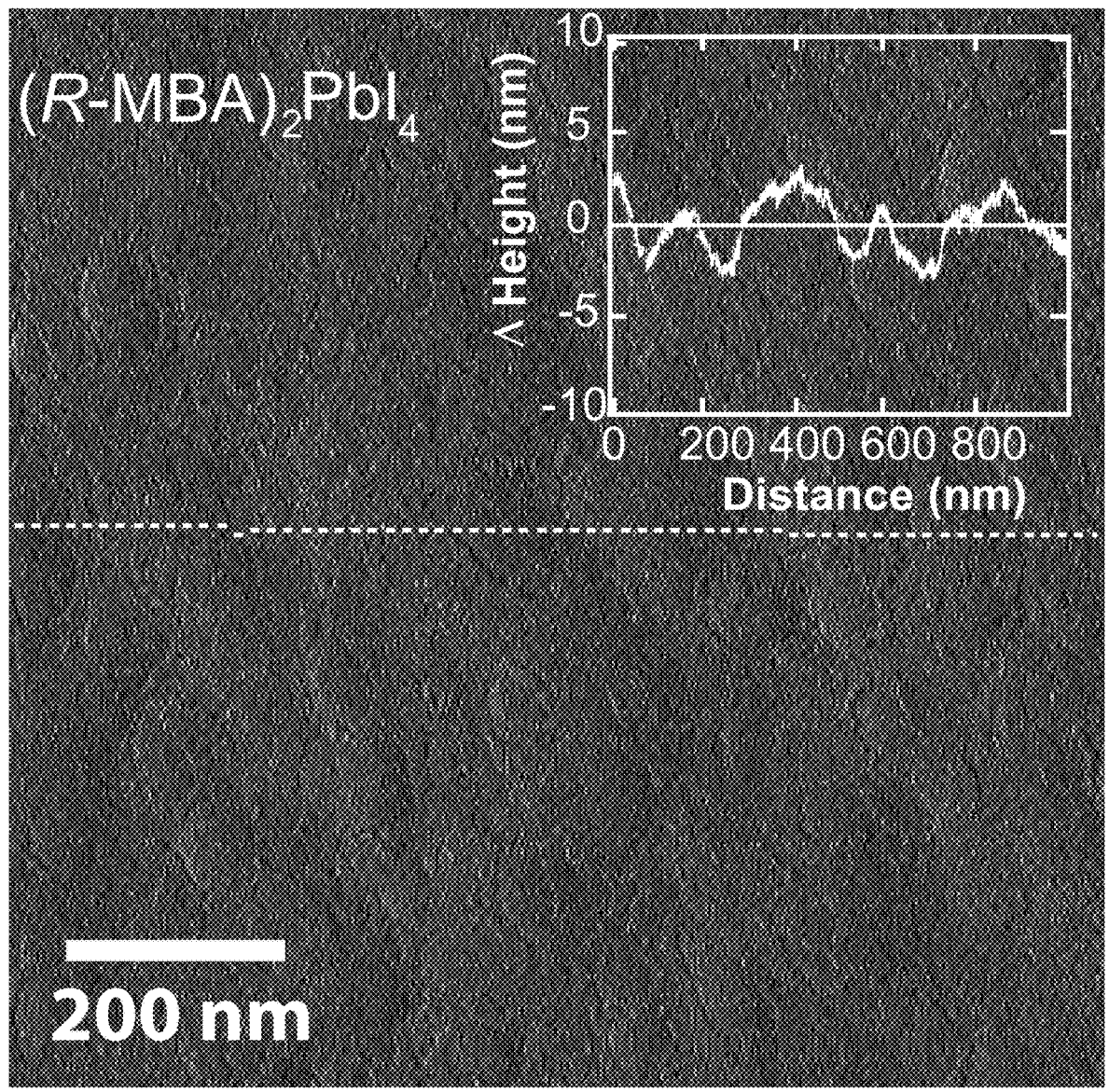
FIGS. 6A-6D illustrate morphological and photophysical characterization of HOIP materials, according to some embodiments of the present disclosure: AFM images of (R-MBA)$_2$PbI$_4$ (FIG. 6A) and (S-MBA)$_2$PbI$_4$ (FIG. 6C), respectively. The insets of FIGS. 6A and 6C show the AFM height profile of the dashed line drawn in the AFM image; Linear absorption (FIG. 6B quartz substrate), and circular dichroism (CD) spectra (FIG. 6D, quartz substrate). CD spectra display derivative features at the 200 nm to 600 nm range, with (R-MBA)$_2$PbI$_4$ and (S-MBA)$_2$PbI$_4$ showing opposite signs.
Figure 6B:
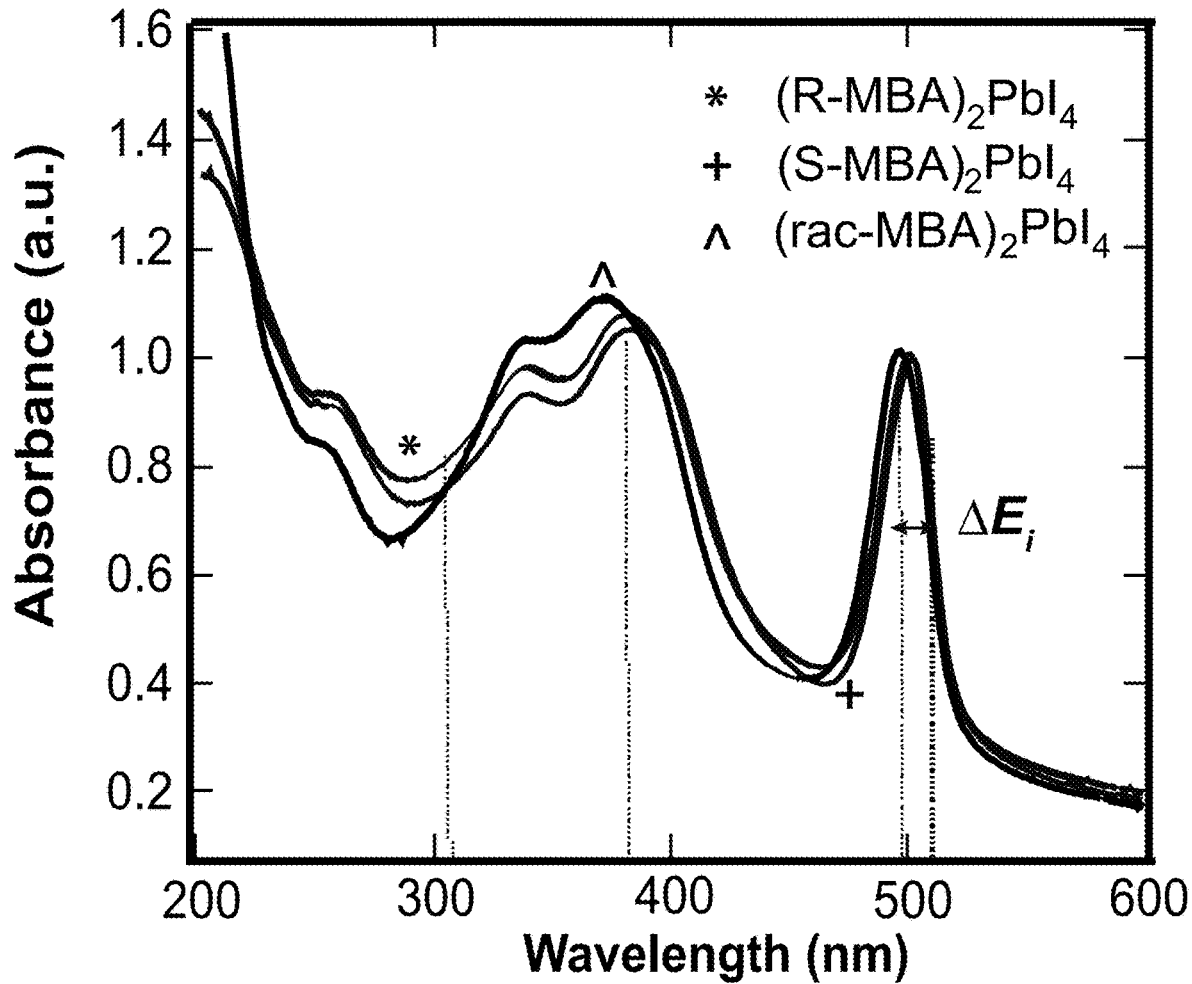
Figure 6C:
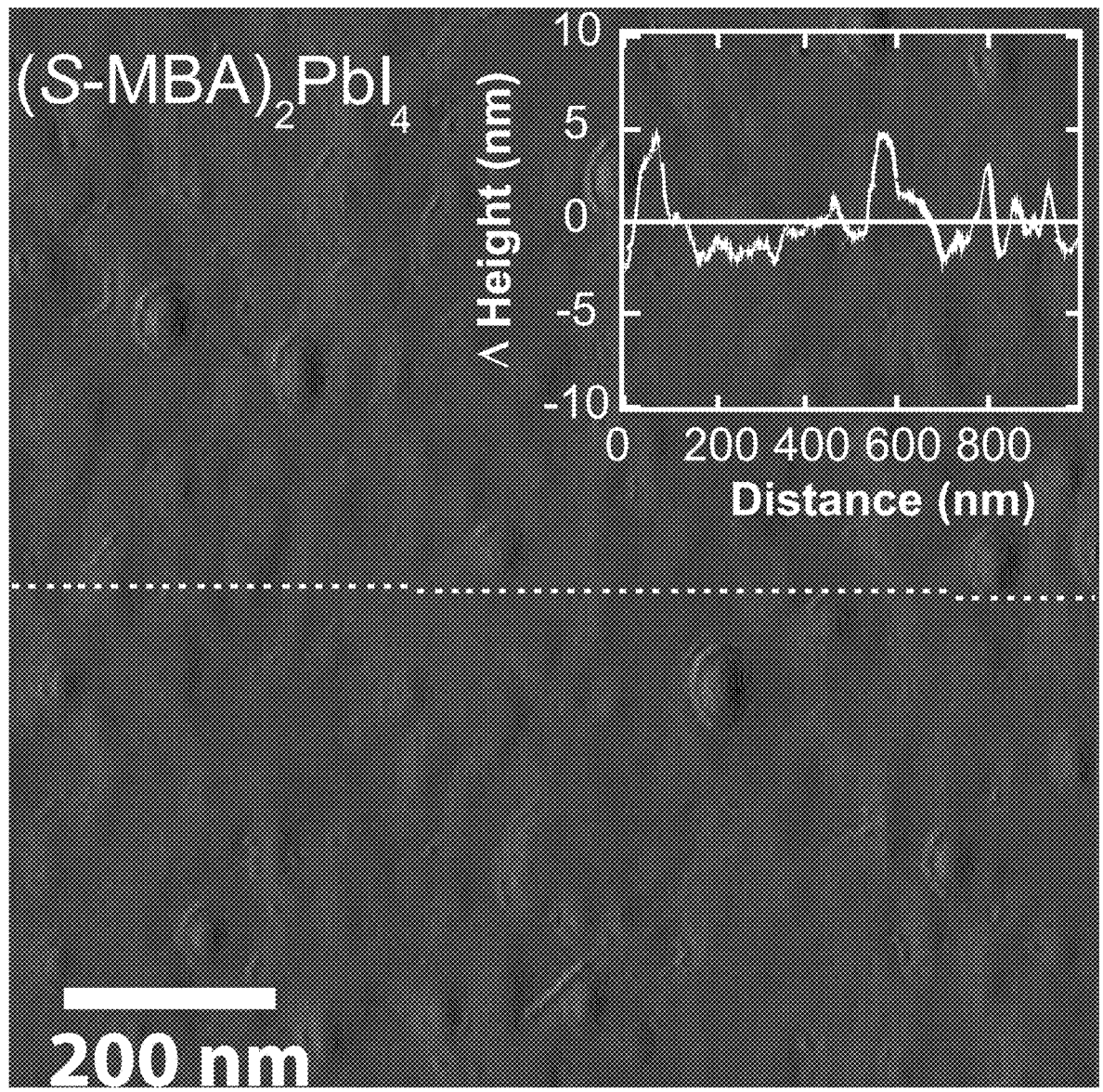

Atomic force microscopy (AFM) was used to determine the morphology and thickness of the 2D-layered films. All the films possess exceptionally low roughness with $R_q$ (root mean square average) between 1 nm and 3 nm, suggesting a very uniform morphology (see FIGS. 6A and 6C). The film thickness based on a 10 wt % solution was found to be ~50 nm (see FIGS. 7A-7D). Linear absorption spectra show a characteristic exciton peak at ~500 nm (see FIG. 6B), suggesting dielectric and quantum confinement in the 2D layers.

Figure 6D:
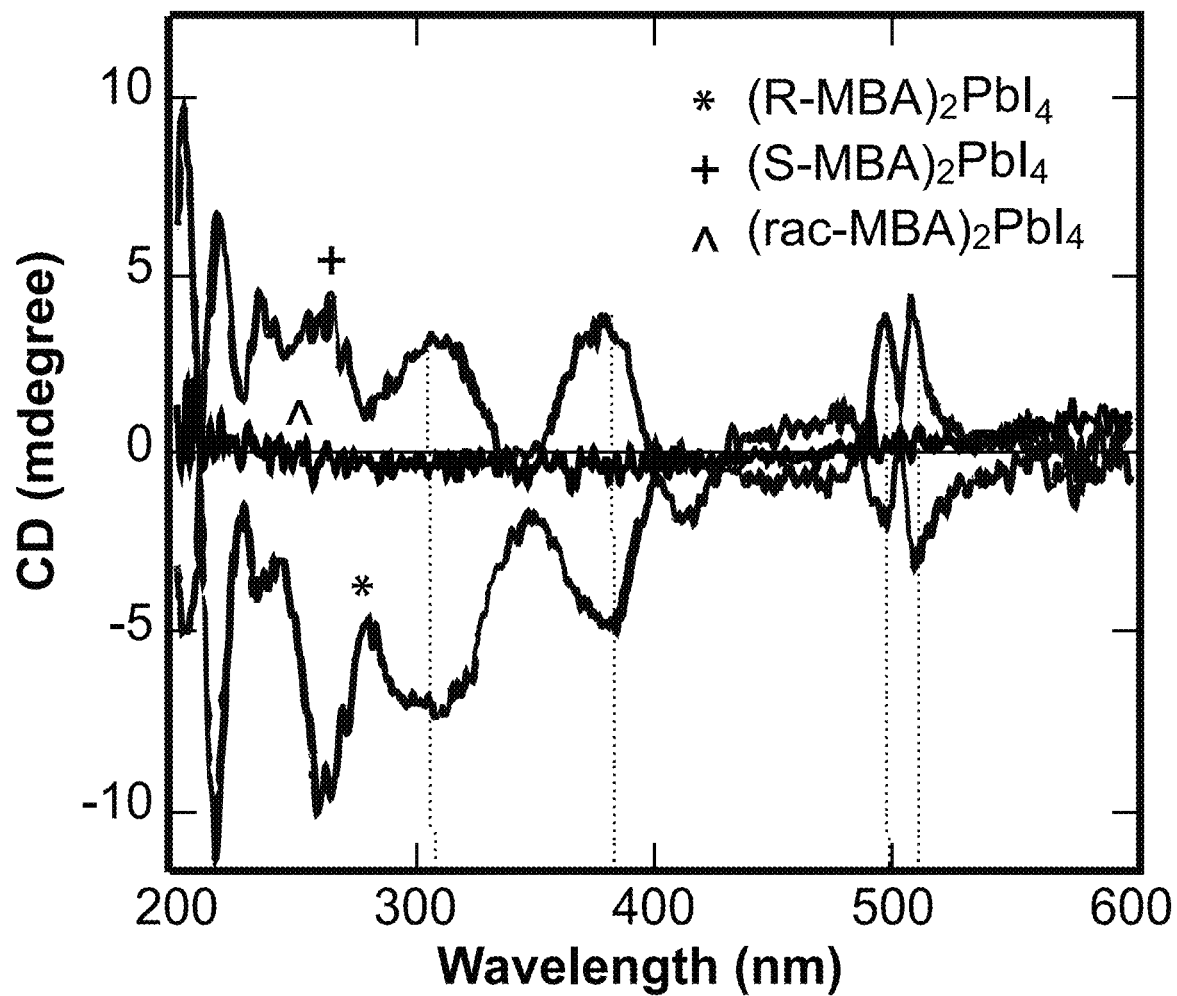
Figure 7A:
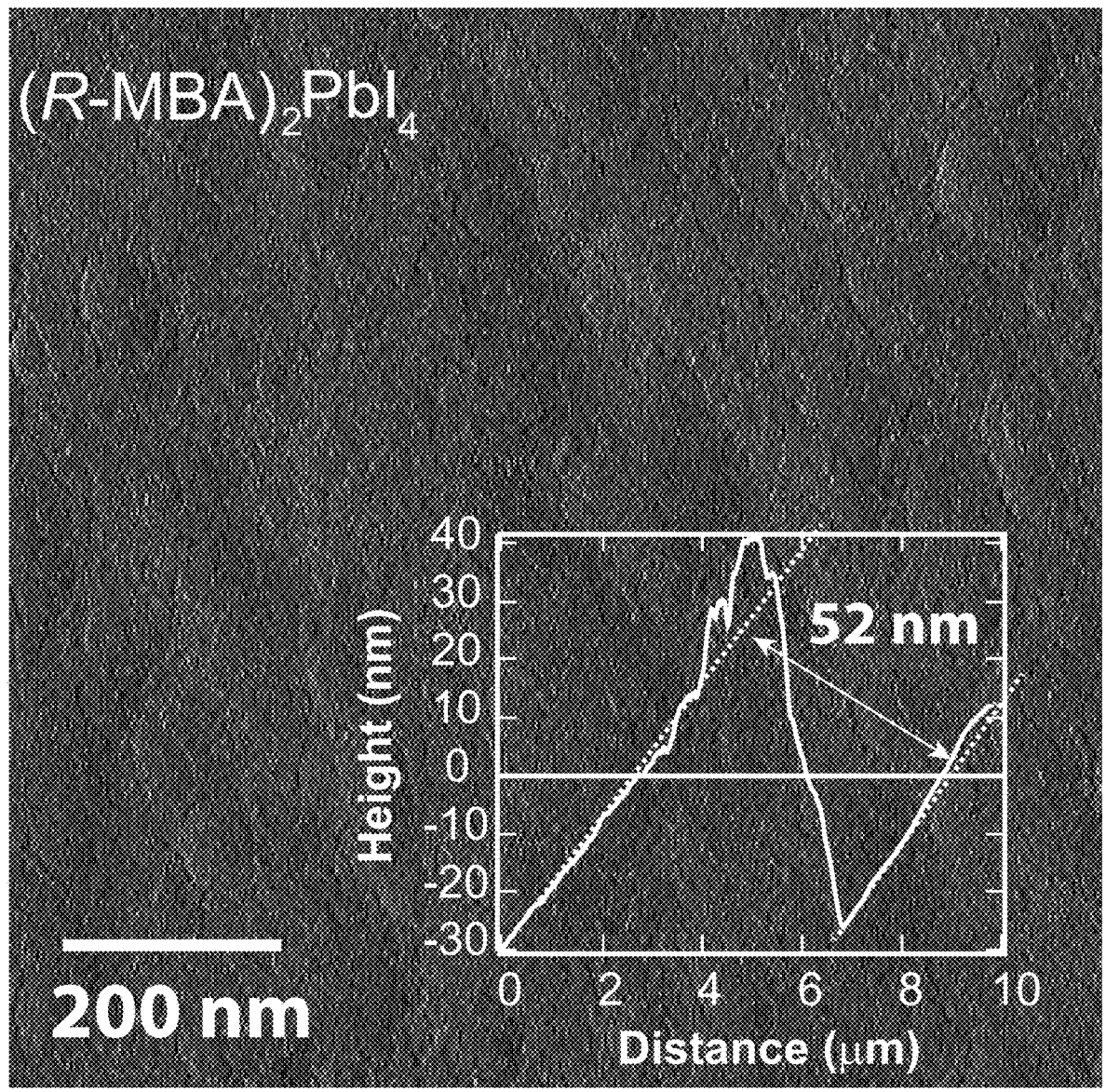
FIGS. 7A-7D illustrate AFM images of different 2D perovskite thin films, according to some embodiments of the present disclosure.
Figure 7B:
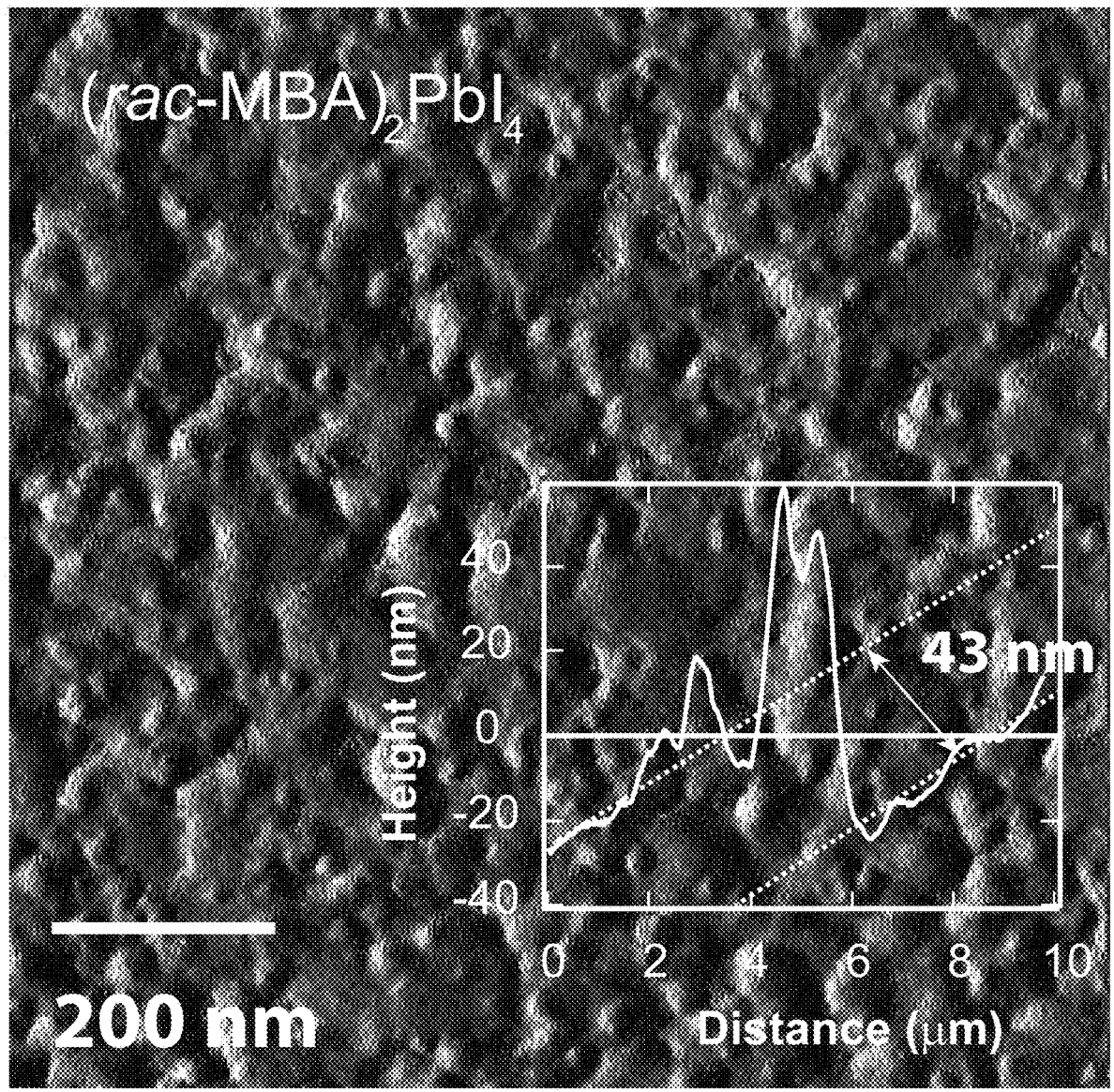
Figure 7C:
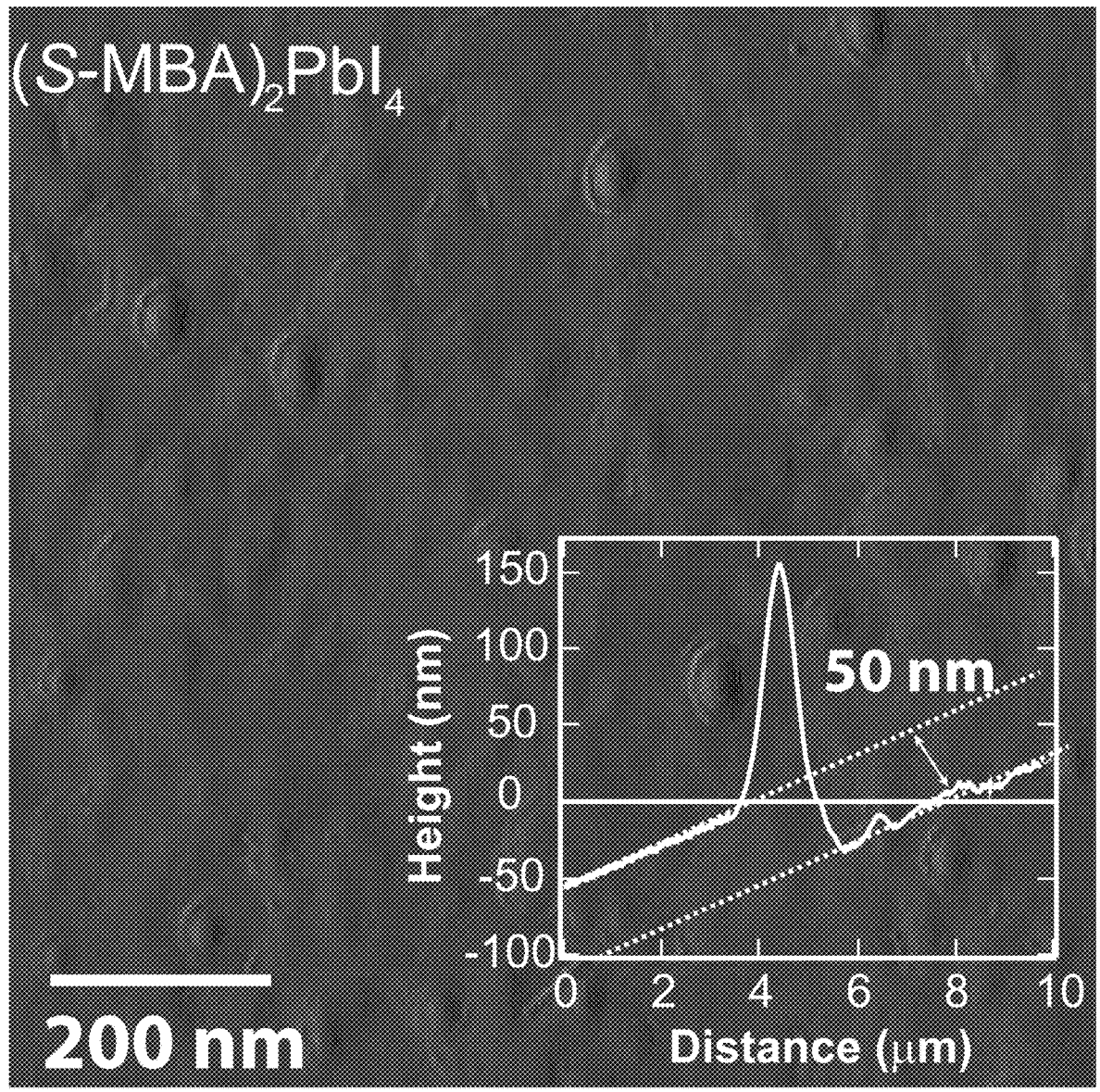
Figure 7D:
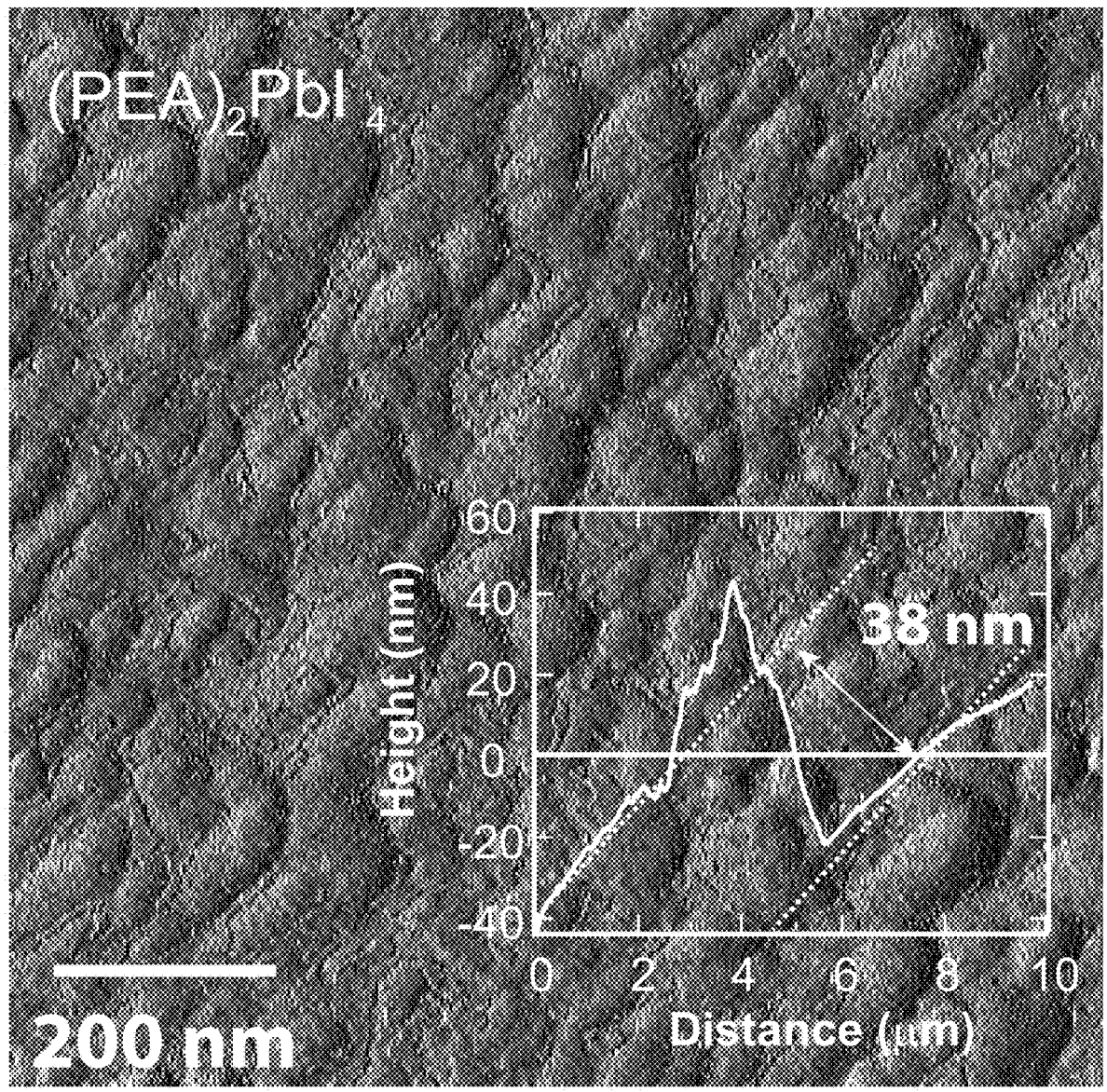
Figure 8A:
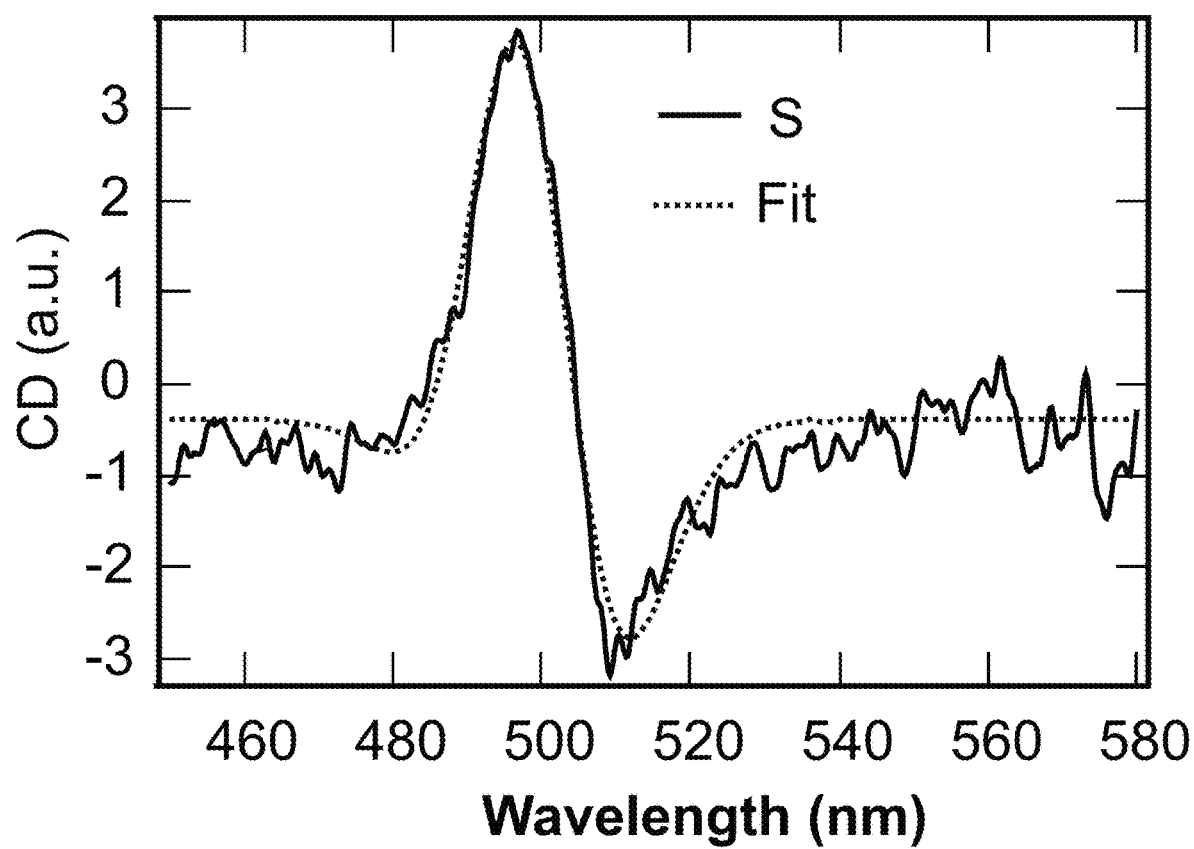
FIGS. 8A-8D illustrate an estimation of exciton splitting energy, according to some embodiments of the present disclosure.
Figure 8B:
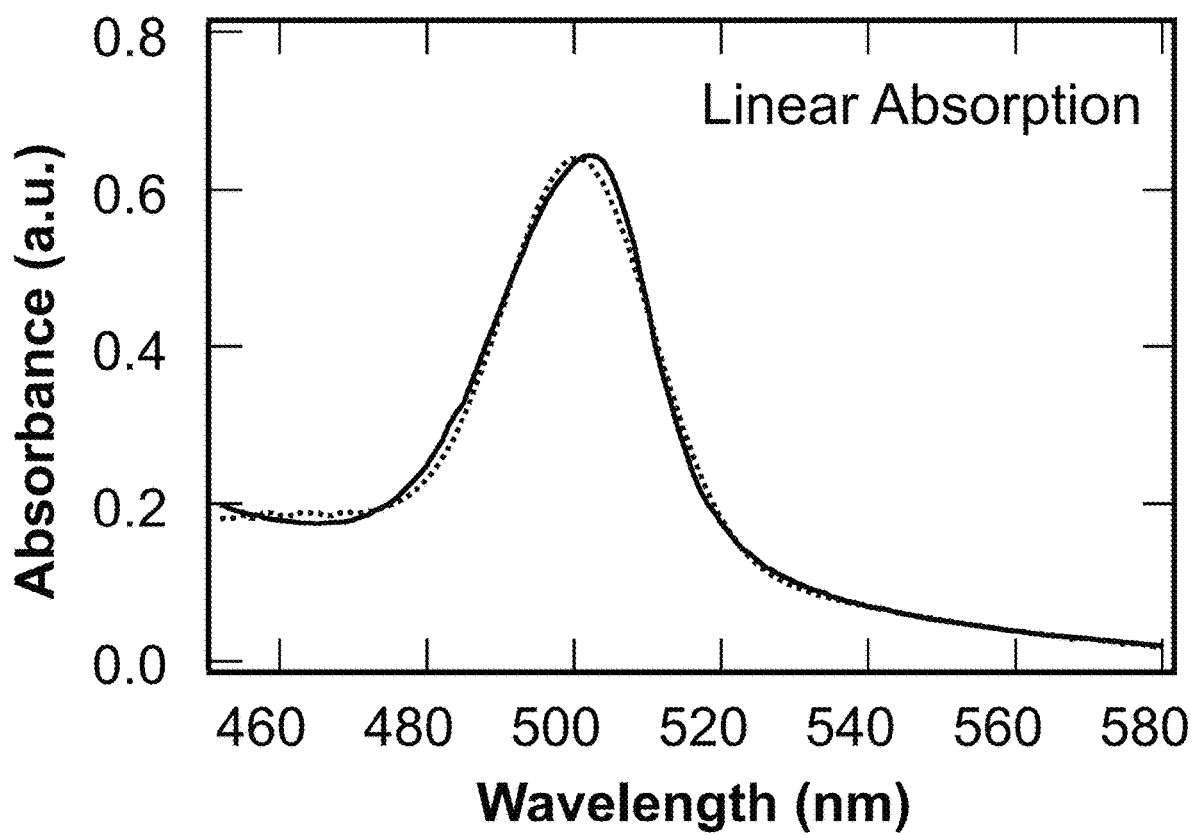
Figure 8C:
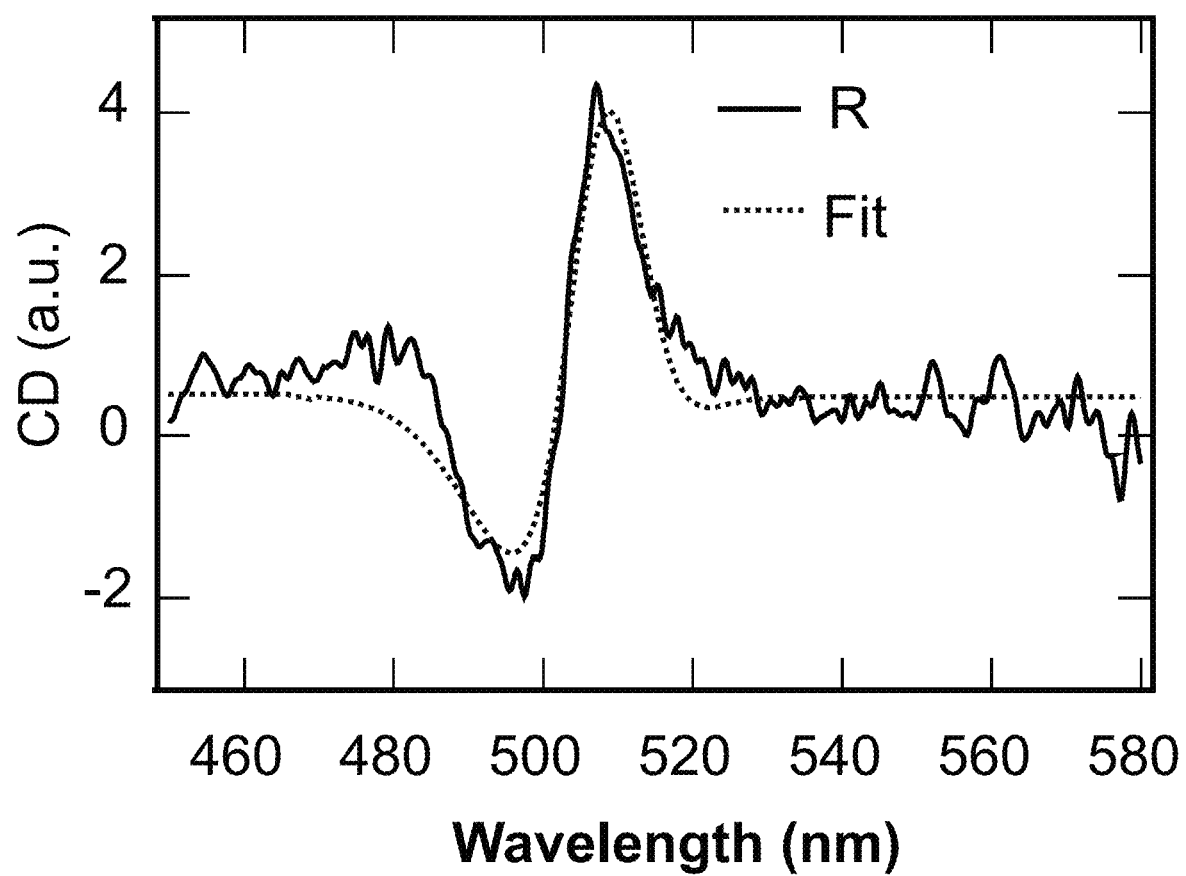
Figure 8D:
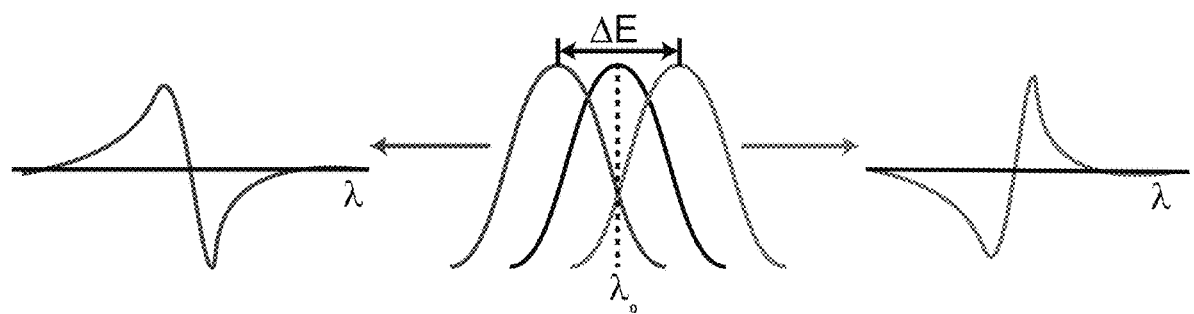

Circular dichroism (CD) of the thin films was also observed. Transmission CD spectra display distinct derivative features for R-MBA$_2$PbI$_4$ and S-MBA$_2$PbI$_4$ films, while the (rac-MBA)$_2$PbI$_4$ film exhibits no CD (see FIG. 6D). All the peaks in the CD spectra appear to be at the same wavelengths (at 215, 260, 310, 380, 497, and 508 nm) for (R- and S-MBA)$_2$PbI$_4$ films, but with opposite signs. While the high-energy CD signals (at 215 and 260 nm) can be assigned to the optical activity of the isolated organic molecules (R-MBA and S-MBA), the low energy CD response arises from the induced optical activity within the inorganic framework. This indicates that the incorporation of chiral organic amines leads to optical chirality in the inorganic Pb-I framework. This conclusion is supported by the derivative-like CD response around the band edge (at 497 and 508 nm), suggesting a lifting of the spin-degeneracy within the band-edge electronic states induced by the chiral molecules. The exciton splitting energy ($\Delta E_i$) is estimated to be 51 meV based on a Gaussian fitting of the CD and linear absorption spectra (see FIGS. 8A-8D).

Figure 9A:
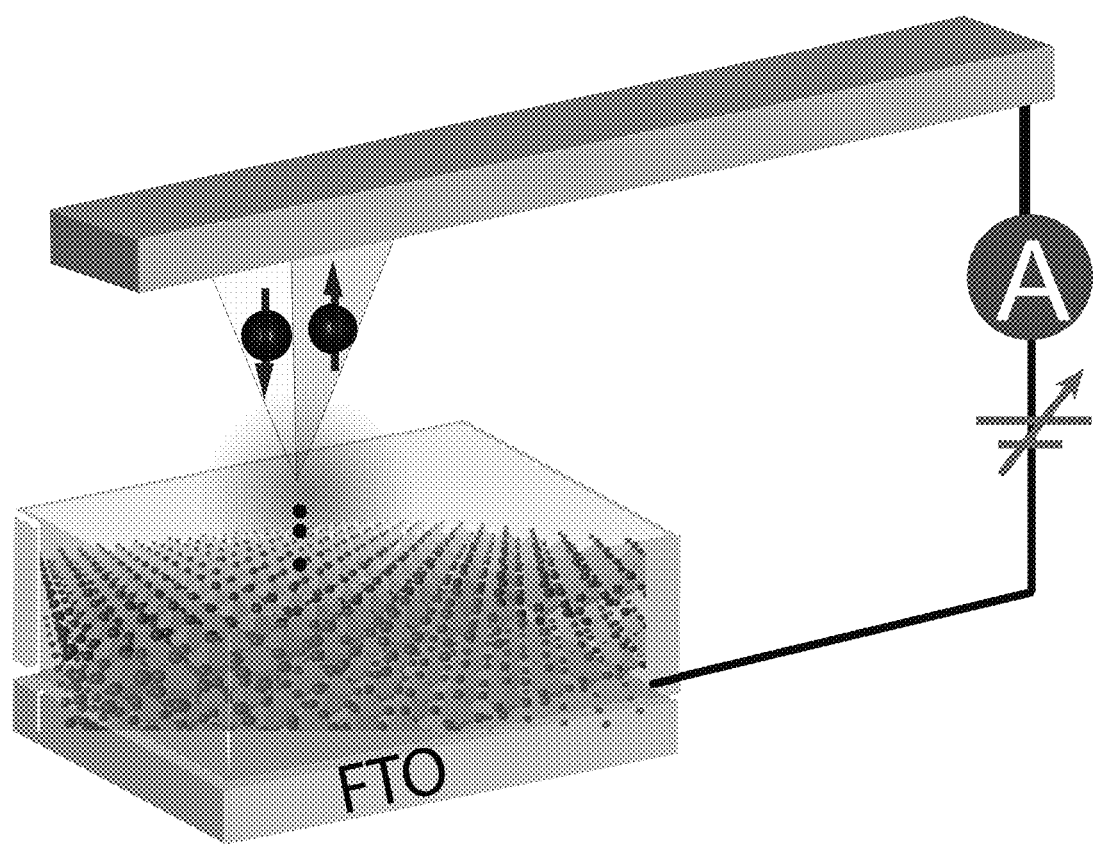
FIGS. 9A-9D illustrate magnetic conductive-probe atomic force microscopy (mCP-AFM) measurements, according to some embodiments of the present disclosure.

Magnetic conductive probe AFM (mCP-AFM) measurements were also completed. Specifically, spin-dependent charge transport properties in the chiral 2D perovskite films were assessed by conductive probe AFM (CP-AFM) with a ferromagnetic (FM) tip (Co—Cr coated). Oriented chiral perovskite films were prepared by spin-casting a DMF solution of perovskite crystals onto FTO substrates (see FIG. 9A). The FM tip can be magnetized by a permanent magnet with different magnetization directions (field-up or field-down with respect to the substrate), and the magnetized tip was subsequently employed during the CP-AFM measurements. Referring again to FIG. 9A, an electric bias potential was applied with respect to the FTO substrate, and the resulting current indicated electron transfer from the substrate to the tip through the 2D perovskite films. As the layers were orientated parallel to the substrate, vertical charge transport occurred when carriers tunneled from the inorganic layers through the organic chiral molecules. The helical potential in the chiral center controls the charge transfer rate for different spin polarities of the tunneling carriers. The carriers transferred through multiple vertical helical potentials in the thin 2D hybrid perovskite film (~50 nm) that consisted of ~36 inorganic/organic layers. The spin-selectivity through the multilayers was much stronger than through a monolayer or even a large DNA molecule.

Figure 9B:
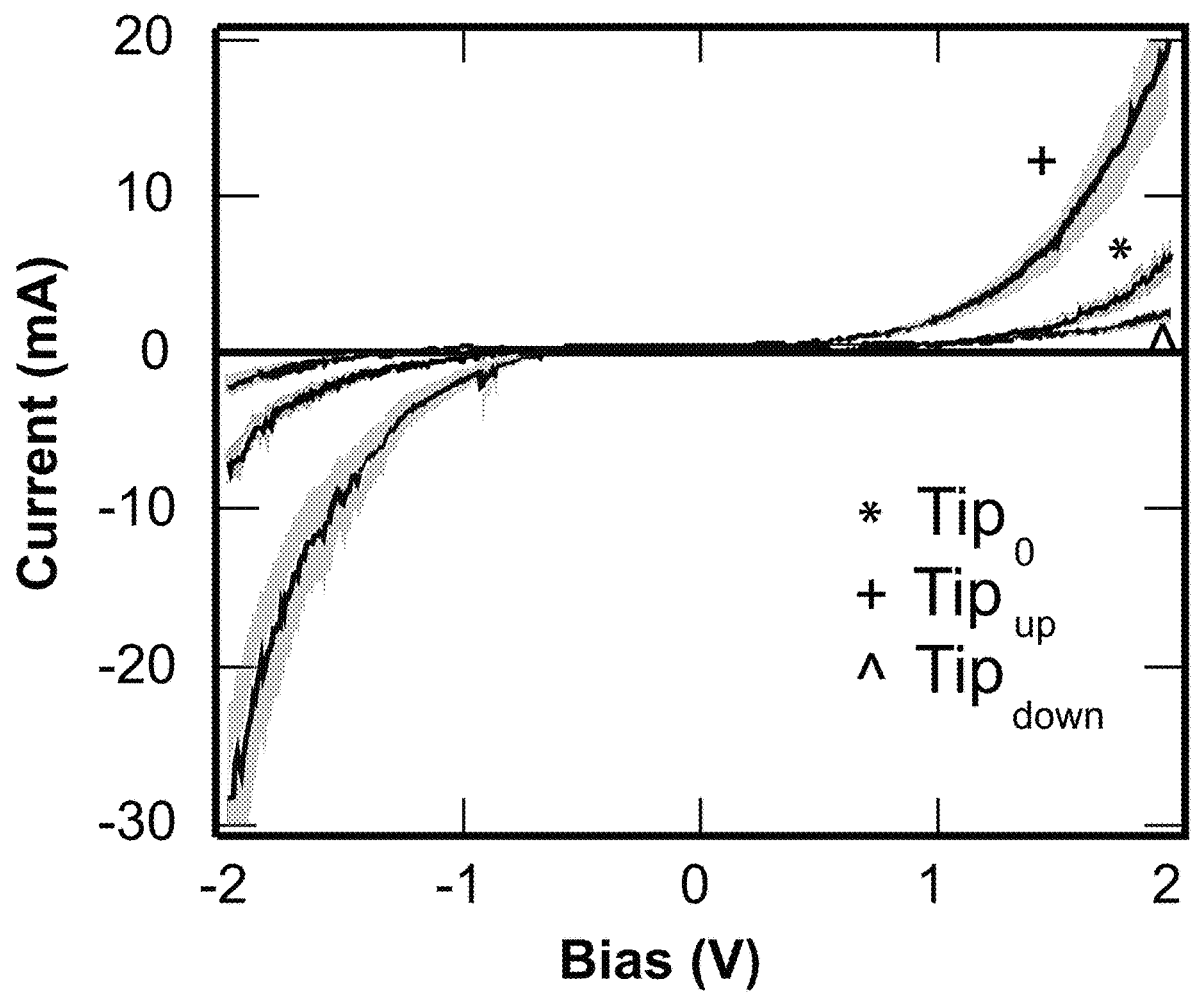
Figure 9C:
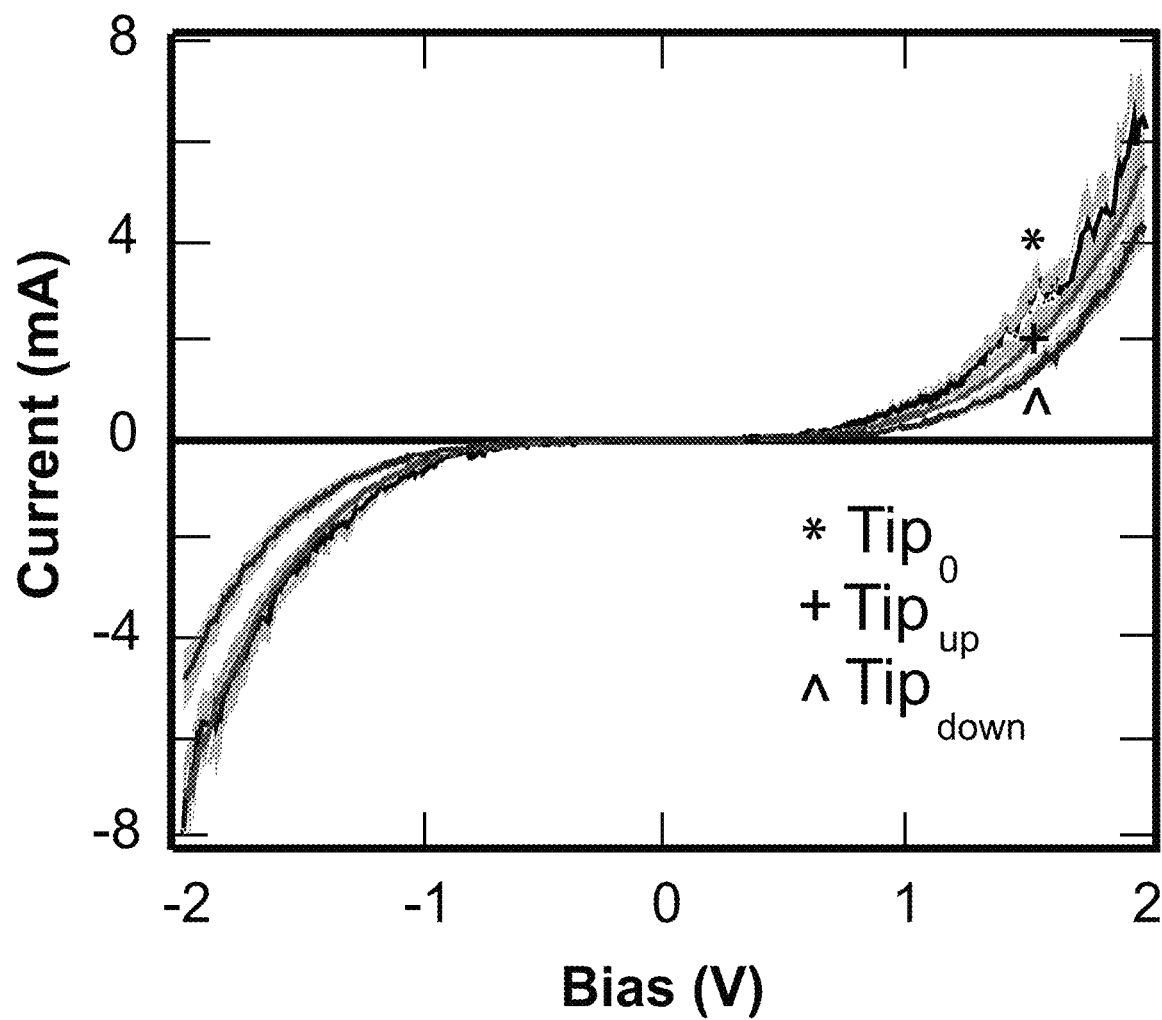
Figure 9D:
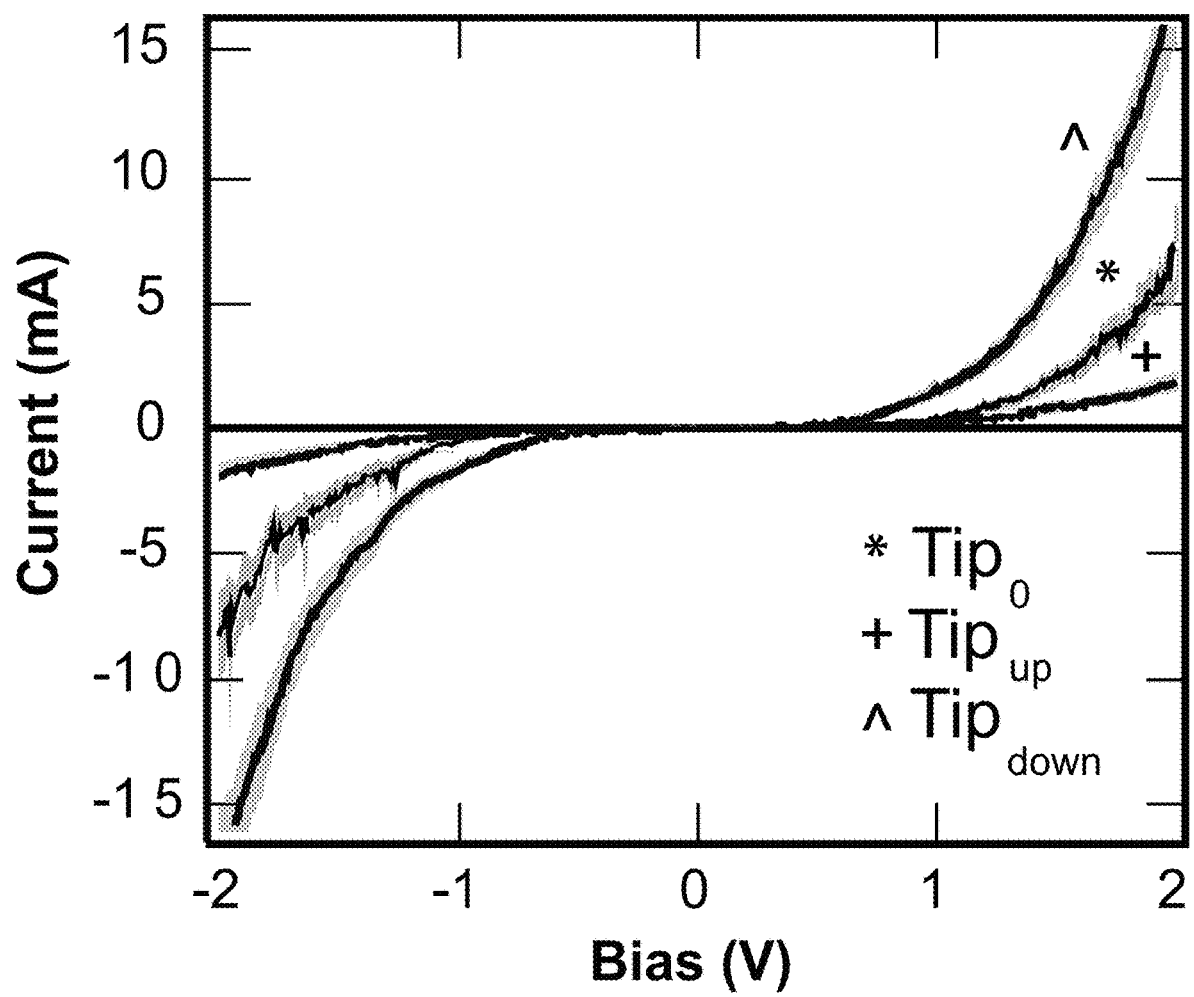
Figure 10:
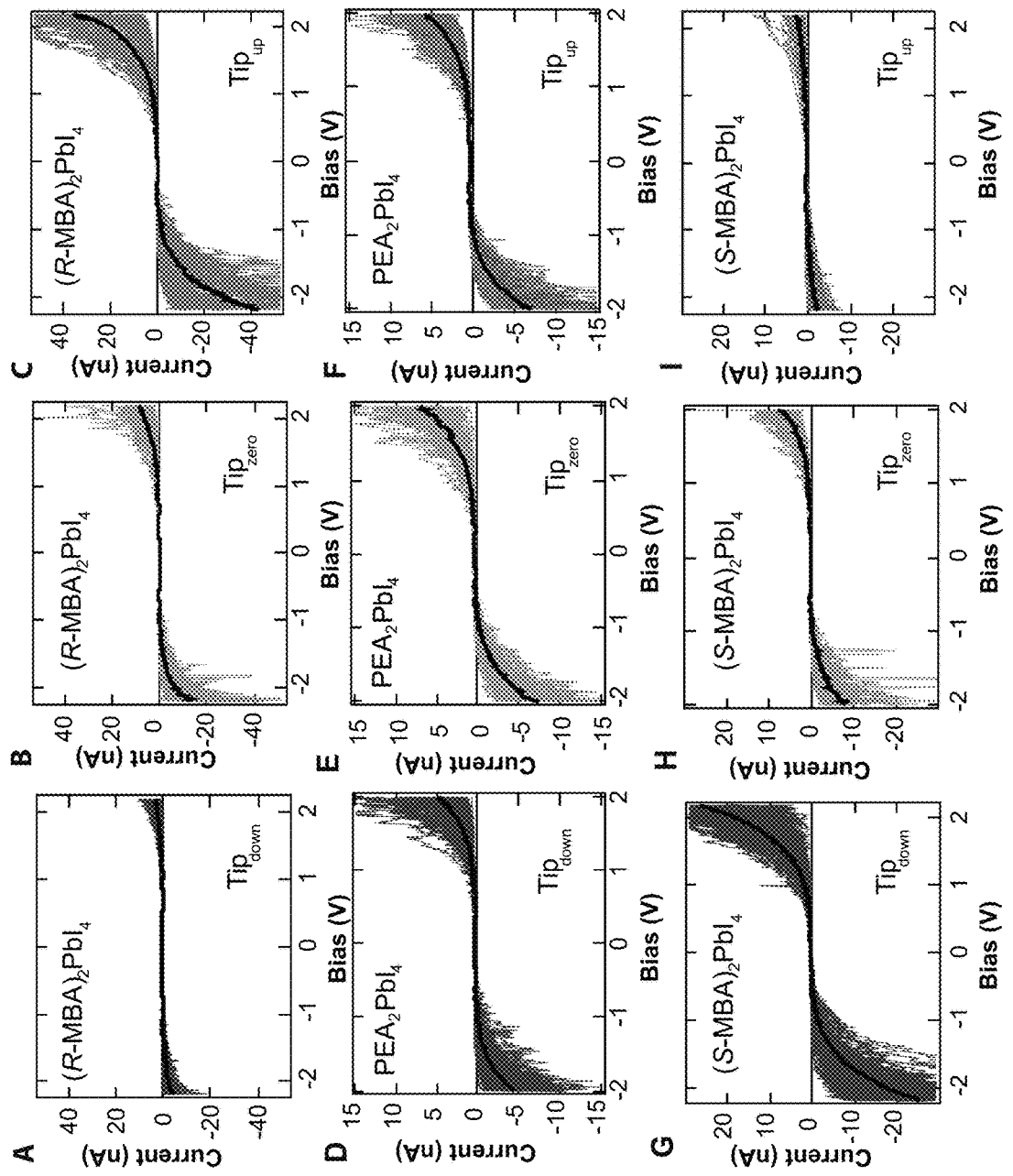
FIG. 10 illustrate raw and averaged current-voltage (I-V) curves from the mCP-AFM measurements, according to some embodiments of the present disclosure. (Panels A-C)

The average current-voltage (I-V) curves measured for different 2D perovskite films under various magnetization directions is shown in FIGS. 9B-9D. All the measurements were conducted at room temperature. The solid traces represent the average of over 100 scans, while the shaded region around the traces is the statistical 95% confidence limits (see FIG. 10). All the I-V curves displayed an "S" shape behavior, suggesting charge transport occurs through a double barrier tunneling potential. For the (R-MBA)$_2$PbI$_4$ film, much higher current was measured when the tip was magnetized in the "up" direction versus that in the "down" direction (see FIG. 8B). That is, carriers with their spin oriented parallel to the tip magnetization direction were preferentially transferred from the FTO to the magnetized tip over those with antiparallel spin orientation. The opposite behavior was observed for the (S-MBA)$_2$PbI$_4$ film, where higher current was observed when the tip was magnetized in the "down" direction as compared to the "up" direction (see FIG. 9D). In contrast, non-chiral phenethyl-ammonium lead iodide, PEA$_2$PbI$_4$ films showed little if any preference for the different tip magnetization direction.

To quantify the anisotropy of the polarized currents that were measured, spin-polarization, P, is defined as $$P = \frac{I_+ - I_-}{I_+ + I_-} \times 100\% \qquad (1)$$

where $I_+$ and $I_-$ are the measured currents at −2 V when the tip magnetic field is pointing up or down, respectively. CP-AMF resulted in an exceptionally high spin-polarization, P, of +86% and −84% for (R-MBA)$_2$PbI$_4$ and (S-MBA)$_2$PbI$_4$ films, respectively. Such spin-polarization is significantly higher than that reported for chiral self-assembled monolayer (SAM) systems (typically in the range of 30-50%), thus supporting the hypothesis of improved spin-selectivity through multiple chiral tunneling process. The multilayer configuration of the hybrid 2D layers allows for study of the thickness dependence of the spin-polarization. Interestingly, it was determined that the spin-polarization, P, exhibits a weak (if any) dependence on the film thickness. That is, P was consistently high (86-92%) for (R-MBA)$_2$PbI$_4$ films with varying thickness between 28 nm and 75 nm (see FIGS. 11A-11C).

Spin-valve devices based on a chiral 2D hybrid perovskite interlayer was also evaluated. The CISS effect was studied in spin-valve devices, using a single ferromagnetic (FM) electrode instead of two FM electrodes as in more traditional spin-valves. Spintronic devices were fabricated with one FM electrode (NiFe) and a non-magnetic electrode (ITO) separated by a 2D hybrid perovskite film and the NiFe electrode positioned between a gold layer and the 2D hybrid perovskite film. The 2D perovskites were either chiral with opposite handedness or non-chiral. The device resistance was measured at temperature of 10 K upon application of an out-of-plane external magnetic field having strength, B. The resistance as a function of magnetic field, which was dominated by the magnetoresistance (MR) response of the three devices based on (R-MBA)$_2$PbI$_4$, (S-MBA)$_2$PbI$_4$, and (PEA)$_2$PbI$_4$ interlayer, are shown in FIGS. 12A, 12B, and 12C, respectively. The MR is defined by:

$$MR = \frac{R(B) - R(0)}{R(0)} \times 100\% \qquad (2)$$

The difference in the MR(B) response of the various devices with different chirality is clearly observed. First, the (R-MBA)$_2$PbI$_4$ and (S-MBA)$_2$PbI$_4$ based devices show opposite MR(B) responses. Second, the MR(B) response followed the hysteresis loop of the FM electrode, since the spin-polarization of the injected carriers is proportional to the magnetization of the NiFe electrode. The opposite MR(B) response for devices based on layers with opposite chirality clearly demonstrates that the injected spin-polarized carriers from the FM electrode move through the chiral perovskite layers while experiencing CISS. This is reflected in the electrical resistance which is different for carriers with opposite spins. In contrast, the MR(B) response of the device based on non-chiral (PEA)$_2$PbI$_4$ did not show the same response as those based on the chiral systems. As seen in FIG. 12C, it did not follow the NiFe magnetization response, and thus had no CISS. Instead, the MR(B) response of this device resulted from an anisotropic magnetoresistance of the FM electrode.

The spin-selectivity observed here results from spin-polarized tunnel barriers formed by the chiral organic layers. The 2D layered system formed multilayers of alternating inorganic and organic barrier layers (see FIGS. 3 and 4A). The tunnel barrier height for carrier transport through the organic layers depends upon the spin and the handedness of the chiral molecules. It may be hypothesized, without wishing to be bound by theory, that the injected spin aligned carriers are mainly holes because the work functions of NiFe and ITO are both close to the valence band maximum of 2D perovskites (see FIG. 13). These spin-polarized tunneling barriers act as a spin-filter, preferentially promoting tunneling of one spin-orientation. The MR response of the spintronic devices are therefore consistent with the mCP-AFM measurements (see FIGS. 9A-9D) and originates from CISS in the tunneling regime.

A thickness dependent MR study was also performed (see FIG. 14A). The MR response shows a weak dependence on the film thickness, similar to that observed for the mCP-AFM measurements discussed above. The maximum MR value, $MR_{max}$ vs. thickness ($MR_{max}(d)$ response was substantially different than that observed in traditional spin-valve devices, in which $MR_{max}(d)$ decreased exponentially with thickness due to the process of spin-decoherence as carriers transvers by diffusion a non-chiral medium. Here the slight thickness dependence is likely due to competing effects that occur for thicker films. On the one hand, more tunnel barriers induce a higher spin-selectivity. However, spin-lattice relaxation process occurs simultaneously during the spin-selective transport process. Therefore, the thickness dependence is a result of two competing processes; namely spin-selective increase due to the increase in the number of chiral barrier layers, and spin-relaxation due to spin scattering (see FIG. 14B). To further separate these two counteracting effects (CISS vs. spin relaxation), we have developed a semi-quantitative model assuming a simple exponential decay function that represents the process of the spin decoherence upon diffusion in the perovskite layer. The difference between the measured $MR_{max}(d)$ and the simulated spin relaxation with d indicates the contribution from CISS (see FIG. 14A). Although it is a rough estimation, it is clearly seen that the spin selectivity is enhanced as the film thickness increases (see FIG. 14A). Additionally, the MR response did not show clear bias voltage dependence (see FIG. 15). This is also in contrast with the MR response vs. bias in traditional spin-valve devices, in which the MR response decreases significantly with increasing bias voltage. This demonstrates that the transport of spin-polarized carriers in the chiral hybrid layers is governed by a tunneling process, and therefore is different than the spin-injection mechanism that occurs in a prototypical spin-valve.

In conclusion, it is shown herein that the spin-transport in 2D hybrid organic inorganic perovskites can be effectively manipulated upon introducing chiral molecules into the organic spacer layers in the multilayer structures, which occurs via the CISS mechanism. Magnetic conductive probe AFM studies demonstrate that charge transport through oriented chiral 2D perovskite is highly selective depending on the induced magnetization of the probe tip and the handedness of the embedded chiral organic molecules. The spin-selectivity is observed to be much larger than previously reported in chiral SAM systems, as carriers transfer through multiple chiral layers of spin-polarized tunneling process. Magnetoresistance measurements in spintronics devices further confirm the spin-filtering effect enabled by the chiral organic layers, forming spin-valve devices based on a single FM electrode. The successful demonstration of CISS effect in the solution processed polycrystalline 2D chiral perovskite films opens the door for future spintronic applications of chiral materials.

As described below, chiral hybrid semiconductors are now expanded to layered tin iodide perovskites by templating with chiral (R/S-)methylbenzylammonium (R/S-MBA). As shown herein, the interplay between chiral organic molecules and inorganic Sn-I sublattices can result in the largest octahedra distortion among all reported 2D layered Sn-I perovskites. The incorporation of chiral MBA cations also leads to chiroptical response within the inorganic Sn-I sublattice, which can be modulated by alloying Sn with Pb. The incorporation of chiral MBA cations leads to circularly polarized absorption from the inorganic Sn-I sublattice, displaying chiroptical activity in the 300-500 nm wavelength range. Also shown herein, is that the charge transport through (R-/S-MBA)$_2$SnI$_4$ thin films is highly spin dependent, and spin-polarization of as high as 94% was achieved. The bandgap and chiroptical activity are modulated by alloying Sn with Pb, in the series of (MBA)$_2$Pb$_{1-x}$Sn$_x$I$_4$.

Crystal Structure of Chiral (R-/S-MBA)$_2$SnI$_4$ and Racemic (rac-MBA)$_2$SnI$_4$. Single crystals of chiral (R-/S-MBA)$_2$SnI$_4$ and the racemic phase (rac-MBA)$_2$SnI$_4$ were grown from a concentrated hydroiodic acid solution. Orange, rod-like crystals were collected after a slow-cooling process from 90° C. to room temperature. Crystallographic data and structure refinement information appear in Table 1. The crystal structure consists of a layer of corner-sharing SnI$_6^{4-}$ octahedra, with a bilayer of organic MBA cations separating the inorganic layers (see FIG. 16). The organic cation phenyl rings all align approximately parallel to the b axis and the chiral R-/S and achiral rac-compounds display similar cell parameters. All three compounds crystallized in the orthorhombic system. The incorporation of the chiral MBA molecules resulted in a chiral space group P2$_1$2$_1$2$_1$ for (R-/S-MBA)$_2$SnI$_4$, while the racemic phase (rac-MBA)$_2$SnI$_4$ crystallized in the centrosymmetric space group Pnma.

TABLE 1

Crystal Data and Structure Refinement for (R-MBA)$_2$SnI$_4$, (S-MBA)$_2$SnI$_4$, and (rac-MBA)$_2$SnI$_4$

| | Compound Name | | |
|---|---|---|---|
| | (R-MBA)$_2$SnI$_4$ | (S-MBA)$_2$SnI$_4$ | (rac-MBA)$_2$SnI$_4$ |
| Empirical formula | C$_{16}$H$_{24}$N$_2$I$_4$Sn | C$_{16}$H$_{24}$N$_2$I$_4$Sn | C$_{16}$H$_2$4N$_2$I$_4$Sn |
| Crystal size (mm) | 0.037 × 0.159 × 0.171 | 0.039 × 0.146 × 0.185 | 0.025 × 0.173 × 0.321 |
| Formula weight | | 870.68 | |
| Temperature | | 250 K | |

TABLE 1-continued

Crystal Data and Structure Refinement for (R-MBA)$_2$SnI$_4$, (S-MBA)$_2$SnI$_4$, and (rac-MBA)$_2$SnI$_4$

| | Compound Name | | |
|---|---|---|---|
| Wavelength | | 0.71073 Å | |
| Crystal system | | Orthorhombic | |
| Space group | P2$_1$2$_1$2$_1$ | P2$_1$2$_1$2$_1$ | Pnma |
| Unit cell dimensions | a = 8.9098(2) Å, | a = 8.91262(19) Å, | a = 8.7887(3) Å, |
| | b = 28.7413(6) Å, | b = 28.7305(7) Å, | b = 28.7381(9) Å, |
| | c = 9.3567(2) Å | c = 9.3578(2) Å | c = 9.4273(3) Å |
| Volume | 2396.07(10) Å$^3$ | 2396.20(10) Å$^3$ | 2381.04(13) Å$^3$ |
| Z | 4 | 4 | 4 |
| Density (calculated) | 2.414 g/cm$^3$ | 2.413 g/cm$^3$ | 2.429 g/cm$^3$ |
| Absorption coefficient | 6.22 mm$^{-1}$ | 6.22 mm$^{-1}$ | 6.261 mm$^{-1}$ |
| F(000) | 1584 | 1584 | 1584 |
| θ range for data collection | 2.289 to 26.371° | 2.289 to 26.372° | 2.274 to 26.369° |
| Index ranges | −11 <= h <= 9, −35 <= k <= 35, −11 <= l <= 11 | −11 <= h <= 10, −33 <= k <= 35, −11 <= l <= 10 | −9 <= h <= 10, −35 <= k <= 33, −11 <= l <= 11 |
| Reflections collected | 24481 | 24777 | 14478 |
| Independent reflections | 4550 [R$_{int}$ = 0.0217] | 4502 [R$_{int}$ = 0.0271] | 2427 [R$_{int}$ = 0.0252] |
| Completeness to θ = 25.242° | 100% | 100% | 100% |
| Refinement method | | Full-matrix least-squares on F$^2$ | |
| Data/restraints/parameters | 4897/0/212 | 4894/0/212 | 2477/0/111 |
| Goodness-of-fit | 1.091 | 1.141 | 1.122 |
| Final R indices [I > 2σ(I)] | R$_{obs}$ = 0.0160, wR$_{obs}$ = 0.0183 | R$_{obs}$ = 0.0190, wR$_{obs}$ = 0.0216 | R$_{obs}$ = 0.0204, wR$_{obs}$ = 0.0238 |
| R indices [all data] | R$_{all}$ = 0.0326, wR$_{all}$ = 0.0338 | R$_{all}$ = 0.0408, wR$_{all}$ = 0.0415 | R$_{all}$ = 0.0460, wR$_{all}$ = 0.0470 |
| Largest diff. peak and hole | 0.261 and −0.500 e · Å$^{-3}$ | 0.420 and −1.120 e · Å$^{-3}$ | 0.988 and −0.496 e · Å$^{-3}$ |

R = Σ||F$_o$| − |F$_c$||/Σ|F$_o$|, wR = {Σ[w(|F$_o$|$^2$ − |F$_c$|$^2$)$^2$]/Σ[w(|F$_o$|$^4$)]}$^{1/2}$ and w = 1/[σ$^2$(F$_o^2$) + (0.0172P)$^2$ + 0.1141P] where P = (Fo$^2$ + 2Fc$^2$)/3

The crystal packing and hydrogen bonds were similar in all three compounds. Taking (R-MBA)$_2$SnI$_4$ as an example, the organic MBA cations penetrated into the perovskite sheet (~0.45 Å), with the ammonium head forming hydrogen bonds (N-H•••I) with two axial (N-H•••I$_a$: 2.75 and 2.94 Å) and one equatorial (N-H•••I$_e$: 2.95 Å) iodide atoms (see Panel (a) of FIG. 17). The adjacent MBA cations along the stacking direction (b direction) interact closely by π-π stacking of benzene rings with a distance between ring centers of 3.842 Å (see Panel (b) of FIG. 17). The ammonium head deviates from the center of the cages in all three compounds (see Panels (c) and (e) of FIG. 17). The hydrogen bonds significantly distort the SnI$_6^{4-}$ octahedra from an ideal configuration. In (R-MBA)$_2$SnI$_4$ (see Panel (a) of FIG. 17), the hydrogen bonds with the axial iodide atoms tilt the axial Sn-I bond by 8.76° from the ideal vertical axis. The axial Sn-I displays two bond distances (3.154 and 3.176 Å), with the longer one corresponding to the shorter N-H•••I$_a$ distance, suggesting that strong hydrogen bonding is likely responsible for the axial bond tilting. While the out-of-plane distortion of the inorganic sheets was very small (<1°), there was significant in-plane rotation among the octahedra (see Panels (c) and (e) of FIG. 17). The hydrogen bonds with equatorial iodide atoms contribute to the in-plane tilting of the corner-shared octahedra since every bridged I atom is bounded to the ammonium head by N-H•••I$_e$.

(R-MBA)$_2$SnI$_4$ displayed two in-plane Sn—I—Sn bond angles, namely 153.52° and 153.24°, both of which deviated significantly from 180° (ideal octahedra). The longest and shortest Sn-I bonds within an octahedron are both located within the equatorial directions, and the differences are as large as 0.77 Å. The average Sn-I bond distance is 3.267 Å, while the longest Sn-I bond is 3.727 Å, one of the longest bonds reported among tin iodide perovskites (such a bond-length can be considered semi-coordinated). To further quantify the degree of octahedral distortion, the bond length distortion index (D) and bond angle variance (σ$^2$) were calculated from $$D = \frac{1}{6}\sum_{i=1}^{6}\frac{|d_i - d_0|}{d_0},$$

$$\sigma^2 = \frac{1}{11}\sum_{i=1}^{12}(\theta_i - 90)^2,$$

where d$_i$ represents the individual Sn-I bond lengths, d$_0$ is the mean Sn-I bond distance, and Oi corresponds to the octahedra I—Sn—I bond angles. For an ideal octahedron, both D and σ$^2$ are exactly 0. The larger the value of D and σ$^2$, the larger is the octahedra distortion. Interestingly, it was determined that these layered (MBA)$_2$SnI$_4$ perovskites exhibit the largest reported SnI$_6$ octahedron distortion index among values reported in literature (see FIG. 18). (R-MBA)$_2$SnI$_4$, (S-MBA)$_2$SnI$_4$ and (rac-MBA)$_2$SnI$_4$ showed a distortion index of 0.079, 0.079 and 0.076 and bond angle variances of 10.37, 10.35, and 13.04 deg$^2$, respectively. The level of structural distortion in R-, S-, and rac-compounds are very similar. The high degree of structural distortion of the (MBA)$_2$SnI$_4$ compounds directly results in unusual structural parameters relative to their Pb-I analogs. For instance, the in-plane lattice constants of (R-MBA)$_2$SnI$_4$ (a=8.910 Å and c=9.357 Å) are slightly larger than those of (R-/S-/rac-MBA)$_2$PbI$_4$ (e.g., a=8.868 Å and b=9.247 Å in (R-MBA)$_2$PbI$_4$), although they both possess the same crystal structure and the ionic radius of Sn$^{2+}$ is smaller than that for Pb$^{2+}$. This ordering of bond lengths is in contrast with other Sn-I and Pb-I series that are templated by the same organic cations, for which generally the in-plane lattice constants of the hybrid Sn halides are smaller than those of their Pb analogs.

To study the optical and chiroptical properties of these hybrid tin iodide compounds, polycrystalline thin films of (MBA)$_2$SnI$_4$ were prepared by spin casting a DMF solution of the corresponding crystals. Linear absorption shows an absorption peak at 408 nm and a shoulder peak at 452 nm, which extends to ~500 nm. R-, S- and rac-films display no obvious differences in linear absorption spectra (see FIG. 19A). It is interesting to note that there is no obvious sharp exciton peak in these MBA$_2$SnI$_4$ compounds. Transmission circular dichroism (CD) measurements show distinct CD signals from 300-500 nm for (R-MBA)$_2$SnI$_4$ and (S-MBA)$_2$SnI$_4$ thin films, while (rac-MBA)$_2$SnI$_4$ displays no CD (see FIG. 19B). All the CD peaks are at the same wavelengths (at 357, 402, 443, and 473 nm) with opposite signs for (R-MBA)$_2$SnI$_4$ and (S-MBA)$_2$SnI$_4$ thin films. It is notable that none of these chiroptically active transitions are from the organic component, which only absorbs in the range of 200-300 nm. In fact, these chiroptical transitions (at 402 and 443 nm, for example) correlate fairly well with their linear absorption peaks (at 408 and 452 nm respectively), indicating that the optical transitions originating from the inorganic sublattice acquired a chiral response. The Cotton effect was observed near the band edge electronic transitions (at 443 and 473 nm) in the chiral films, which is very similar to the chiral Pb analogs described above. Clearly, the incorporation of the chiral molecules has enabled the chiral optical activity of the electronic transition within the inorganic Sn-I sublattice.

To better examine the influence of the electronic properties of the inorganic sublattice on their chiroptical properties, a series of single-crystal Pb/Sn alloyed 2D perovskites (R-/S-MBA)$_2$Pb$_{1-x}$Sn$_x$I$_4$ (x=0–1) were prepared. Note that x value only represents the input nominal Sn/Pb ratio, while actual elemental composition was determined by EDS. It may be hypothesized that, when templated by the MBA cations, the electronic properties can be systematically modulated by metal alloying, thereby tuning their chiroptical properties. Powder XRD data of (R-MBA)$_2$Pb$_{1-x}$Sn$_x$I$_4$ (input composition: x=0, 0.05, 0.20, 0.50, 0.80, 1) show similar crystallinity and crystal pattern across the whole solid solution composition. Pawley refinements of the orthorhombic structure (space group P2$_1$2$_1$2$_1$) against the powder diffraction data suggest that all synthesized crystals of intermediate composition crystallized in the same space group. It is noted that the in-plane lattice parameters (a and c) increased slightly with increasing Sn content, which is consistent with single crystal data that indicated (R-MBA)$_2$SnI$_4$ has a larger lattice volume than (R-MBA)$_2$PbI$_4$. In contrast, the b lattice parameter corresponding to the stacking direction of the perovskite layers remained relatively unchanged across the series. These data indicate that the large distortion of the SnI$_6$ octahedra manifests across the alloyed specimens and is further responsible for the larger lattice volumes observed in the Sn-rich members of the series.

Linear optical properties of the powders were measured by diffuse reflectance spectroscopy. Optical bandgaps were extracted based on the absorption onsets from the Kubelka-Munk absorption spectra ($\alpha$/S=(1−R)$^2$/(2R)) (see FIG. 20A). The absorption spectra show sharp absorption edges suggesting direct bandgap semiconductors. Both (R-MBA)$_2$PbI$_4$ and (R-MBA)$_2$Pb$_{0.95}$Sn$_{0.05}$I$_4$ displayed characteristic excitonic peaks due to the strong dielectric confinement within the inorganic wells, but the sharp excitonic feature was no longer apparent for higher Sn concentrations. Interestingly, it was found that the optical bandgap displayed an anomalous trend in the alloyed samples. The optical bandgap ($E_g$) was initially reduced when adding more Sn to the (R-MBA)$_2$PbI$_4$ compounds, but the bandgap trend was not monotonic with increasing Sn content as expected from Vegard's law. Instead, there was a significant optical bandgap bowing effect in (R-MBA)$_2$Pb$_{1-x}$Sn$_x$I$_4$, with the minimum bandgap found at input x=0.2 ($E_g$=2.09 eV) (see FIG. 20B). Both the pure Pb and Sn compounds exhibited a higher optical bandgap (2.34 and 2.28 eV) than did the intermediates. This bowing trend below the optical gaps associated with both endpoints can also be visually observed from the color of the as-grown crystals. Both x=0 and x=1 showed a yellow color and intermediate solid solutions displayed red to dark-red colors. Furthermore, the apparent bowing shown in FIG. 20B is also outside the apparent variations in excitonic features across the pure-Pb (strong excitonic feature) to pure Sn (no apparent excitonic absorption), with typical binding energies of a few tenths of eV. The bowing effect may be attributed to the energy mismatch between s and p orbitals of Pb and Sn forming predominantly Sn/I-derived valence band maximum (VBM) and predominantly Pb/I-derived conduction band minimum (CBM) in the intermediates. Shown below by first-principles calculations is that the apparent bowing also appeared in the band structure calculations of ordered alloy models and thus, is likely a consequence of shifts of the fundamental gap of the alloyed compounds and not (as discussed above) a result of variations in exciton binding energy.

To understand the electronic structure in the alloyed (i.e., mixed Sn/Pb) compounds and elucidate the observed band bowing, DFT-based first-principles calculations were performed on locally ordered models of (S-MBA)$_2$Pb$_{1-x}$Sn$_x$I$_4$ (x=0, 0.25, 0.5, 0.75, 1; note that the observed optical bandgaps of R- and S- are exactly the same) based on the all-electron electric structure code FHI-aims. Input geometries for x=0 and 1 were from single crystal X-ray experiments while for x=0.25, 0.5, and 0.75 they were generated by substituting a corresponding proportion of the metallic atoms in either (S-MBA)$_2$PbI$_4$ or (S-MBA)$_2$SnI$_4$ crystal structures, depending on which is more similar to the target composition. Additionally, for x=0.25 and 0.75, the unit cell size was doubled by two, along the (a,c) plane, including four Sn/Pb sites in each inorganic layer to accommodate the same stoichiometry in each plane. For each modeled compound, atomic positions and unit cell vectors were relaxed towards local minima of the potential energy surface based on the semi-local DFT (PBE generalized-gradient approximation including the Tkatchenko-Scheffler (TS) van der Waals correction, PBE+TS for short). Structures were optimized until all forces on nuclei and lattice parameters were below 5×10$^{-3}$ eV/Å. Computationally optimized lattice parameters were within 2.2% of the experimental geometries. Computationally relaxed inorganic layer bond angles remained within 5° of the above-described input geometries.

Evaluation showed (S-MBA)$_2$PbI$_4$ has a larger bandgap than (S-MBA)$_2$SnI$_4$ (computational estimates of 2.17 eV versus 2.02 eV) and a pronounced bowing effect, caused by alloying. Since the computed gaps do not include excitonic effects (unlike the measured optical spectra reported in FIG. 20B, the experimentally observed trend between the pure Pb/pure Sn end points is thus already found in the computed fundamental gaps. The Mulliken decompositions of the states forming the energy bands reveals that the Pb atoms contribute significantly to the lowest unoccupied states, while Sn species are the more significant cation contributors to the highest-lying occupied states (both the VBM and CBM also contain pronounced contributions from the halide ions). A systematic energy shift between more Pb-derived bands vs. more Sn derived bands in the same unit cell is thus the most likely origin of the observed band bowing.

As a function of overall composition, the band bowing trend was reproduced qualitatively, but not quantitatively, between the experimentally found optical gaps in FIG. 20B and the computationally reported fundamental gaps. In particular, the pronounced compositional asymmetry of the experimental gaps was not seen in the computed gaps. However, in the computations, only fully ordered, idealized small-cell structure models were considered. In contrast, the local distributions of Sn versus Pb atoms in the real samples could be very different and the Sn/Pb ratios in real samples could deviate from the input nominal ratio. For example, the experimentally observed variation would be consistent with the idea that the onset of absorption in the alloyed samples is determined by local mixed Sn/Pb areas with compositions between $0.25<x<0.75$, whereas the average band gap inferred from fitting the slope of the Kubelka-Munk functions in FIG. 20B and/or the overall color of the samples may vary more, depending on the degree of overall sample inhomogeneity. Furthermore, likely variations in the exciton binding energies with x could alter the observed optical gaps with respect to the fundamental band edges considered in the calculations.

A simple computational experiment revealed that the predicted band gaps can indeed vary significantly as a consequence of local inhomogeneities. Uneven cation distributions in the inorganic planes were probed for the particular case of alternating pure Pb (Sn) and 50-50 mixed Pb/Sn planes at compositions x=0.25 (0.75). The result was a significant drop of the overall band gaps, by more than 0.1 eV in both cases. The actual inhomogeneities encountered in real samples are almost certainly different from the simple cases explored here. Importantly, differences in elemental distribution can entirely account for most of the remaining observed differences between the optical gaps of the real materials and the fundamental gaps computed for the alloyed structure models.

The optical and chiroptical properties of the $(R\text{-MBA})_2Pb_{1-x}Sn_xI_4$ solid solution was further studied by spin casting a DMF solution of corresponding crystals. Linear absorption spectra of thin films show similar absorption features as powder samples (see FIG. 21A). For instance, both $(R\text{-MBA})_2PbI_4$ and $(R\text{-MBA})_2Pb_{0.95}Sn_{0.05}I_4$ exhibited a characteristic exciton peak at ~498 nm, while other compositions (x=0.20, 0.50, 0.80, and 1) did not show distinct exciton peaks. The absorption onset of $(R\text{-MBA})_2Pb_{0.80}Sn_{0.20}I_4$ also appears to be the lowest energy among all compositions. The crystalline texture of these films was further characterized by XRD (see FIG. 21B). XRD data display exclusively (0 2k 0) peaks, indicating that these 2D Sn-I perovskite layers are highly oriented parallel to the substrate, similar to their Pb analogs. Additionally, there is minimum to no shift with XRD peaks between different compositions, which is consistent with powder diffraction data, as well as, with the computed lattice parameters. This is because the observed peaks represent the interlayer distance between inorganic sheets, which is mostly defined by the organic layers and thus essentially unchanged.

To further illustrate how the tunable electronic structures can modulate their chiroptical properties, CD measurements were performed on $(R\text{-MBA})_2Pb_{1-x}Sn_xI_4$ (x=0, 0.05, 0.20, 0.50, 0.80, 1) thin films (see FIG. 22). The CD spectra clearly show peak shifts across the whole range of $(R\text{-MBA})_2Pb_{1-x}Sn_xI_4$ (x=0 to 1), with R- and S-compounds displaying bisignate features with opposite signs. The chiroptical properties of chiral $(R\text{-}/S\text{-MBA})_2PbI_4$ are discussed above characterized by distinct derivative features near the band edge (at 497 nm and 508 nm) resulting from the Cotton effect. Interestingly, these derivative peaks near the band edge disappeared upon mixing with Sn even at a 5% concentration level. Therefore, to better analyze the shift of the CD spectra, focus was placed on the second lowest energy peak (vertical dashed-line). The shift of these peaks was followed assuming that the same handedness of hybrid compounds should result in the same sign (positive or negative) for that CD peak across all solid solution compositions, since the same chirality would perturb that electronic transition in the same manner. The second lowest energy peak clearly shows a redshift from 380 to 406, 413, and 466 nm when the Sn concentration was increased from 0, to 5, 20, and 50%, respectively (dashed-line). When Sn concentration was further increased to 80 and 100%, the CD peaks blue-shift. Therefore, the CD spectra can be tuned in $(R\text{-MBA})_2Pb_{1-x}Sn_xI_4$ (x=0, 0.05, 0.20, 0.50, 0.80, 1) solid solution, pointing to the modulation of chiroptical properties by tuning the electronic structures of these chiral hybrid semiconductors.

To investigate the CISS effect in these chiral Sn-I compounds, magnetic conductive-probe atomic force microscopy (mCP-AFM) measurements were performed on $(R\text{-}/S\text{-MBA})_2SnI_4$ thin films. The $(R\text{-}/S\text{-MBA})_2SnI_4$ films were prepared by spin casting a DMF solution of crystals on FTO-coated glass substrates. Compared to their chiral Pb-analogs, the chiral Sn-I films appeared to be much more conductive likely due in part to the spontaneous p-type doping of the Sn-I crystals. In this study, A bias from −1.2 to 1.2 V was applied and the vertical current transport measured through the chiral organic/inorganic sublattices for different AFM tip magnetizations. When the AFM tip is magnetized by a permanent external magnet, the spin-degeneracy of carriers in the tip is lifted, so that only one spin-state is predominately injected into the thin film. CISS introduces an addition spin scattering effect for carriers and thus increases the resistance for carriers with a particular spin orientation. Based on the difference in the measured J-V characteristics under the opposite tip magnetization directions, the degree of spin polarization, P, was defined for the current in the system during vertical charge transport.

$$P = \frac{I_+ - I_-}{I_+ + I_-} \times 100\%$$

Where $I_+$ and $I_-$ are the measured currents at −1 V when the tip magnetic field is pointing up or down, respectively. A highly spin-polarized current was obtained, P of +94%, in the $(R\text{-MBA})_2SnI_4$ film, which was slightly higher than the analogous $(R\text{-MBA})_2PbI_4$ film discussed above. In contrast, the $(S\text{-MBA})_2SnI_4$ film yielded a spin polarization of −93%. The small difference in the measured spin-polarized current between $(R\text{-MBA})_2PbI_4$ and $(R\text{-MBA})_2SnI_4$ thin films suggests that spin-dephasing within in the inorganic sublattice (caused by large spin-orbit coupling from the heavy Pb or Sn atoms) likely is not significant in these self-assembled chiral organic/inorganic structures. Thus, the spin-polarized current is mostly attributed to the effect of the spin-filtering from the oriented chiral organic molecules (increased resistance to carriers with the incorrect spin orientation). Here the transport requires carriers to transverse many layers. It was previously determined that to achieve nearly 100% spin-polarization the carriers would need to transport through ~60-80 nm of the oriented chiral layers. The degree of spin-orbit coupling in a typical oriented chiral organic molecule has been found to be related to the number of turns of the helical potential. Here, it appears each oriented layer contributes to the overall polarized current likely in similar manner as that for each turn of a much longer oriented chiral molecule.

Materials and Methods:

Materials: All chemicals were used as received unless otherwise indicated. (R)-(+)-α-methylbenzylamine (R-MBA, 98%, ee 96%), (S)-(−)-α-methylbenzylamine (S-MBA, 98%, ee 98%), (±)-α-methylbenzylamine (rac-MBA, 99%), lead oxide (PbO, 99.999%), N,N-anhydrous dimethylformamide (DMF), and 57% aqueous hydriodic acid (HI) solution (99.95%, distilled, stabilized by $H_3PO_2$) were purchased from Sigma-Aldrich. Phenethylammonium iodide (PEAI) was purchased from Greatcell Solar. Tin (IV) oxide ($SnO_2$, 99.9%) was purchased from Alfa-Aesar, and it was ground using a mortar pestle before synthesis, which assist to dissolve in $HI/H_3PO_2$ solution.

Synthesis of $(R-MBA)_2PbI_4$, $(S-MBA)_2PbI_4$, and $(rac-MBA)_2PbI_4$ single crystals: The synthesis of the 2D chiral perovskite single crystals was adapted from literature reports. Generally, 200 mg of PbO (0.897 mmol), 200 μL (1.57 mmol) of R-, S-, or rac-MBA, and 6 mL of HI solution were loaded into a glass vial. The as formed yellow precipitates were subsequently dissolved at 90° C. in an oil bath. The solution was slowly cooled to room temperature with a cooling rate of 1° C./h, giving orange needles. These crystals were vacuum filtrated and rinsed with diethyl ether. The final product was dried in vacuum overnight.

Synthesis of $(R-/S-/rac-MBA)_2SnI_4$ single crystals. The synthesis of 2D chiral Sn-I perovskite single crystals was the same as for 2D chiral Pb-I perovskite single crystals. All syntheses in the work are performed in air. Briefly, 135 mg of grinded $SnO_2$ (0.896 mmol), 200 μl (1.57 mmol) of R-, S-, or rac-MBA, 5.5 ml of HI, and 0.5 ml $H_3PO_2$ solution were loaded into a glass vial. The mixture was then stirred at 120° C. until all solids were dissolved, yielding a clear yellow solution. The vial was subsequently transferred to an oil bath at 90° C., followed by a slow cooling process with a cooling rate of 1° C./hour, giving orange rods. These crystals were carefully filtered in a $N_2$ box and dried in vacuum overnight.

Synthesis of $(PEA)_2PbI_4$ single crystals: 2D achiral perovskite $(PEA)_2PbI_4$ single crystals are synthesized based on previously reported cooling method. Briefly, 127 mg (0.57 mmol) of PbO and 286 mg (1.15 mmol) of PEAI are fully dissolved in 10 mL of HI solution at 90° C. The solution is then slowly cooled to room temperature at a rate of 1° C./h, giving orange sheet-like crystals. The crystals are then isolated from the parent solution by vacuum filtration and dried under vacuum.

Preparation of $(R-MBA)_2PbI_4$, $(S-MBA)_2PbI_4$, $(rac-MBA)_2PbI_4$, and $PEA_2PbI_4$ thin films: Glass, quartz, FTO (resistance<25Ω) or ITO substrates are washed sequentially by acetone and isopropanol in a sonicator for 10 min each, followed by an UV-ozone treatment for 15 min. The precursor solutions are prepared by dissolving the corresponding perovskite crystals in DMF with various concentrations (10 wt % for the mCP-AFM measurements). Thin films are then prepared by spin coating the precursor solution on to substrates using a spin-rate of 4000 rpm for 30 seconds, followed by annealing at 100° C. for 10 min. Thin films on glass substrates are used for XRD and AFM measurements. Thin films on quartz substrates are used for optical (linear absorption and CD) measurements. Thin films on FTO or ITO are used for mCP-AFM and magnetoresistance measurements.

Synthesis of $(R-MBA)_2Pb_{1-x}Sn_xI_4$ (x=0–1) single crystals. Synthesis of solid solution $(R-MBA)_2Pb_{1-x}Sn_xI_4$ (x=0–1) single crystals is similar to pure $(MBA)_2SnI_4$ crystals. In general, different molar ratios of $SnO_2$ and PbO ($r_{Sn:Pb}$=0:1, 0.05:0.95, 0.20:0.80, 0.50:0.50, 0.80:0.20, 1:0, total of 0.896 mmol) were mixed with 200 μl (1.57 mmol) of R-MBA, 5.5 ml of HI, 0.5 ml $H_3PO_2$ solution in a glass vial. The mixture was stirred at 120° C. until all solids were dissolved, followed by a slow cooling process in an oil bath from 90° C. to room temperature. Orange to dark red needle crystals were collected in a $N_2$ box by vacuum filtration. The final products were dried in vacuum overnight. The actual elemental composition was analyzed by EDS for these crystals.

Preparation of $(R-/S-/rac-MBA)_2SnI_4$ and $(R-MBA)_2Pb_{1-x}Sn_xI_4$ thin films. Glass, quartz or FTO substrates were washed sequentially using acetone and isopropanol in a sonicator for 100 min each, followed by an ultraviolet-ozone treatment for 15 min. Precursor solutions were prepared by dissolving crystals in DMF with 10 wt % (e.g. 20 mg in 200 μl) and were immediately used. Thin films were prepared by spin coating the corresponding precursor solution onto substrates using a spin rate of 4000 rpm for 30 s, followed by thermal annealing at 100° C. for 10 min. Thin films on glass substrates were used for XRD measurements. Thin films on quartz substrates were used for linear optical and CD measurements. Thin films on FTO were used for mCP-AFM measurements.

XRD measurements: Traditional θ/2θ XRD measurements of the thin film systems were taken on a Rigaku DMax 2200 diffractometer with a rotating Cu anode. Complementary 2D XRD measurements to asses texture were taken with a Broker D8 Discovery system with a GADDS (General Area Detector Diffraction System) 4-circle detector and fixed Cu source.

CD measurements: CD measurements were carried out using a Jasco J-715 spectropolarimeter with the thin film placed in the beam path. The spectra obtained were averages of five scans. The spectra were smoothed using an internal algorithm in the Jasco software package, J-715 for Windows. The CD spectra of different constructs was monitored from 200-600 nm with 0.2 nm resolution, and the data presented as the raw CD signal.

AFM measurements: The AFM topography images were taken by tapping mode with silicon cantilever (spring constant ~42 N/m) at a resonant frequency of 200-400 kHz. The depth profile AFM sample was prepared by vertically scratching the sample surface with a new blade.

mCP-AFM measurements: Conductive-AFM results were collected by a Veeco D5000 AFM system in an Ar-filled glovebox equipped with the Nanoscope V controller. A Bruker MESP-V2 tip (spring constant ~3 N/m) was used in contact mode, the Co—Cr coated tips were pre-magnetized by a strong permanent magnetic for >30 minutes and then used for the scan immediately. The tip was placed back to the same pole of magnetic again for 30 minutes if measurement time is longer than 60 minutes. I-V curves were acquired by ramping the voltage from −2 V to +2 V with a frequency of 0.5 Hz. The bias voltage was applied to the sample, where the tip was virtually grounded. One magnetized tip was used to scan the three type of samples; and after scanning on all samples, the first sample was rescanned to confirm that there was no significant change of the tip. With the tip magnetized by different field orientations (magnetic south, north, no magnetic), more than 100 I-V curves were taken from different locations on each sample.

Device fabrication and magnetoresistance measurements: The ITO bottom electrode on glass substrate was patterned by wet etch photolithography. The ITO electrode was cleaned by sonication in acetone and isopropanol for 15 minutes. Subsequently the bottom electrode was treated by oxygen plasma for 10 minutes. The chiral perovskites film was spin coated on the pre treated ITO electrode inside a N₂ filled glovebox (O₂/H₂O<1 ppm). The chiral perovskites film was then annealed at 100° C. for 10 minutes. After cooling down to ambient temperature, the sample was transferred to a vacuum chamber at pressure of $10^{-7}$ Torr for electron beam deposition of 5 nm NiFe film as top electrode in a cross-section configuration. Finally, a 30 nm thick Au film was coated for encapsulation purpose. The device area was 1×1 mm.

Following the fabrication process the spin valve-like device was transferred to a closed-cycle cryostat for transport measurements. All the measurements were done at 10 K. The device resistance was measured by a standard four points method with Keithley 236 power supply and Keithley 2000 multimeter, while an out-of-plane magnetic field up to 200 mT was applied for magnetoresistance measurements.

Exciton and CD spectra fitting: The analysis of linear absorption and CD spectra is adapted from the protocol reported by Markovich. Exciton peak can be fitted approximately using a Gaussian function:

$$\text{Abs}(\lambda) = A_0 e^{-\frac{(\lambda-\lambda_0)^2}{2\sigma_0^2}}$$

The center of the Gaussian frequency $\lambda_0$ represents excitonic level and is determined to be 500.53 nm from fitting. The CD spectrum measures the excitonic level dissymmetry resulting from the perovskite's interaction with its chiral molecules and is sensitive to small energy level shifts in exciton energy. The CD spectrum then can be modeled as differences between Gaussians formed by small shifting ($\Delta\lambda$) from the original center Gaussians in the absorption spectrum:

$$CD(\lambda) = A_0 e - A_0 e^{-\frac{(\lambda-\lambda_0+\Delta\lambda)^2}{2\sigma_0^2}} - A_0 e^{-\frac{(\lambda-\lambda_0)^2}{2\sigma_0^2}}$$

By fitting the CD spectrum of both R- ans S-isomers, the energy level shift can be determined with $\Delta\lambda_s=2.7$ nm and $\Delta\lambda_R=7.8$ nm. And the relative energy level splitting can be calculated as:

$$\Delta E(eV) = \frac{1240\text{ nm}}{(\lambda_0+\Delta\lambda_R)} - \frac{1240\text{ nm}}{(\lambda_0+\Delta\lambda_S)}$$

The calculated $\Delta E$ is approximately 51.3 meV.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A composition comprising:
   a perovskite comprising $A_2BX_4$, wherein:
   A comprises an R-form of a chiral molecule comprising at least one of

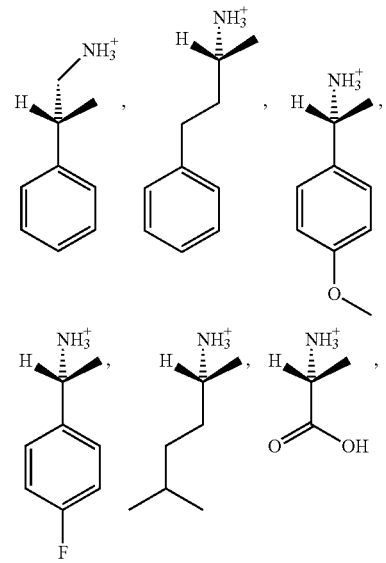

or an S-form of the chiral molecule,
   B comprises a cation, and
   X comprises an anion.

2. The composition of claim 1, wherein the composition demonstrates spin-polarization of charge transport when a current is injected into the composition.

3. The composition of claim 1, wherein B comprises at least one of lead, tin, or germanium.

4. The composition of claim 1, wherein X comprises a halogen.

5. The composition of claim 1, wherein the perovskite comprises at least one of $R-A_2PbI_4$, $S-A_2PbI_4$, $R-A_2SnI_4$, $S-A_2SnI_4$, $R-A_2Pb_{1-x}Sn_xI_4$, $S-A_2Pb_{1-x}Sn_xI_4$, wherein $0<x<1$.

6. The composition of claim 1, wherein:
   the perovskite is in a form comprising a first two-dimensional (2D) network and a second 2D network,
   the first 2D network comprises $BX_4$,
   the second 2D network comprises $BX_4$, and
   a plurality of the chiral molecule forms a layer positioned between the first 2D network and the second 2D network.

7. The composition of claim 1, wherein the perovskite is in a shape of a film having a thickness between about 10 nm and about 100 nm.

8. The composition of claim 7, wherein the film has a roughness between about 1 nm and about 5 nm.

9. The composition of claim 1, wherein the perovskite has a bandgap between about 2.2 eV and about 3.0 eV.

10. The composition of claim 1, wherein the perovskite is capable of demonstrating chiral induced spin selectivity.

11. The composition of claim 8, wherein the film of the perovskite is polycrystalline.

12. A device comprising:
   a ferromagnetic (FM) electrode;
   a non-FM electrode; and
   a perovskite film comprising $A_2BX_4$, wherein:
   the perovskite film is positioned between the FM electrode and the non-FM electrode,
   A comprises an R-form of a chiral molecule comprising at least one of

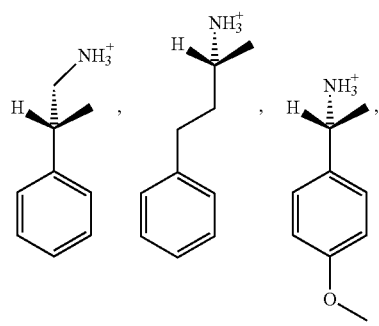

-continued

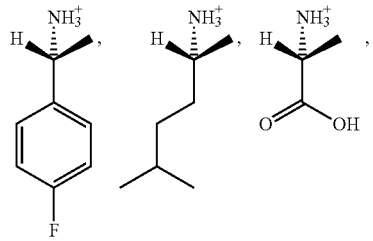

or an S-form of the chiral molecule,
   B comprises a cation, and
   X comprises an anion.

13. The device of claim 12 configured to operate as at least one of an FM electrode, a spin filter, a spin polarized LED, a spin polarized laser, an op spin-valve, a spin-diode, a spin-transistor, a chiral-light detector, a switchable optical memory, a polarization selective optical multiplexor, or an ultrafast modulator.

14. The device of claim 12, wherein the non-FM electrode comprises a transparent conducting oxide (TCO).

15. The device of claim 14, wherein the TCO comprises indium tin oxide.

16. The device of claim 12, wherein the FM electrode comprises nickel and iron.

17. The device of claim 16, wherein the FM electrode has a thickness between about 1 nm and about 10 nm.

18. The device of claim 12, further comprising:
   a metal layer, wherein:
   the FM electrode is positioned between the metal layer and the perovskite film.

19. The device of claim 18, wherein the metal layer is a gold layer.

20. The device of claim 12, wherein the perovskite film demonstrates spin-polarization of charge transport when a current is injected into the perovskite film.

* * * * *